(12) United States Patent
Hirsch

(10) Patent No.: US 7,491,523 B2
(45) Date of Patent: Feb. 17, 2009

(54) VOLTAGE-DEPENDENT CALCIUM CHANNEL BETA SUBUNIT FUNCTIONAL CORE

(76) Inventor: Joel A. Hirsch, 8 Alterman, Raanana 43231 (IL)

( * ) Notice: Subject to any disclaimer, the term of this patent is extended or adjusted under 35 U.S.C. 154(b) by 183 days.

(21) Appl. No.: 11/126,313

(22) Filed: May 11, 2005

(65) Prior Publication Data

US 2005/0288489 A1 Dec. 29, 2005

Related U.S. Application Data

(60) Provisional application No. 60/569,642, filed on May 11, 2004.

(51) Int. Cl.
*C12N 9/12* (2006.01)
*G01N 31/00* (2006.01)

(52) U.S. Cl. .......................... 435/194; 436/4

(58) Field of Classification Search ........................ None
See application file for complete search history.

(56) References Cited

OTHER PUBLICATIONS

Opatowsky et al., The Voltage-Dependent Calcium Channel Beta Subunit Contains Two Stable Interaction Domains. The Journal of Biological Chemistry. 2003. vol. 278, No. 52, pp. 52323-52332.*
Dolphin et al. Beta Subunits of Voltage-Gated Calcium Channels. Journal of Bioenergetics and Biomembranes. 2003. vol. 35, No. 6, pp. 599-620.*
McPherson, A. Current Approaches to Macromolecular Crystallization. European Journal of Biochemistry. 1990. vol. 189, pp. 1-23.*
Weber, P.C. Overview of Crystallization Methods. Methods in Enzymology. 1997. vol. 276, pp. 13-22.*
Drenth, "Principles of Protein X-Ray Crystallography", 2nd Edition, 1999 Springer-Verlag New York Inc., Chapter 1, p. 1-21.*
Cudney R. Protein Crystallization and Dumb Luck. The Rigaku Journal. 1999. vol. 16, No. 1, pp. 1-7.*
Kundrot, C.E. Which Strategy for a Protein Crystallization Project? Cellular Molecular Life Science. 2004. vol. 61, pp. 525-536.*
van Petegem et al., Structure of a Complex Between a Voltage-gated Calcium Channel Beta-Subunit and an Alpha-subunit Domain. Nature. Jun. 2004. vol. 429, pp. 671-675 and Supplemental pp. 1-9.*
Chen et al. Structural Basis of the alpha1-beta Subunit Interaction of Voltage-gated Calcium Channels. Nature. Jun. 2004. vol. 429, pp. 675-680.*
Opatowsky et al. The Voltage-Dependent Calcium Channel Beta Subunit Contains Two Stable Interacting Domains. The Journal of Biological Chemistry. vol. 278, No. 52, pp. 52323-52332.*
Berrou, L., Klein, H , Bernatchez, G , and Parent, L. (2002). A specific tryptophan in the I-II linker is a key determinant of beta-subunit binding and modulation in Ca(V)2 3 calcium channels. Biophys J 83, 1429-1442.
Chen, Y.H., Li, M H , Zhang, Y., He, L L , Yamada, Y., Fitzmaurice, A., Shen, Y., Zhang, H., Tong, L., and Yang, J. (2004). Structural basis of the alpha1-beta subunit interaction of voltage-gated Ca2+ channels. Nature 429, 675-680.
De Waard, M., Scott, V E., Pragnell, M , and Campbell, K. P. (1996). Identification of critical amino acids involved in alpha1-beta interaction in voltage-dependent Ca2+ channels FEBS Letters 380, 272-276.
Van Petegem, F., Clark, K.A., Chatelain, F.C., and Minor, D.L. Jr (2004) Structure of a complex between a voltage-gated calcium channel beta-subunit and an alpha-subunit domain. Nature 429, 671-675.
Witcher, D R., De Waard, M., Liu, H., Pragnell, M , and Campbell, K P (1995). Association of native Ca2+ channel beta subunits with the alpha 1 subunit interaction domain J Biol Chem 270, 18088-18093.

* cited by examiner

*Primary Examiner*—David J. Steadman
*Assistant Examiner*—Suzanne M. Noakes
(74) *Attorney, Agent, or Firm*—Pearl Cohen Zedek Latzer, LLP

(57) ABSTRACT

The present invention relates to crystallized forms of a voltage dependent calcium channel β subunit functional core, methods of producing and methods of utilizing the same.

18 Claims, 17 Drawing Sheets
(3 of 17 Drawing Sheet(s) Filed in Color)

FIG. 3
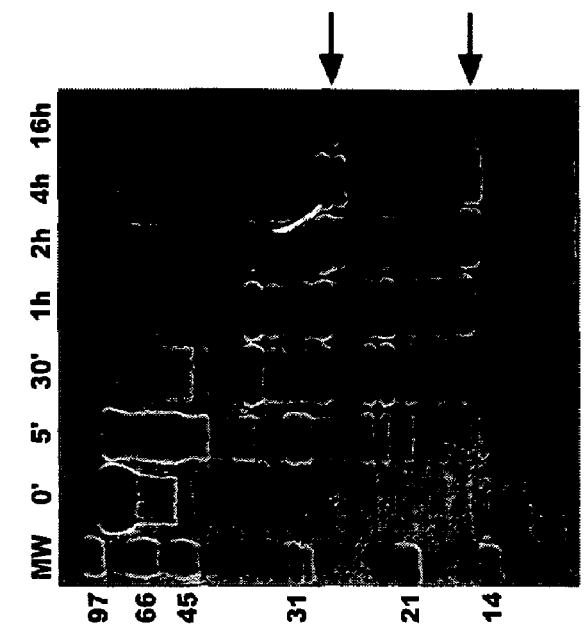
B
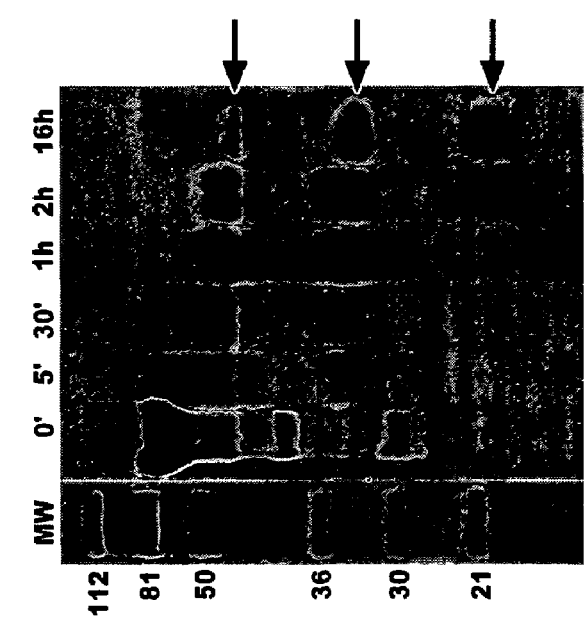
A

CD Spectra of VDCC β proteins

FIG. 7
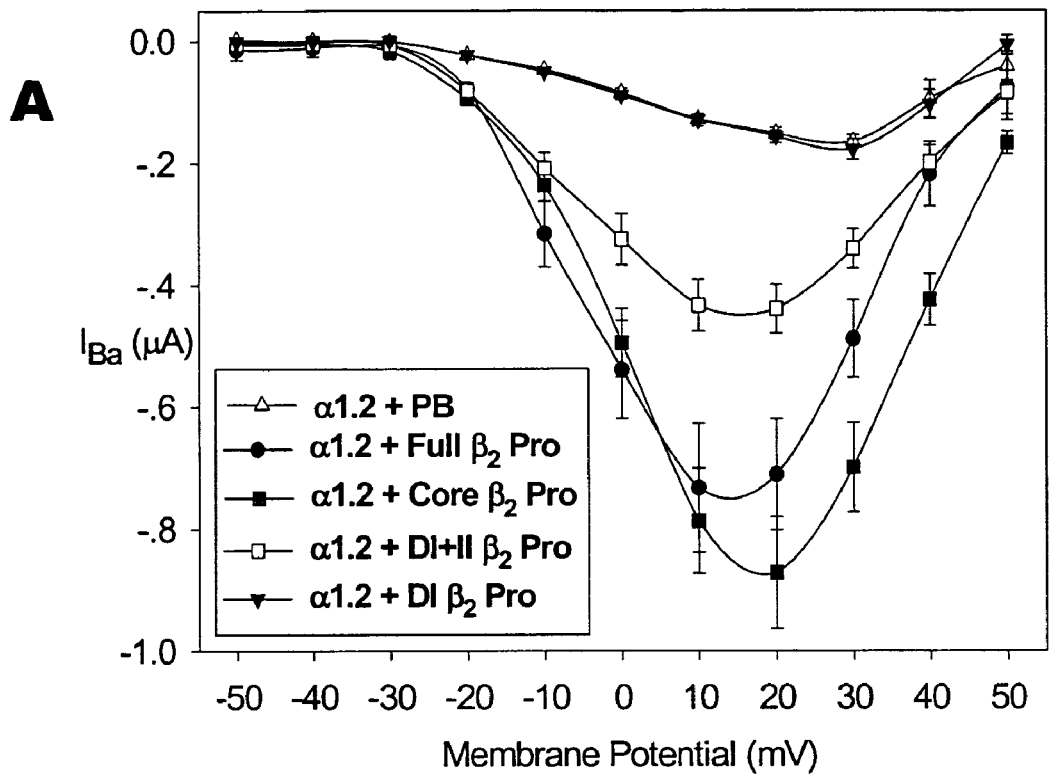
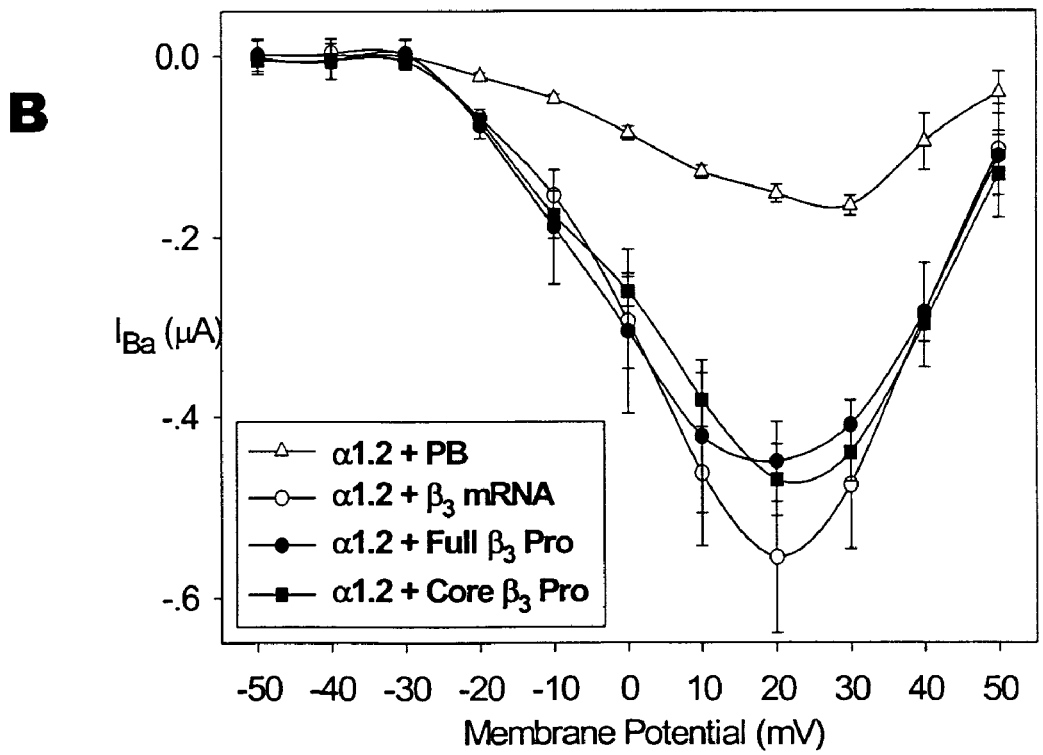

A    B
 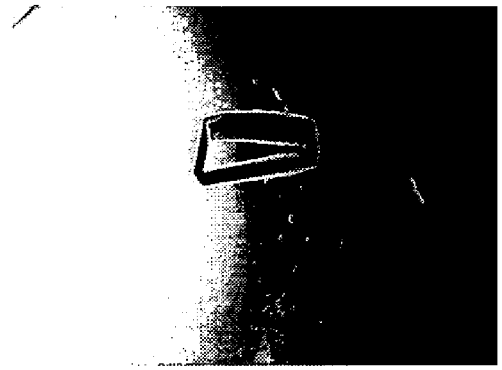
Figure 10

FIG. 11
A 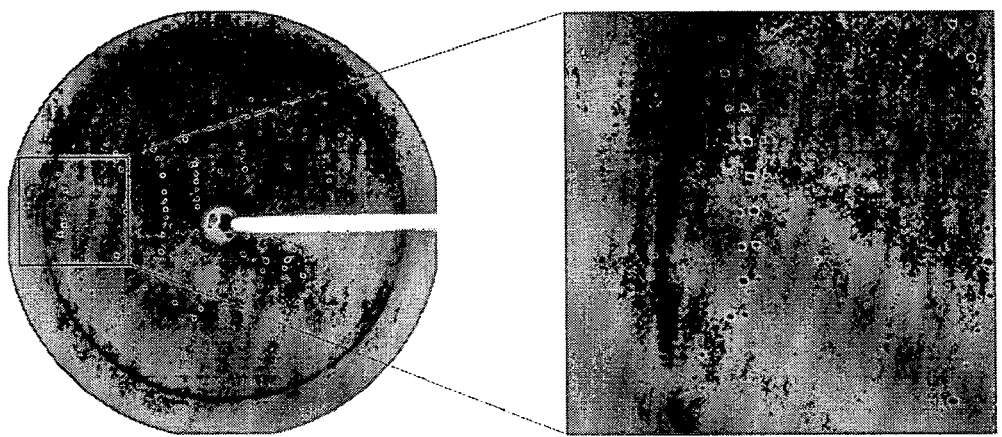
B 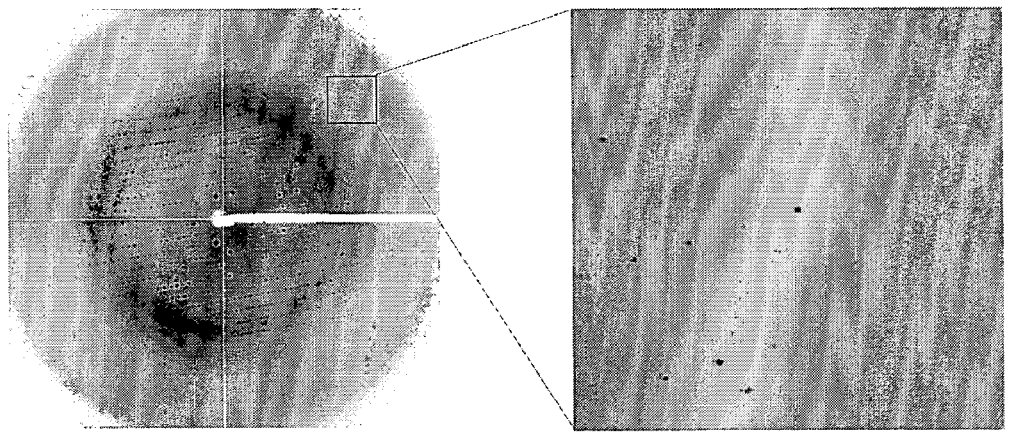

FIG. 12
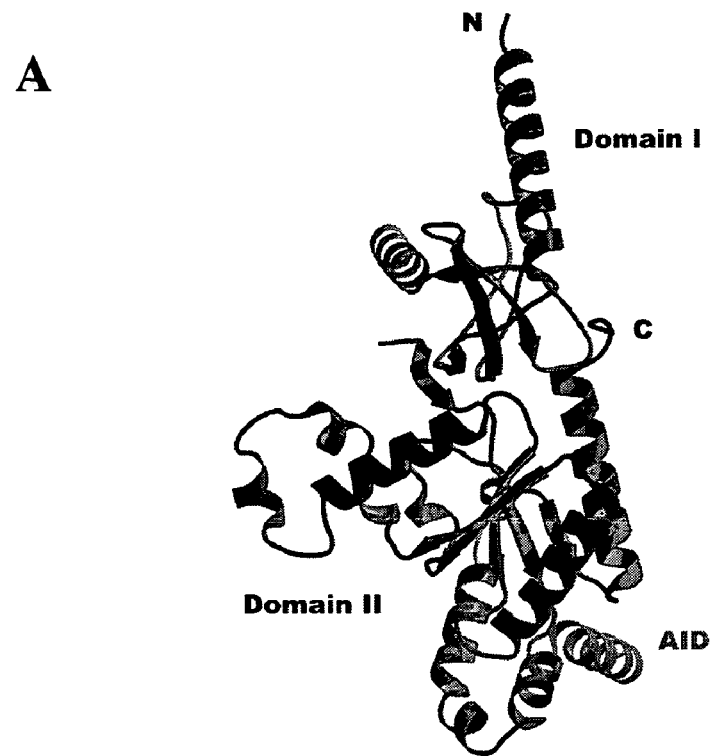
A
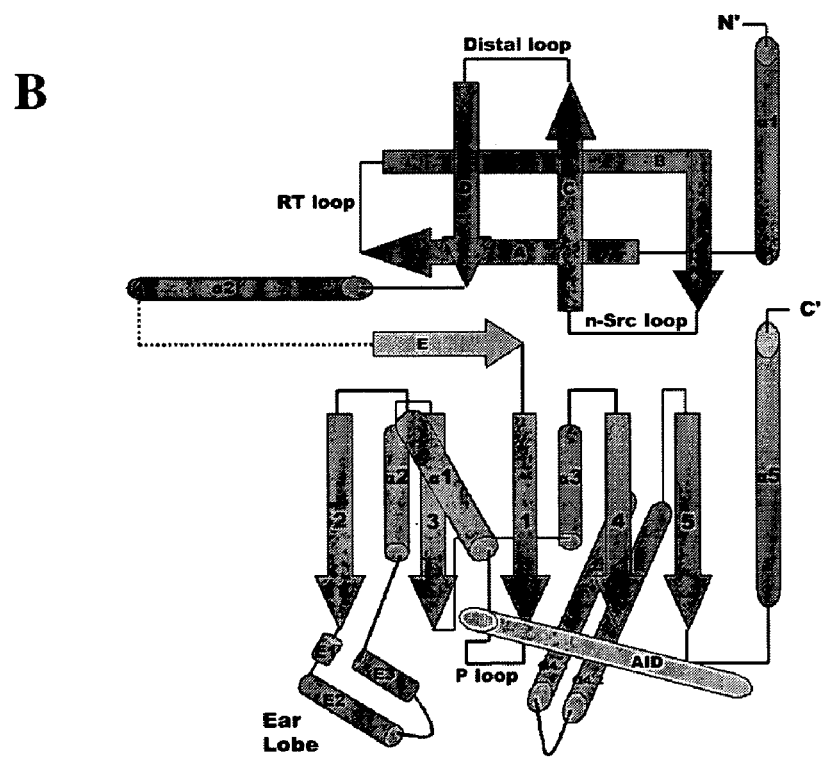
B

```
                          α1                          A       <  RT-loop  >    n-Src
                                                                                  B  loop
             33      40        50        60        70        80        90        100
CCβ2a     33 SLEEDREAVRREAERQAQAQLEKAKTKPVAFAVRTNVSYSAAHEDDVPVPGMAISFEAKDFLHVKEKFNND
CCβ3      31 VLEEDRESARREVESQAQQQLERAKHKPEAFAVRTNVSYCGVLDEECPVQGSGVNFEARDFLHIKEKYSND
CCβAnoph  71 SLDEEKESLRREKERQALGQLEKARSKPVAFAVRTNVSYDGSLDDDSPVHGSAVSFEVGDFLHIKEKYDNN
PSD-95   430 -------------------------------GFYIRALFDYDKTKDCGFL--SQALSFRFGDVLHVIDAGDEE
Crk1     134 -------------------------------AEYVRALFDFNGNDEE-------DLPFKKGDILRIRDKPEEQ distal
                  Loop         C       D       α2            β's variable
             110        120       130                        linker
CCβ2a     WWIGRLVKEGC---EIGFIPSP--VKLENMRLQHEQRAKQ 138        218 -TPPYDVVPS 226
CCβ3      WWIGRLVKEGG---DIAFIPSP--QRLESIRLKQEQKARR 136        167 -VPPYDVVPS 175
CCβAnoph  WWIGRLVKEGC---EVGFIPSP--VKLEHIRMQASAARSS 176        245 -SSPYDVVPS 253
PSD-95    WWQARRVHSDSETDDIGFIPSK--RRVERREWSRLKAKDW 507        520 VL-SYETV-- 526
Crk1      WWNAEDSEGKR-----GMIPVPYV--------------------------- -E-KY-- 190

P-loop           α1
             230        240        250        260
CCβ2a    227 MRPVVLVGP---SLKGYEVTDMMQKALFDFLKHRFEGRISITRVT---------------
CCβ3     176 MRPVVLVGP---SLKGYEVTDMMQKALFDFLKHRFDGRISITRVT---------------
CCβAnoph 254 MRPVVLVGP---SLKGYEVTDMMQKALFDFLKHRFESRIIITRVQ---------------
PSD-95   535 -RPIIILGP--T------------KDRANDDLLSEFPDKFGSCVPHTTRPKREYEIDGRDYHFVSSREKMEK
GUKyeast   2 SRPIVISGPSGT------------GKSTLLKKLFAEYPDSFGFSVSSTTRTPRAGEVNGKDYNFVS-VDEFKS 270       280       290            α2
                                                   300        310
CCβ2a    269 -----------------ADISLAKRSVLNNPSKHAIIERSNTR-SSLAEVQSEIERIFELARTL
CCβ3     218 -----------------ADLSLAKRSVLNNPGKRTIIERSSAR-SSIAEVQSEIERIFELAKSL
CCβAnoph 296 -----------------ADISLAKRSLMNNPSKRAIMERSNSRSSCLAEVQAEIERIFELARTL
PSD-95   592 DIQAHKFIEAGQYNSHLYGT---------------------------------SVQSVREVAEQG
GUKyeast  62 MIKNNEFIEWAQFSGNYYGS---------------------------------TVASVKQVSKSG 320       330       340           α4
                                            350        360
CCβ2a    315 QLVVLDA-DTIN---HPAQLSKT-SLAPIVVYVKI-SSPKVLQRLIKSRG-KSQAK--H
CCβ3     264 QLVVLDA-DTIN---HPAQLAKT-SLAPIIVFVKU-SSPKVLQRLIRSRG-KSQMK--H
CCβAnoph 343 QLVVLDC-DTIN---HPSQLAKT-SLAPTIVYLKI-ASSKVLQRLIRSRG-KAQAK--H
PSD-95   624 KHCILDVS---ANAV--RRLQAA-HLHPIAIFIRPR-SLENV---LEINKR--I-TEEQ
GUKyeast  94 KTCILDID---MQGV--KSVKAIPELNARFLFIAPP-SVEDLKKELEGRGT--E-TEES α4-2            5         α5
             370       380       390       400       410
CCβ2a    365 LNVQM-VAADKLAQC---PPELFDVILD-ENQLEDACEHLADYLE-A-Y-WKATHPPSSN 416
CCβ3     314 LTVQM-AY-DKLVQC---PPESFDVILD-ENQLEDACELLAEYLE-V-Y-WRATHHPAPG 364
CCβAnoph 393 LSVQM-VAAEKLSQC---PPEMFDVILD-ENQLEEACNHLAEYLE-A-Y-WRATHPPVRP 444
PSD-95   670 ARKAFDRATKLEQEFTEC---FSAIVEG-DSFEEIYHKVKRVIEDLSGPYIWVPARER 723
GUKyeast 144 INKRL-SAAQAELAYAET-GAHDKVIVN-DDLDKA-YKELKDFIFA-EK 187
```

B

```
Cav1.1 HUMAN 335 GEFTKEREKAKSRGTFQKLREKQQLDEDLRGYMSWITQGE
Cav1.2 HUMAN 406 GEFSKEREKAKARGDFQKLREKQQLEEDLKGYLDWITQAE
Cav1.3 HUMAN 407 GEFSKEREKAKARGDFQKLREKQQLEEDLKGYLDWITQAE
Cav1.4 HUMAN 373 GEFSKEREKAKARGDFQKQREKQQMEEDLRGYLDWITQAE
Cav2.1 HUMAN 361 GEFAKERERVENRRAFLKLRRQQQIERELNGYMEWISKAE
Cav2.3 HUMAN 353 GEFAKERERVENRRAFMKLRRQQQIERELNGYRAWIDKAE
Cav2.1 ANOPH 264 GEFARERERKVENRQEFLKLRRQQQLEKELNGFVEWICKAE
Cav2.2 ANOPH 316 GEFARERERKVENRQEFLKLRRQQQLEKELNGYVEWICKAE
Cav1.1 DISOC 349 GEFAKERERVENRRGLFQKLRRQQQVEQEFNRYLRWIHIAE
Cav2.1 C.ELE 369 GEFSKEREKARARGLFQKFREKQQLEEDLKGYLDWITQAE
```

FIG. 17
A
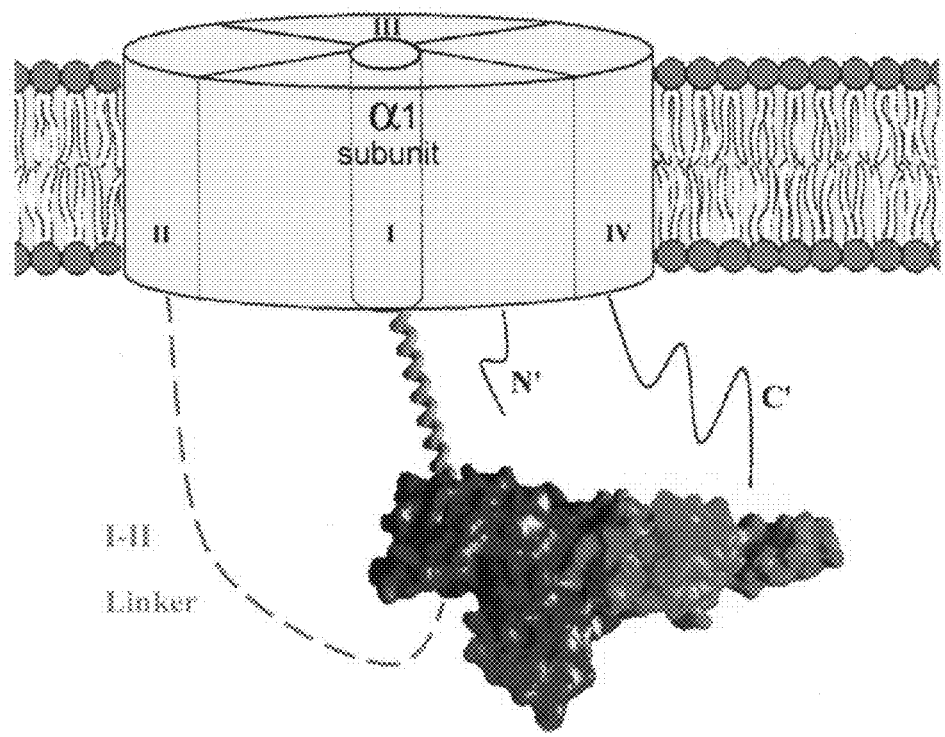
B
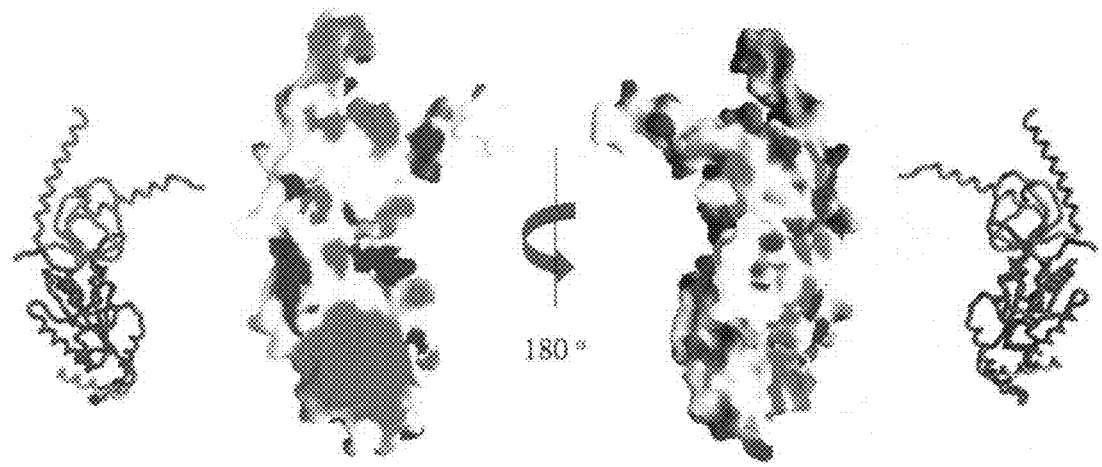

VOLTAGE-DEPENDENT CALCIUM CHANNEL BETA SUBUNIT FUNCTIONAL CORE

CROSS REFERENCE TO RELATED APPLICATIONS

This application claims benefit of U.S. Provisional Application Ser. No. 60/569,642, filed May 11, 2004, which is hereby incorporated by reference.

FIELD OF THE INVENTION

The present invention relates to crystallized, voltage-dependent calcium channel β subunit functional cores, methods of producing the same and methods of use thereof for identification of agents that inhibit or promote voltage dependent calcium channel acitivity. This invention further relates to an isolated polypeptide of a voltage-dependent calcium channel (VDCC) β subunit functional core comprising SH3 and guanylate kinase-like domains and methods of regulating voltage-dependent calcium channels.

BACKGROUND OF THE INVENTION

The passage of $Ca^{2+}$ in a selective manner across the lipid bilayer of the cellular plasma membrane occurs by way of several protein families, one of them being voltage-dependent calcium channels (VDCC). These channels are multi-protein assemblies that serve as "switchboards" for the highly regulated $Ca^{2+}$ signal. They communicate with a large number of cellular players involved in amplifying, terminating or modulating this critical pathway.

Two classes of assemblies gate the flow of $Ca^{2+}$ in response to the voltage state of the plasma membrane. The structurally related but distinct classes are sensitive to low (CaV3) or higher (CaV1 or 2) relative voltage shifts. CaV1 or 2 subfamilies couple excitation of the cell to a variety of processes, depending on cell type, including contraction, secretion and transcription. Furthermore, signal pathway crosstalk requires regulation of channel action by a small host of molecules. An example of such interactions is the GPCR signaling modulation of CaV2 channels. Association of liberated Gbg with the calcium channel as a result of GPCR activation has a notable effect on function, with Gbg behaving as an allosteric effector.

The VDCC (CaV1 or 2), as defined by biochemical purification of the stable complex, comprises four distinct polypeptides: α1, α2d, β and γ. α1 is the membrane pore forming subunit, which contains four transmembrane domains repeats, paralleling the tetrameric architecture of potassium channels. Each domain contains the canonical voltage-dependent ion channel organization i.e. six putative transmembrane segments. The membrane domains are connected by linkers located in the intracellular milieu, as are both the amino- and carboxy-termini. β, in contrast, is a soluble and intracellular protein. Four separate β genes have been catalogued, each with multiple splice variants. All four genes are expressed in the brain, while other tissues exhibit essential gene-specific expression, giving rise to embryonic lethality in β1 and β2 knockout mice. β3 and β4 knockouts or alleles lead to pathologies in a variety of physiological systems.

Since molecular cloning of β, much attention has been focused on its role in VDCC function. Two major directions emerged from these studies. First, β facilitates the proper localization or trafficking of the VDCC and the α1 subunit in particular to the cellular plasma membrane. Several different β isoforms chaperone the channel to its target. Second, β acts as an important modulator of the channel's electrophysiological properties. β alters activation and inactivation kinetics, causes a leftward shift in the I-V curve and, on the single channel level, induces an increase in the channel opening probability. Furthermore, the localization functionality has a marked impact on the electrophysiological aspect by increasing the number of channels at the membrane, significantly enhancing current amplitude.

The groundwork for understanding β's molecular mechanism was laid with the discovery that β bound α1 through a region in the linker between domain I and II, labeled the AID (for α1 interaction domain). Later studies have shown that β also interacts with other regions of α1, depending on the isoform, but the AID appears to be the primary, high affinity site of interaction. Notably, structure-function research has implicated the AID itself in playing a critical role in channel activity, especially in terms of its effects on current inactivation.

Examination of β's structure and functional correlates has been more limited. Sequence analysis of the various genes from differing species supported a division of the protein into two central conserved motifs flanked by diverging sequences. Though it is thought that these domains interact in a stable fashion, and represent a functional core of the full-length β protein, a framework for understanding β's function in the context of the VDCC and any other possible roles is as yet, lacking.

SUMMARY OF INVENTION

In one embodiment, this invention provides a crystallized voltage-dependent calcium channel (VDCC) β subunit functional core, wherein the crystal effectively diffracts X-rays for the determination of the atomic coordinates of the voltage-dependent calcium channel β functional core to a resolution of better than 5.0 Angstroms, characterized as:
  (a) Form I of a crystallized voltage-dependent calcium channel β functional core, wherein said crystal has a space group of $P2_12_12$, with unit cell dimensions of a=34.8, b=74.1, c=163.8 Å, and α=β=γ=90°; or
  (b) Form II of a crystallized voltage-dependent calcium channel β functional core, wherein said crystal has a space group of $P4_12_12$ with unit cell dimensions of a=b=75.6, c=164.4 Å, and α=β=γ=90°.

In another embodiment, this invention provides a computer readable data storage material encoded with computer readable data comprising structure coordinates of Table 1.

In another embodiment, this invention provides a crystallized voltage-dependent calcium channel β functional core in complex with an AID peptide, wherein the AID peptide comprises the amino acid sequence corresponding to or homologous to SEQ ID NO: 22; wherein the crystal effectively diffracts X-rays for the determination of the atomic coordinates of voltage-dependent calcium channel β functional core in complex with an AID peptide to a resolution of better than 5.0 Angstroms, wherein said crystal has a space group of $P2_12_12$ with unit cell dimensions of a=77.8, b=168.3, c=34.2, Å, and α=β=γ=90°.

In another embodiment, this invention provides a method of using a crystal of this invention in an inhibitor screening assay comprising:
  (a) selecting a potential inhibitor by performing rational drug design with the three-dimensional structure determined for said crystal, wherein said selecting is performed in conjunction with computer modeling;

(b) contacting said potential inhibitor with a voltage-dependent calcium channel; and (c) detecting the ability of said potential inhibitor for inhibiting said voltage-dependent calcium channel.

In another embodiment, this invention provides a method of growing a crystallized voltage-dependent calcium channel (VDCC) β subunit functional core, comprising growing the crystal by vapor diffusion using a reservoir buffer containing 1.6 M ammonium sulfate, 0.1M Hepes, pH=7.5, and 5 mM β-mercaptoethanol, at 4° C.

In another embodiment, this invention provides a method of growing a crystallized voltage-dependent calcium channel (VDCC) β subunit functional core, comprising growing the crystal by vapor diffusion using a reservoir buffer containing 3% PEG 20,000, 0.1M Bicine, pH=9, and 100 mM NaCl, and 5 mM β-mercaptoethanol, at 19° C.

In another embodiment, this invention provides a method of growing a co-crystallized voltage-dependent calcium channel (VDCC) β subunit functional core and an AID peptide, comprising:

(a) contacting said voltage-dependent calcium channel (VDCC) β subunit functional core with an AID peptide comprising an amino acid sequence corresponding to or homologous to SEQ ID NO: 22, under conditions in which a voltage-dependent calcium channel (VDCC) β subunit functional core and AID peptide complex is formed; and (b) growing the crystal by vapor diffusion using a reservoir buffer containing 1-4% PEG 20,000; 0.1M Bicine, pH=9, and 1-3% MPD, and 5mM βmercaptoethanol, at 19° C.

In another embodiment, this invention provides a method for identifying a test compound that inhibits the interaction between a voltage-dependent calcium channel (VDCC) β subunit functional core and an AID peptide, said method comprising:

(a) contacting a voltage-dependent calcium channel (VDCC) β subunit functional core or a peptide fragment thereof comprising the binding site for an AID peptide with an AID peptide, and a test compound, under conditions and for a time sufficient to permit the formation of a complex between said voltage-dependent calcium channel (VDCC) β subunit functional core or peptide fragment thereof and said AID peptide;

(b) contacting a voltage-dependent calcium channel (VDCC) β subunit functional core or a peptide fragment thereof comprising the binding site for an AID peptide with an AID peptide, and no test compound, under conditions and for a time sufficient to permit the formation of a complex between said voltage-dependent calcium channel (VDCC) β subunit functional core or peptide fragment thereof and said AID peptide;

(c) detecting the presence of a complex in (a) versus (b), whereby a decrease or absence in the complex detected in (a) as compared to (b) indicates that the test compound inhibits the interaction between a voltage-dependent calcium channel (VDCC) β subunit functional core and an AID peptide.

According to this aspect of the invention, and in another embodiment, the binding site for an AID peptide comprises an M residue at position 246, 247 or combinations thereof. In another embodiment, the binding site for an AID peptide comprises an A residue at position 250 or an L residue at position 251, a V or L residue at position 343, an I or V residue at position 345, a K residue at position 349, a V residue at position 350, an R residue at position 353, an L or R residue at position 354, an S residue at position 357, an E residue at position 390, an N residue at position 391, an L residue at position 393, or an A residue at position 396, or combinations thereof, of the voltage-dependent calcium channel (VDCC) β subunit functional core.

In another embodiment, this invention provides an isolated polypeptide of a voltage-dependent calcium channel (VDCC) β subunit functional core comprising SH3 and guanylate kinase-like domains. According to this aspect of the invention, and in another embodiment, the polypeptide has an amino acid sequence that shares at least 90% identity with SEQ ID NO: 20 or 21. In another embodiment, the SH3 domain of the polypeptide comprises a Y residue at position 71, a W residue at position 105, or a P residue at position 121, or combinations thereof.

In another embodiment, this invention provides a method for promoting voltage-dependent calcium channel activity, comprising contacting a voltage-dependent calcium channel with an agent that initiates or enhances the physical organization of:

(a) An AID peptide; and
(b) Domain II of the β subunit of said voltage-dependent calcium channel;

whereby initiated or enhanced physical organization promotes channel activation, thereby promoting voltage-dependent calcium channel activity.

According to this aspect of the invention, and in another embodiment, the agent stimulates or increases the production of a negative electrostatic potential in Domain II of the β subunit, at a region contiguous with AID binding. In another embodiment, the β subunit changes its shape, length, rigidity, or combination thereof, in response to changes in electrostatic potential in said voltage-dependent calcium channel.

In another embodiment, this invention provides a method for inhibiting voltage-dependent calcium channel activity, comprising contacting a voltage-dependent calcium channel with an agent that interferes with the physical organization of:

(a) An AID peptide; and
(b) Domain II of the β subunit of said voltage-dependent calcium channel;

whereby interference by said agent prevents the physical organization promoting channel activation, thereby inhibiting voltage-dependent calcium channel activity.

According to this aspect of the invention, and in another embodiment, the agent interferes with production of a negative electrostatic potential in Domain II of the β subunit, at a region contiguous with AID binding, thereby inhibiting voltage-dependent calcium channel activity. In one embodiment, the agent constrains the N-terminus of said β subunit, or in another embodiment, the agent anchors said N-terminus in a cell membrane.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3 demonstrates a limited proteolyses of full-length VDCC β proteins. A: β3 was incubated with activated papain at a ratio of 3000:1 on ice in 10 mM Tris pH 8, 200 mM NaCl, 5-10 mM βME. Aliquots were taken from the reaction at the indicated times, SDS sample buffer was added, samples were boiled and analyzed later by SDS-PAGE, as shown. B: β2a incubated with activated papain and analyzed as for β3. Arrows indicate the protease resistant fragments (Opatowsky et al., 2003).

FIG. 7 demonstrates a functional assay of purified β proteins. Physiological activities of the purified proteins were examined by two-electrode voltage clamp analysis of oocytes expressing VDCC by combination of mRNA and protein injection. (A) VDCC consisted of α1.2 and β2 proteins. (B) VDCC consisted of α1.2 and β3 proteins. PB: protein buffer, Pro: Protein, DI: domain I, DI+II: domain I+domain II prepared by proteolysis of full length protein and subsequent purification (Opatowsky et al., 2003).

FIG. 10 is a photograph of rod shaped form I (A) and plate-like form II (B) crystals of voltage gated calcium channel beta subunit (fused core construct).

FIG. 11 demonstrates oscillation frames (0.5°) of form I (A) and form II (B) crystals. Diffraction data are observed to 3.4 Å and 2.3 Å, respectively FIG. 12 demonstrates a ribbon (A) and topology (B) diagram of the VDCC β subunit functional core bound to the AID peptide Domain I. Domain II and the AID are represented in red, blue and green, respectively. The topology scheme for each domain was patterned and labeled after the relevant canonical motif.

FIG. 13 depicts sequence alignments and secondary structures for the VDCC β functional core (A) and the α1 subunit I-II linker until the end of the AID sequence (B). Sequence of rabbit CCβ2a (GenBank accession number CAA45575.1) (SEQ ID NO: 23), human CCβ3 (NP_000716) (SEQ ID NO: 24) and *Anopheles gambiae* CCβAnoph (EAA12209.1) (SEQ ID NO: 25) were aligned using CLUSTALW (A). For comparison, a structure-based sequence alignment was performed with mouse c-Crk, N-terminal SH3 domain (Q64010, PDB-1CKA) (SEQ ID NO: 26), *S. cerevisiae* guanylate kinase GUK yeast, (AAB64881, KIBYGU, PDB-1GKY) (SEQ ID NO: 27) and rat PSD-95 (NP_062567, PDB-1JXO) (SEQ ID NO: 28). Secondary structure elements were assigned with DSSPcont (Andersen et al., 2002), with nomenclature and color codes as in FIG. 12B. Arrows, cylinders, and flags denote β-strands, α-helixes, and 310 helixes, respectively. Highlighted in yellow are the residues involved in poly-proline recognition in canonical SH3 domains, represented by Crk. Residues highlighted in green participate in AID/β interactions. Boxed in cyan is the NMP-binding motif of guanylate kinase, as seen for yeast GUK and PSD-95. Arg131 of yeast GUK, essential for ATP binding, is highlighted in red. (B) Alignment of the α1 subunit I-II linker until the end of the AID sequence. Accession numbers are as follows: HUMAN Cav1.1 (Q13698) (SEQ ID NO: 29), Cav1.2 (Q13936) (SEQ ID NO: 30), Cav1.3 (Q01668) (SEQ ID NO: 31), Cav1.4 (060840) (SEQ ID NO: 32), Cav2.1 (000555) (SEQ ID NO: 33), Cav2.3 (Q15878) (SEQ ID NO: 34), Cav2.1 ANOPH (EAA07643.1) (SEQ ID NO: 35), Cav2.2 (EAA07643.1) (SEQ ID NO: 36), Cav1.1 DISOC Disc.

ommata (P56698) (SEQ ID NO: 37), and Cav2.1 C.ELE *C. elegans* (AAB03158.4) (SEQ ID NO: 38).

Figure 14:
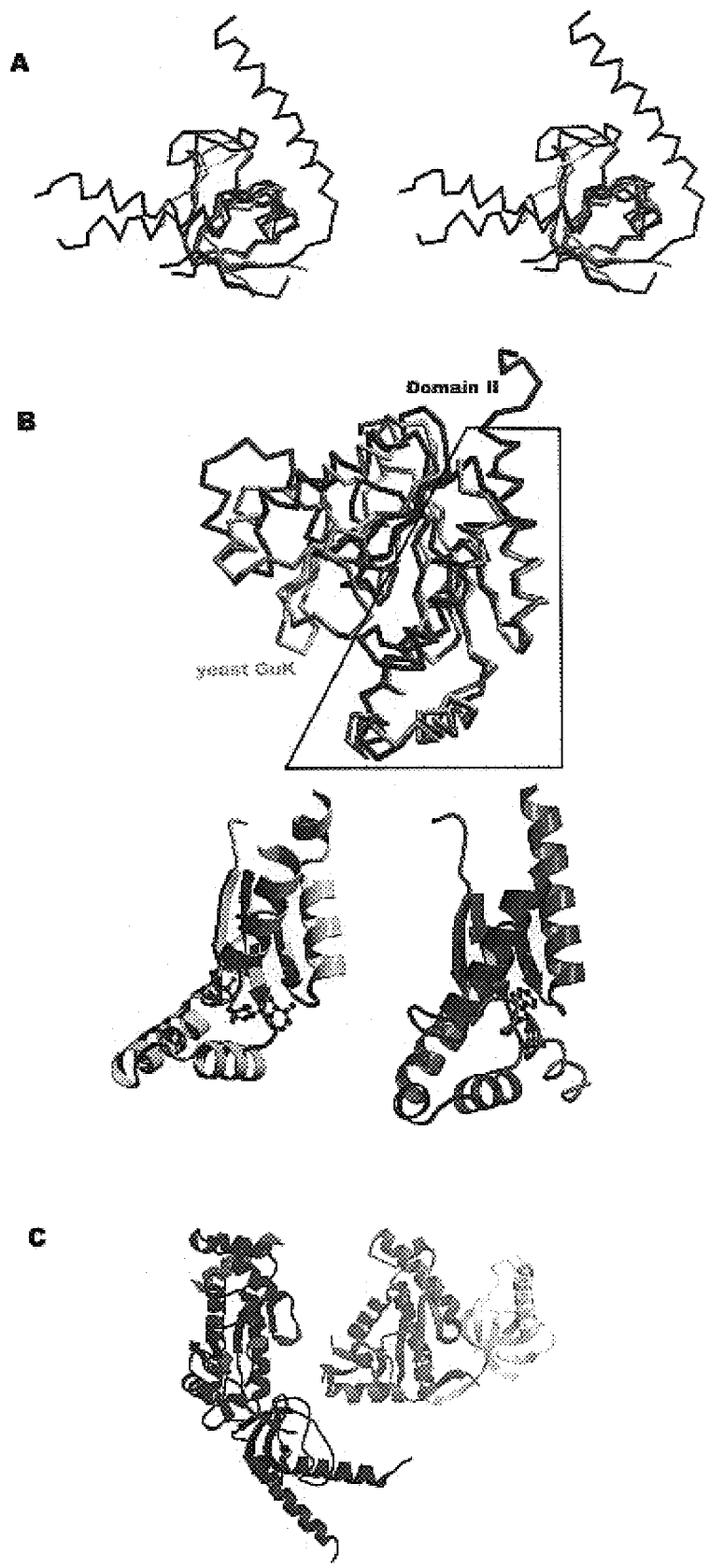

FIG. 14 is a superposition of VDCC β functional core with c-Crk, SH3 domain, GuK and PSD-95. (A) Stereo diagram of β domain I (red), superimposed with PSD-95 SH3 domain (1JXO) (blue) and c-Crk SH3 domain (1CKA) (green) with a bound proline-rich peptide (yellow). (B) β domain II (blue) superimposed with GuK (yellow). β domain II was superimposed with yeast Guk (1GKY) (top). The same perspective was used to compare the lid and core subdomains of the GuK fold from the AID-β complex and mouse GuK with bound ADP (1LVG). (bottom). (C) AID-bound β (left) and PSD-95 (right) after superposition of β domain II and the PSD GuK domain. PSD was then translated horizontally. β domain I, domain II and AID are red, blue and green, respectively, while the PSD SH3 and GuK domains are cyan and yellow, respectively.

Figure 15:

FIG. 15 demonstrates AID/β interactions. (A) 2Fo-Fc electron density map, contoured at 1σ, of the AID, calculated following molecular replacement using the β model and the AID/β complex data set. The AID (green) is represented as bonds and the β is represented in blue ribbons. (B) Closeup view of AID/β interactions with relevant side chains labeled. Dashed lines indicate hydrogen bonds. Helices 4.1 and 4.2 comprise the lid subdomain. (C) Table of AID mutations abstracted from the literature (Berrou et al., 2002; De Waard et al., 1996; Witcher et al., 1995). Binding to β is the effect charted on a scale of no binding (−) to WT binding (4 stars).

Figure 16:
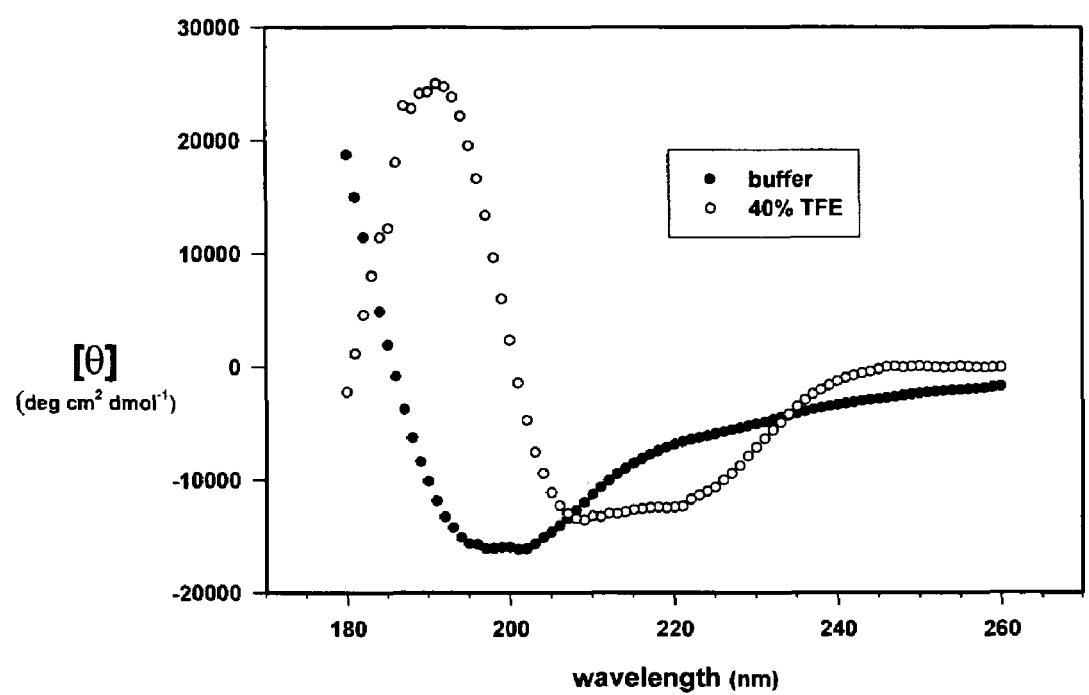

FIG. 16 demonstrates results of CD Spectroscopy of the AID peptide in solution. Spectra were measured in 2.5 mM Na phosphate pH=8, 15 mM NaCl (filled circles) at a peptide concentration of 46 μM at 20° C., and in 40% (vol/vol) trifluorethanol plus the above buffer (open circles). Deconvolution analysis (Bohm et al., 1992) indicate 9% helicity in buffer alone versus about 34% in the TFE solution.

FIG. 17 demonstrates structural features of VDCC β. (A) Proposed model for β localization, in respect to the α1 pore-forming unit. β is represented in a molecular surface form, domain I and domain II are red and blue, respectively. The I-II linker from S6 through the AID was built as a helix and is colored in green. (B) Electrostatic potential representation of the AID/β complex, projected onto its molecular surface. Potential was calculated at 0.1 M ionic strength. The corresponding worm representations are shown, where domain I, domain II and AID are red, blue and green, respectively. Note the negative patch in the proximity of the AID binding site.

DETAILED DESCRIPTION OF THE INVENTION

The present invention provides, in one embodiment crystallized voltage-dependent calcium channel β subunit functional cores, and methods of producing the same. This invention provides, in another embodiment, an isolated polypeptide of a voltage-dependent calcium channel (VDCC) β subunit functional core comprising SH3 and guanylate kinase-like domains. In another embodiment, this invention provides methods of regulating voltage-dependent calcium channels.

Calcium channels are membrane-spanning, multi-subunit proteins that allow controlled entry of Ca2+ ions into cells from the extracellular fluid. The most common type of calcium channel is voltage dependent. All "excitable" cells in animals, such as neurons of the central nervous system (CNS), peripheral nerve cells and muscle cells, including those of skeletal muscles, cardiac muscles, and venous and arterial smooth muscles, have voltage-dependent calcium channels.

Voltage dependent calcium channels allow for influx of Ca2+ ions into a cell, and require a depolarization to a certain level of the potential difference between the inside of the cell bearing the channel and the extracellular environment bathing the cell.

Calcium channels are present in various tissues and have a central role in regulating intracellular calcium ion concentrations, and are implicated in a number of vital processes in animals, including neurotransmitter release, muscle contraction, pacemaker activity, and secretion of hormones and other substances. These processes, are involved in numerous human disorders, such as CNS and cardiovascular diseases and therefore, methods of modulating functions of voltage-dependent calcium channels, which, in another embodiment, are provided in the present invention, may be utilized for treating, or alleviating symptoms of such human disorder, as will be described further, hereinbelow.

The VDCC comprises four distinct polypeptides: α1, α2d, β and γ. The β subunit interacts with the α subunit, and acts by both chaperoning VDCCs to the membrane and modulating gating of the channel.

This invention demonstrates, in one embodiment, that the β subunit is comprised of two motifs, which are homologous to the SH3 and the guanylate kinase families, respectively, and serve as a minimal requisite for MAGUK family members. The two domains were shown herein to interact in a stable fashion, and represent, in one embodiment, a functional core of the full-length β protein.

In one embodiment, the VDCC β subunit has a sequence such as that disclosed in Genbank Accession Number: AAH41811, AAH26479, AAQ97611, AAQ97610, AAQ97609, AAQ97608, AAQ97607, AAQ97606, AAQ97605, NP_666235, NP_000716, NP_000717, NP_660099, NP_446303, NP_059042, O00305, Q9Y698, P54284, Q08289, Q02641, Q9MZL7, Q9MZL5, Q9MZL3, AAL16951, AAL16950, AAL16949, AAL16948, I65767, I65766, I52859, I52859, P54288_2, or BAA07803.

Crystallographic analysis was conducted herein, of the VDCC β subunit functional core alone and in complex with an AID peptide. Three crystal forms were produced, as described hereinbelow.

In one embodiment, this invention provides a crystallized voltage-dependent calcium channel (VDCC) β subunit functional core, wherein the crystal effectively diffracts X-rays for the determination of the atomic coordinates of the voltage-dependent calcium channel β functional core to a resolution of better than 5.0 Angstroms. In one embodiment, the crystallized voltage-dependent calcium channel (VDCC) β subunit functional core is characterized as having a space group of $P2_12_12$, with unit cell dimensions of a=34.8, b=74.1, c=163.8 Å, and α=β=γ=90°.

In another embodiment, the crystallized voltage-dependent calcium channel (VDCC) β subunit functional core is characterized as having a space group of $P4_12_12$ with unit cell dimensions of a=b=75.6, c=164.4 Å, and α=β=γ=90°.

In another embodiment, this invention provides a computer readable data storage material encoded with computer readable data comprising structure coordinates of Table 1.

In another embodiment, this invention provides a crystallized voltage-dependent calcium channel β functional core in complex with an AID peptide, wherein the crystal effectively diffracts X-rays for the determination of the atomic coordinates of voltage-dependent calcium channel β functional core in complex with an AID peptide to a resolution of better than 5.0 Angstroms. In one embodiment, the crystallized voltage-dependent calcium channel β functional core in complex with an AID peptide core is characterized as having a space group of $P2_12_12$ with unit cell dimensions of a=72.8, b=168.3, c=34.2 Å, and α=β=γ=90°. In another embodiment, the AID peptide comprises the amino acid sequence corresponding to or homologous to QQLEEDLRGYMSWITQGE (SEQ ID NO: 22). In one embodiment, the AID peptide may comprise a substitution of A for Q at positions 1, 2 or combination thereof of SEQ ID NO: 22. In another embodiment, the AID peptide may comprise a substitution of S, D or R for an E at positions 4, 5 or combination thereof of SEQ ID NO: 22. In another embodiment, the AID may comprise a combination of any substitution described or exemplified herein.

In one embodiment, the AID peptide is as disclosed in Genbank Accession Numbers Q13698, Q13936, Q01668, O60840, O00555, Q15878, EAA07643.1, EAA07643.1, P56698, or AAB03158.4.

The structures of the voltage-dependent calcium channel (VDCC) β subunit functional core of the invention provide especially meaningful guidance for the development of drugs to target and promote or inhibit its interaction with alpha subunits, which would serve to regulate VDCC activity. Because calcium channels have a central role in regulating intracellular calcium ion concentrations, they play a role in a number of human disorders, such as CNS and cardiovascular diseases. Compounds useful for treating various cardiovascular diseases exert their beneficial effects, in one embodiment, by modulating functions of voltage-dependent calcium channels present in cardiac and/or vascular smooth muscle. In one embodiment, these compounds bind to calcium channels and block, or reduce the rate of, influx of Ca2+ into the cells in response to depolarization of the cell membrane. The identification of such inhibitors has important clinical application, and can be accomplished, in one embodiment, via the methods of this invention.

The three dimensional structures provided in an embodiment of this invention, allow an understanding of the interactions between the α and β subunits of the VDCC, which enables those of ordinary skill in the art to utilize rational mechanism-based and structure-based drug design technology to develop specific agents which promote, and/or inhibit VDCC activity, for use as novel drugs. The design of such agents may be accomplished in one embodiment, using molecular modeling, which may have important clinically therapeutic capabilities.

Crystallization of the β2α functional core provided for the generation of experimental electron density maps at 2.9 Å resolution, in one aspect of this invention, which enabled tracing of the complete molecule with two clearly defined domains. Refinement of the atomic model continued with a 2.3 Å data set. Diffraction data to 3.5 Å was obtained for an alternate crystal form, crystallized with two different forms of the functional core protein. Subsequent, co-crystallization of the β functional core with the CaV1.1 AID yielded diffraction data measured to a dmin of 2.2 Å. The structure revealed a two-domain construction, with dimensions 94×54×48 Å, and defined a new variant of the membrane associated guanylate kinase (MAGUK) protein family, which function as molecular scaffolds, using their various domains to create a web of protein-protein interactions at or near the cell membrane.

Structural analysis provided an understanding of how the two domains interact. Strand E of domain I is covalently linked by a short four residue turn to domain II, and in addition, other interactions include hydrogen bonds from domain II helix 5 made with the distal loop of domain I. Side chains from the ear lobe and a turn before strand 4 of domain II interact with strand E of domain I. The domain interface in β is buried much of its accessible surface area (1500 Å2).

The AID forms an α-helix that nestles into a groove on the protein, shaped by the juxtaposition of the lid subdomain and the core subdomain P-loop, helix 1, strand 5 and helix 5, and has two legs stapling it down in the groove. One leg consists of W369 and I370. W369 binds in a deep pit on the domain II surface and makes many interactions with domain II residues. The second leg consists of G365 and Y366. Y366 is buried completely, making van der Waals interactions with β. Concomitantly, its hydroxyl group makes bifurcated hydrogen-bonds to two water molecules. These, in turn, mediate hydrogen-bonds to β main chain carbonyl (389) or amine (345) groups. The balance of connections involve van der Waals or hydrophobic interactions. Importantly, interactions between AID and domain II are not localized to one region in sequence space of β. Three regions in sequence space contribute to the AID binding site, so that for proper binding of the AID, one requires almost the complete domain II.

The structure coordinates provided may also be used to solve the structure of VDCC β subunit functional core mutants, co-complexes with the same, or of the crystalline form of any other protein with significant amino acid sequence homology thereof.

One embodiment for a method that may be employed for such purposes is molecular replacement. In this method, the unknown crystal structure may be determined using the VDCC β subunit functional core structure coordinates of this invention.

In one embodiment, the term "molecular replacement" refers to a method that involves generating a preliminary model of a crystal of, in one embodiment, a channel protein, whose structure coordinates are unknown, by orienting and positioning a molecule whose structure coordinates are known, such as the VDCC β subunit functional core coordinates, within the unit cell of the unknown crystal so as best to account for the observed diffraction pattern of the unknown crystal. Phases can then be calculated from this model and combined with the observed amplitudes to give an approximate Fourier synthesis of the structure whose coordinates are unknown. This, in turn, can be subject to any of the several forms of refinement to provide a final, accurate structure of the unknown crystal, as is known by those of ordinary skill in the art. Using the structure coordinates of VDCC β subunit functional core provided by this invention, molecular replacement can thus be used to determine the structure coordinates of, in other embodiments, a crystalline mutant or homologue of VDCC β subunit functional core, or additional crystal forms of VDCC β subunit functional core.

In another embodiment, this invention provides a method of using a crystal of this invention in an inhibitor screening assay comprising:
  (a) selecting a potential inhibitor by performing rational drug design with the three-dimensional structure determined for said crystal, wherein said selecting is performed in conjunction with computer modeling;
  (b) contacting said potential inhibitor with a voltage-dependent calcium channel; and
  (c) detecting the ability of said potential inhibitor for inhibiting said voltage-dependent calcium channel.

In one embodiment, the potential inhibitor is contacted with a VDCC β subunit functional core.

In another embodiment, this invention provides a method for identifying a test compound that inhibits the interaction between a voltage-dependent calcium channel (VDCC) β subunit and an AID peptide, said method comprising:
  (a) contacting a voltage-dependent calcium channel (VDCC) β subunit or a fragment thereof comprising the binding site for an AID peptide with an AID peptide, and a test compound, under conditions and for a time sufficient to permit the formation of a complex between said voltage-dependent calcium channel (VDCC) β subunit functional core or peptide fragment thereof and said AID peptide;

(b) contacting a voltage-dependent calcium channel (VDCC) β subunit functional core or a peptide fragment thereof comprising the binding site for an AID peptide with an AID peptide, and no test compound, under conditions and for a time sufficient to permit the formation of a complex between said voltage-dependent calcium channel (VDCC) β subunit functional core or peptide fragment thereof and said AID peptide;

(c) detecting the presence of a complex in (a) versus (b), whereby a decrease or absence in the complex detected in (a) as compared to (b) indicates that the test compound inhibits the interaction between a voltage-dependent calcium channel (VDCC) β subunit functional core and an AID peptide.

According to this aspect of the invention, and in another embodiment, the binding site for an AID peptide comprises an M residue at position 246, 247 or combinations thereof. In another embodiment, the binding site for an AID peptide comprises an A residue at position 250 or an L residue at position 251, a V or L residue at position 343, an I or V residue at position 345, a K residue at position 349, a V residue at position 350, an R residue at position 353, an L or R residue at position 354, an S residue at position 357, an E residue at position 390, an N residue at position 391, an L residue at position 393, or an A residue at position 396, or combinations thereof, of the voltage-dependent calcium channel (VDCC) β subunit.

In another embodiment, according to this aspect of the invention, the method employs contacting the agent with a VDCC β subunit functional core.

In another embodiment, this invention provides a method for identifying a test compound that promotes the interaction between a voltage-dependent calcium channel (VDCC) β subunit and an AID peptide, said method comprising:

(a) contacting a voltage-dependent calcium channel (VDCC) β subunit or a fragment thereof comprising the binding site for an AID peptide with an AID peptide, and a test compound, under conditions and for a time sufficient to permit the formation of a complex between said voltage-dependent calcium channel (VDCC) β subunit or peptide fragment thereof and said AID peptide;

(b) contacting a voltage-dependent calcium channel (VDCC) β subunit or a peptide fragment thereof comprising the binding site for an AID peptide with an AID peptide, and no test compound, under conditions and for a time sufficient to permit the formation of a complex between said voltage-dependent calcium channel (VDCC) β subunit or peptide fragment thereof and said AID peptide;

(c) detecting the presence of a complex in (a) versus (b), whereby an increase in the amount of complex detected in (a) as compared to (b), or an increase in the binding affinity of said AID peptide for said VDCC β subunit in (a) as compared to (b) indicates that the test compound promotes the interaction between a voltage-dependent calcium channel (VDCC) β subunit functional core and an AID peptide.

According to this aspect of the invention, and in another embodiment, the binding site for an AID peptide comprises residues as indicated hereinabove. In another embodiment, according to this aspect of the invention, the method employs contacting the agent with a VDCC β subunit functional core.

Numerous computer programs are available and suitable for rational drug design and the processes of computer modeling, model building, and computationally identifying, selecting and evaluating potential inhibitors and promoters of VDCC α and β association in the methods described herein. These include, for example, GRID (available form Oxford University, UK), MCSS (available from Molecular Simulations Inc., Burlington, Mass.), AUTODOCK (available from Oxford Molecular Group), FLEX X (available from Tripos, St. Louis. Mo.), DOCK (available from University of California, San Francisco), CAVEAT (available from University of California, Berkeley), HOOK (available from Molecular Simulations Inc., Burlington, Mass.), and 3D database systems such as MACCS-3D (available from MDL Information Systems, San Leandro, Calif.), and UNITY (available from Tripos, St. Louis. Mo. Potential agents may also be computationally designed "de novo" using such software packages as LUDI (available from Biosym Technologies, San Diego, Calif.), LEGEND (available from Molecular Simulations Inc., Burlington, Mass.), and LEAPFROG (Tripos Associates, St. Louis, Mo.). Compound deformation energy and electrostatic repulsion, may be evaluated using programs such as GAUSSIAN 92, AMBER, QUANTA/CHARMM, AND INSIGHT II/DISCOVER. These computer evaluation and modeling techniques may be performed on any suitable hardware including for example, workstations available from Silicon Graphics, Sun Microsystems, and the like. These techniques, methods, hardware and software packages are representative and are not intended to be comprehensive listing. Other modeling techniques known in the art may also be employed in accordance with this invention. See for example, N. C. Cohen, Molecular Modeling in Drug Design, Academic Press (1996) (and references therein), and software identified at internet sites including the CAOS/CAMM Center Cheminformatics Suite at www.caos.kun.nl/, and the NIH Molecular Modeling Home Page at www.fi.muni.cz/usr/mejzlik/mirrors/molbio.info.nih.gov/modeling/software list/.

The agent is selected by performing rational drug design with the three-dimensional structure (or structures) determined for the crystal described herein, especially in conjunction with computer modeling and methods described above. The agent is then obtained from commercial sources or is synthesized from readily available starting materials using standard synthetic techniques and methodologies known to those of ordinary skill in the art. The agent is then assayed, in one embodiment, to determine its ability to promote or inhibit α and β association, or, in another embodiment, VDCC channel activity, by methods well known in the art, or, in another embodiment, as exemplified herein.

The agent selected or identified by the aforementioned process may be assayed to determine its ability to affect VDCC channel activity, in one embodiment. The assay may be in vitro or in vivo. The compounds described herein may be used in assays, including radiolabelled, antibody detection and fluorometric, in another embodiment, for the isolation, identification, or structural or functional characterization of VDCC. Such assays may include, in another embodiment, an assay, utilizing a full length VDCC, which, in another embodiment, is contacted with the agent and a measurement of the binding affinity of the agent against a standard is determined.

In one embodiment, the assay is performed as exemplified herein in Example 1. The assay may, according to this aspect of the invention, employ fluorescence polarization measurements. Agents, such as, in one embodiment, peptides which are expected to bind to the VDCC β subunit functional core are labeled with fluorescein. Labeled agent/peptide is then titrated with increasing concentrations of β, and the fluorescence polarization emitted by the labeled agent/peptide is determined. Fluorescence emission polarization is proportional to the rotational correlation time (tumbling) of the labeled molecule. Tumbling, in part, depends on the molecular volume, i.e. larger molecules have larger volume and slower tumbling which in turn gives rise to increased polarization of emitted light. If the agent/peptide associates with β, its effective molecular volume greatly increases, which may be evidenced by values obtained for polarization fluorescence emissions.

In other embodiments, electrophysiological methods for measuring calcium channel activity, which are known to those of skill in the art and exemplified herein may be utilized for the indicated purposes. Any such methods may be used in order to detect the formation of functional calcium channels and to characterize the kinetics and other characteristics of the resulting currents. Pharmacological studies may be combined with the electrophysiological measurements, in other embodiments, in order to further characterize the calcium channels In one embodiment, complexes of peptides/agents with the VDCC β subunit may be studied using well-known X-ray diffraction techniques, and as exemplified herein, in another embodiment, and may be refined versus 2-3 angstrom resolution X-ray data to an R value of about 0.20 or less using readily available computer software, such as X-PLOR (Yale University©, 1992, distributed by Molecular Simulations, Inc.; Blundel & Johnson, 1985, specifically incorporated herein by reference).

The design of compounds that promote or inhibit VDCC α and β subunit interaction and channel activity, according to this invention may involve, in another embodiment, several considerations. In one embodiment, the compound should be capable of physically and structurally associating with the β subunit, such as, in other embodiments, by using non-covalent molecular interactions, including hydrogen bonding, van der Waals and hydrophobic interactions and the like. Second, the compound should be able to assume a conformation that allows it to associate with the VDCC β subunit. Although certain portions of the compound will not directly participate in this association with the VDCC β subunit, those portions may still influence the overall conformation of the molecule. This, in turn, may have a significant impact on potency. Such conformational requirements include the overall three-dimensional structure and orientation of the chemical entity or compound in relation to all or a portion of the binding site, e.g., AID binding site with the VDCC β subunit.

The potential inhibitory or promotional effect of a chemical compound on the VDCC α and β subunit interaction and VDCC activity may be analyzed prior to its actual synthesis and testing by the use of computer modeling techniques, as is known to those of ordinary skill in the art.

One of ordinary skill in the art may use, in other embodiments of this invention, any one of several methods to screen chemical entities or fragments for their ability to associate with the VDCC β subunit, and, in another embodiment, with the AID binding site of the VDCC β subunit. This process may begin by visual inspection of, for example, the AID binding site of the VDCC β subunit on the computer screen based on data presented in, for example, FIG. 15. Selected fragments or chemical entities may then be positioned in a variety of orientations, or docked, within the AID binding site of the VDCC β subunit. Docking may be accomplished using software such as Quanta and Sybyl, followed by energy minimization and molecular dynamics with standard molecular mechanics forcefields, such as CHARMM and AMBER.

Specialized computer programs may also assist in the process of selecting fragments or chemical entities. These include, in one embodiment, the programs GRID, MCSS, AUTODOCK and DOCK.

Once suitable chemical entities or fragments have been selected, they may, in another embodiment, be assembled into a single compound. Assembly may be preceded by visual inspection of the relationship of the fragments to each other on the three-dimensional image displayed on a computer screen in relation to the structure coordinates of VDCC. This may be followed, in another embodiment, by manual model building using software such as Quanta or Sybyl.

Useful programs to aid one of skill in the art in connecting the individual chemical entities or fragments include, in other embodiments, CAVEAT, 3D Database systems such as MACCS-3D (MDL Information Systems, San Leandro, Calif.) and HOOK.

In another embodiment, instead of proceeding to build an agent which interacts with the VDCC β subunit in a step-wise fashion, one fragment or chemical entity at a time as described above, the agent may be designed as a whole or "de novo" using an empty binding site. These methods may include the use of programs such as LUDI, LEGEND and LeapFrog, each of which represents an embodiment of this invention.

In another embodiment, once a compound has been designed or selected by the above methods, the efficiency with which that compound may bind to the VDCC β subunit may be tested and optimized by computational evaluation. In such methods, the deformation energy of binding may be considered and agents, which interact with the VDCC β subunit, may be designed with a particular deformation energy of binding, as will be understood by one of ordinary skill in the art.

A compound designed or selected as binding to the VDCC β subunit may, in another embodiment, be further computationally optimized so that in its bound state it would preferably lack repulsive electrostatic interaction with the VDCC β subunit. Such non-complementary (e.g., electrostatic) interactions include, in other embodiments, repulsive charge-charge, dipole-dipole and charge-dipole interactions. Specifically, the sum of all electrostatic interactions between the bound agent and the VDCC β subunit, make, in another embodiment, a neutral or favorable contribution to the enthalpy of binding.

Specific computer software is available in the art to evaluate compound deformation energy and electrostatic interaction, and may include, in other embodiments, Gaussian 92, revision C (Frisch, Gaussian, Inc., Pittsburgh, Pa.,© 1992); AMBER, version 4.0 (Kollman, University of California at San Francisco, © 1994); QUANTA/CHARMM (Molecular Simulations, Inc., Burlington, Mass., 1994); or Insight II/Discover (Biosysm Teclnologies Inc., San Diego, Calif., © 1994).

In another embodiment, once an agent binding to a VDCC β subunit has been optimally selected or designed, as described above, substitutions may then be made in some of its atoms or side groups in order to improve or modify its binding properties. In one embodiment, initial substitutions are conservative, i.e., the replacement group will have approximately the same size, shape, hydrophobicity and charge as the original group. Such substituted chemical compounds may then be, in another embodiment, analyzed for efficiency of fit to the VDCC β subunit by the same computer methods described in detail, above.

In another embodiment, this invention provides a method for promoting voltage-dependent calcium channel activity, comprising contacting a voltage-dependent calcium channel with an agent that initiates or enhances the physical organization of:
(a) An AID peptide; and
(b) Domain II of the β subunit of said voltage-dependent calcium channel;

whereby initiated or enhanced physical organization promotes channel activation, thereby promoting voltage-dependent calcium channel activity.

According to this aspect of the invention, and in another embodiment, the agent stimulates or increases the production of a negative electrostatic potential in Domain II of the β subunit, at a region contiguous with AID binding. In another embodiment, the β subunit changes its shape, length, rigidity, or combination thereof, in response to changes in electrostatic potential in said voltage-dependent calcium channel.

The AID-β complex structure has been demonstrated herein to have AID and β almost seamlessly fuse into a united surface. The resulting electrostatic potential produced shows that β domain II has a patch of negative potential, coincident and contiguous to the locale of AID binding, which reacts to changes in the electrostatic potential of the surrounding environment as a result of membrane depolarization and the channel opening with its flux of Ca2+ ions diffusing from the channel mouth. Hence, the bound β reconfigures the electrostatics of the intracellular side of the channel.

In one embodiment, β orders a part of the channel physically connected to its gate, essentially changing its shape, or, in other embodiments, length, mechanical properties, such as rigidity, or a combination thereof.

In another embodiment of this invention, through β binding, the gate is now connected to a linker with much greater mass and depending on isoform constrained in its movement by its own independent attachment to the membrane.

Upon depolarization, the I-II linker/β negative patch may move in reaction to the changing electrostatic potential of α1, supplementing the radial torque on S6 from the voltage sensor. The presumed helical conformation will lend the requisite rigidity for any movements of the AID-β particle to be communicated to the gate. Also, the additional mass weighing on membrane domain I may destabilize the closed conformation of its S6. Thus, β's action on the channel state may be categorized, in another embodiment of this invention, as allosteric modulation.

Agents may be specifically designed, via methodology described hereinabove, to initiate or enhance the physical organization of the channel. In one embodiment, the agent promotes for greater or prolonged binding between β and the AID. In another embodiment, the agent promotes the generation of a greater or prolonged accumulation of a negative potential in β domain II, to promote channel opening. The design of such agents will be well known to one skilled in the art, and may comprise mutated β proteins, and other agents that achieve the desired result.

In one embodiment, the methods for promotion of VDCC activity may find clinical application in the treatment of Lambert-Eaton myasthenic syndrome (LEMS) seen in some small cell lung cancer patients. LEMS is a human autoimmune disorder that impairs neuromuscular transmission such that patients with this syndrome have a defect in the Ca2+ dependent quantal release of acetylcholine from motor nerve terminals. In this syndrome, patients develop antibodies (presumably initiated by expression of the channel proteins in their small cell lung cancer) that react with voltage-gated calcium channel polypeptides which block depolarization-induced Ca2+ influx leading to the myasthenia. The methods/agents proposed in this invention may serve, according to this aspect, to promote appropriate physical organization, and/or inhibit antibody binding, in the case of LEMS, such that proper VDCC activity occurs.

In another embodiment, this invention provides a method for inhibiting voltage-dependent calcium channel activity, comprising contacting a voltage-dependent calcium channel with an agent that interferes with the physical organization of:
(a) An AID peptide; and
(b) Domain II of the β subunit of said voltage-dependent calcium channel;

whereby interference by said agent prevents the physical organization promoting channel activation, thereby inhibiting voltage-dependent calcium channel activity.

According to this aspect of the invention, and in another embodiment, the agent interferes with production of a negative electrostatic potential in Domain II of the β subunit, at a region contiguous with AID binding, thereby inhibiting voltage-dependent calcium channel activity. In one embodiment, the agent constrains the N-terminus of said β subunit, or in another embodiment, agent anchors said N-terminus in a cell membrane. In another embodiment, the agent provides steric hindrace such that the physical organization is diminished or absent. According to this aspect of the invention, the agent may be an antibody.

According to this aspect of the invention, and in one embodiment, channel inactivation may be via a hinged-lid mechanism, wherein the AID/β surface serves as the lid, the channel opens, Ca2+ accumulates at the mouth, and attracts the lid by Coulombic forces and in coordination with Ca2+-dependent inactivation determinants of the α1 C-terminus.

Subsequently, residues in the AID that are solvent exposed i.e. those not involved in binding β and other residues of the linker find their receptor site possibly in the channel mouth, thereby blocking ion flow and inactivating the channel. According to this inactivation mechanism, the hinge, which enables the lid to swivel may be located at the link between S6 and the I-II linker i.e. the conserved glycine sequence at its start, and agents targeting this region may be involved, in one embodiment, in regulating VDCC channel function In another embodiment, the slowing or inactivation of β's movement may be constrained through its N-terminus, since, according to this aspect of the invention, the "lid" would then not be able to move as easily towards the channel mouth. This notion then explains the slow inactivation of β2a, whose N-terminus is anchored in the membrane by palmitoylation. When the palmitoylation site is mutated, inactivation parameters resemble that of the other isoforms and splice variants.

In one embodiment, the methods of this invention, wherein blocking calcium transport would be of therapeutic value, which may be accomplished via the methods of this invention, may include osteosclerosis, stroke, head trauma, epilepsy, and chronic, neuropathic and acute pain. Calcium transport, especially that associated with N-type channels, is also implicated in other neurological disorders such as migraine, epilepsy, mood disorders, schizophrenia, and certain degenerative disorders. Other conditions that benefit from reduced calcium flux include depression, anxiety, and other psychoses. Cardiovascular conditions benefited include hypertension and cardiac arrhythmias. In another embodiment, inactivation of VDCC's may be beneficial in applications in developing pesticides.

In certain embodiments, the assays for identifying compounds that modulate calcium channel activity are practiced by measuring the calcium channel activity of a eukaryotic cell having a heterologous, functional calcium channel when such cell is exposed to a solution containing the test compound and a calcium channel selective ion and comparing the measured calcium channel activity to the calcium channel activity of the same cell or a substantially identical control cell in a solution not containing the test compound. The cell is maintained, in one embodiment, in a solution having a concentration of calcium channel selective ions sufficient to provide an inward current when the channels open. Methods for practicing such assays are known to those of skill in the art. For example, for similar methods applied with *Xenopus laevis* oocytes and acetylcholine receptors, see, Mishina et al. [(1985) Nature 313:364] and, with such ooocytes and sodium channels [see, Noda et al. (1986) Nature 322:826-828]; For similar studies which have been carried out with the acetylcholine receptor, see, e.g., Claudio et al. [(1987) Science 238:1688-1694].

The assays thus use cells that express functional calcium channels and measure functionally, such as electrophysiologically, the ability of a test compound to potentiate, antagonize or otherwise modulate the magnitude and duration of the flow of calcium channel selective ions, such as Ca++ or Ba++, through the heterologous functional channel. The amount of current, which flows through the recombinant calcium channels of a cell may be determined, in one embodiment, directly, such as electrophysiologically, or, in another embodiment, by monitoring an independent reaction which occurs intracellularly and which is directly influenced in a calcium (or other) ion dependent manner.

Any method for assessing the activity of a calcium channel may be used in conjunction with the methods described herein. For example, in one embodiment of the method for testing a compound for its ability to modulate calcium channel activity, the amount of current is measured by its modulation of a reaction which is sensitive to calcium channel selective ions and uses a eukaryotic cell which expresses a heterologous calcium channel and also contains a transcriptional control element operatively linked for expression to a structural gene that encodes an indicator protein. The transcriptional control element used for transcription of the indicator gene is responsive in the cell to a calcium channel selective ion, such as Ca2+ and Ba2+. The details of such transcriptional based assays are described, for example, in PCT International Patent Application No. PCT/US91/5625.

In another embodiment, this invention provides a method of growing a crystallized voltage-dependent calcium channel (VDCC) β subunit functional core, comprising growing the crystal by vapor diffusion using a reservoir buffer containing 1.6 M ammonium sulfate, 0.1M Hepes, pH=7.5, and 5 mM β-mercaptoethanol, at 4° C.

In another embodiment, this invention provides a method of growing a crystallized voltage-dependent calcium channel (VDCC) β subunit functional core, comprising growing the crystal by vapor diffusion using a reservoir buffer containing 3% PEG 20,000, 0.1M Bicine, pH=9, and 100 mM NaCl, and 5 mM β-mercaptoethanol, at 19° C.

In another embodiment, this invention provides a method of growing a co-crystallized voltage-dependent calcium channel (VDCC) β subunit functional core and an AID peptide, comprising:
  (a) contacting said voltage-dependent calcium channel (VDCC) β subunit functional core with an AID peptide comprising an amino acid sequence corresponding to SEQ ID NO: 22, under conditions in which a voltage-dependent calcium channel (VDCC) β subunit functional core and AID peptide complex is formed; and
  (b) growing the crystal by vapor diffusion using a reservoir buffer containing 1-4% PEG 20,000; 0.1M Bicine, pH=9, and 1-3% MPD, and 5 mM β-mercaptoethanol, at 19° C.

In another embodiment, this invention provides an isolated polypeptide of a voltage-dependent calcium channel (VDCC) β subunit functional core comprising SH3 and guanylate kinase-like domains. In one embodiment, the polypeptide will have an amino acid sequence, which corresponds to, or is homologous to SEQ ID NO: 20 or 21.

In one embodiment, the polypeptides of this invention include, but are not limited to, fragments of native polypeptides from any animal species (including as humans), and derivatives of native (human and non-human) polypeptides and their fragments, provided that they have a biological activity in common with a respective native polypeptide. "Fragments" comprise, in one embodiment, regions within the sequence of a mature native polypeptide. The term "derived" is meant to include, in another embodiment, amino acid sequence and glycosylation variants, and covalent modifications of a native polypeptide, whereas the term "variant" refers to amino acid sequence and glycosylation variants within this definition VDCC β subunit functional core-derived peptides include all peptides having a qualitative biological activity in common with a native VDCC β subunit functional core, comprising both SH3 and guanylate kinase-like domains, or in another embodiment, their consensus sequences, and may, according to additional embodiments of the invention, comprise the entire consensus sequence, or a polypeptide fragment thereof.

The term "peptide", when in reference to any peptide of this invention, is meant to include, in other embodiments, native peptides (either, degradation products, synthetically synthesized peptides or recombinant peptides) and peptidomimetics (typically, synthetically synthesized peptides), such as peptoids and semipeptoids which are peptide analogs, which may have, for example, modifications rendering the peptides more stable while in a body or more capable of penetrating into cells. Such modifications include, but are not limited to N terminal, C terminal or peptide bond modification, including, but not limited to, backbone modifications, and residue modification, each of which represents an additional embodiment of the invention. Methods for preparing peptidomimetic compounds are well known in the art and are specified, for example, in Quantitative Drug Design, C. A. Ramsden Gd., Chapter 17.2, F. Choplin Pergamon Press (1992).

It is to be understood that any VDCC β subunit functional core-derived peptide of the present invention may be isolated, generated synthetically, obtained via translation of sequences subjected to any mutagenesis technique, as well as obtained via protein evolution techniques, well known to those skilled in the art.

In one embodiment, the VDCC β subunit functional core-derived peptide of the present invention may be employed in the following applications: 1) screening assays; 2) predictive medicine (e.g., diagnostic assays, prognostic assays, monitoring clinical trials, and pharmacogenetics); and 3) methods of treatment (e.g., therapeutic and prophylactic), as has been described hereinabove.

In one embodiment, the terms "homology", "homologue" or "homologous", refer to an amino acid sequence, which exhibits, in one embodiment at least 70% correspondence with the indicated sequence. In another embodiment, the amino acid sequence exhibits at least 72% correspondence with the indicated sequence. In another embodiment, the amino acid sequence exhibits at least 75% correspondence with the indicated sequence. In another embodiment, the amino acid sequence exhibits at least 80% correspondence with the indicated sequence. In another embodiment, the amino acid sequence exhibits at least 82% correspondence with the indicated sequence. In another embodiment, the amino acid sequence exhibits at least 85% correspondence with the indicated sequence. In another embodiment, the amino acid sequence exhibits at least 87% correspondence with the indicated sequence. In another embodiment, the amino acid sequence exhibits at least 90% correspondence with the indicated sequence. In another embodiment, the amino acid sequence exhibits at least 92% correspondence with the indicated sequence. In another embodiment, the amino acid sequence exhibits at least 95% or more correspondence with the indicated sequence. In another embodiment, the amino acid sequence exhibits at least 97% correspondence with the indicated sequence. In another embodiment, the amino acid sequence exhibits at least 99% correspondence with the indicated sequence. In another embodiment, the amino acid sequence exhibits 95%-100% correspondence with the indicated sequence. Similarly, as used herein, the reference to a correspondence to a particular sequence includes both direct correspondence, as well as homology to that sequence as herein defined.

Homology, as used herein, may refer to sequence identity, or may refer to structural identity, or functional identity. By using the term "homology" and other like forms, it is to be understood that any molecule, that functions similarly, and/or contains sequence identity, and/or is conserved structurally so that it approximates the reference sequence, is to be considered as part of this invention.

According to this aspect of the invention, and in another embodiment, the SH3 domain comprises a Y residue at position 71, a W residue at position 105, or a P residue at position 121, or combinations thereof.

In one embodiment, the molecular architecture of the β functional core supports, and in another embodiment, maximizes protein-protein interactions with other proteins. Proteins that associate with β may comprise, in one embodiment, members of the small G-protein subfamily, Gem, Rad, and Rem and HP1g, involved in gene silencing. According to this aspect of the invenion, β may serve as a nexus of the signaling pathways tied to calcium and may therefore be an effective target for multiple clinically relevant scenarios.

The following examples are presented in order to more fully illustrate some embodiments of the invention They should, in no way be construed, however, as limiting the scope of the invention.

EXAMPLES

Example 1

The Voltage-Dependent Calcium Channel β Subunit Contains Two Stable Interacting Domains Materials and Methods Subcloning, Expression and Purifications of the VDCC β3 Subunit:

Recombinant rat VDCC β 3 subunit (M88751) was expressed in *E. coli* strain BL-21 Tuner (Novagen), containing the "RIL" Codon Plus™ plasmid (Stratagene), using a modified pET21 (Novagen) vector (an 8×His and TEV protease site were engineered between the pET21d's NcoI and BamHI sites—a gift of Dr. Sean Juo). The protein was purified by sequential metal-chelate, ion-exchange and hydroxylapatite chromatography.

Polymerase chain reaction (PCR) was used to engineer EcoRI and BamHI restriction sites into the β 3 gene. The oligonucleotide primers used for amplification of the β 3 gene from the original plasmid were the following: Sense primer A, 5'-GCGCGGATCCTATGACGACTCCTACGTCCCC (SEQ ID NO: 1); Antisense primer B, 5'-GCGCGGATC-CTATGACGACTCCTACGTGCCC (SEQ ID NO: 2). PCR product was ligated into doubly digested (EcoRI and BamHI) pET21d vector. Positive clones were identified by restriction analysis and subsequently sequenced.

Transformed Tuner cells were grown for 3-4 hr. at 37° C. in 10 liters of LB media, containing 100 µg/ml ampicillin and 34 µg/ml chloramphenicol. Upon reaching an A600 of 0.3, the temperature was lowered to 16° C. and growth continued until the culture reached an A600 of 0.6. Protein expression was induced with 200 µM IPTG. Cells were harvested after 14 hr by centrifugation, frozen and suspended in 100 ml lysis buffer, buffer L (300 mM NaCl; 50 mM Na-phosphate, pH=7; 1 mM PMSF; 5 mM MgCl2; 0.2% Triton; 1 mM βME; 10 mg lysozyme; 1 mg DNase). After lysis by French pressure cell (Aminco), cell debris was removed by centrifugation at 20,000×g. The soluble fraction was loaded onto a pre-equilibrated metal chelate "Talon" (Clontech) column (buffer A—300 mM NaCl; 50 mM Na-phosphate, pH=7), at a flow rate of 1.5 ml/min. The column was washed with buffer A, containing 5 mM imidazole, until a stable base line was achieved. After elution with buffer A, supplemented with 150 mM imidazole, the protein eluate was then diluted 3 fold with water and loaded onto a pre-equilibrated Source-Q (Amersham Pharmacia) column (buffer Q—70 mM NaCl; 20 mM Na-phosphate, pH=7). The column was then washed with buffer Q and fractions were eluted with a shallow linear gradient of buffer Q, containing 70-300 mM NaCl. VDCC β3 containing fractions were pooled (130-150 mM NaCl) and diluted 2 fold in 600 mM NaCl to buffer H concentrations (10 mM phosphate buffer, pH=7; 300 mM NaCl) and subjected to TEV protease prepared in house. The proteolysis continued for 12 hr. Subsequently, the sample was loaded onto a pre-equilibrated (with H buffer) hydroxylapatite (Calbiochem) column and eluted with a linear gradient of H buffer 10-100 mM K-phosphate pH=7 (eluted at 50 mM K-phosphate). Pooled fractions were concentrated to 10 mg/ml using spin concentrators (Vivascience), divided into aliquots and flash-frozen in liquid N2.

Subcloning, Expression and Purification of VDCC β 2a Subunit

PCR was used to engineer EcoRI and BamHI restriction sites into the VDCC β 2a (X64297) gene. The oligonucleotide primers used for amplification of the new β 2a gene from the original plasmid were the following: Sense primer C, 5'-GCGCGGATCCCTTGACAGGCACCTCGCGGC-3' (SEQ ID NO: 3); Antisense primer D, 5'-CGCCGAATTCT-CATTGGCGGATGTA-3' (SEQ ID NO: 4). Subsequent subcloning was as described for VDCC β 3.

The VDCC β 2a subunit was expressed as for β 3. Purification was as follows. The soluble fraction of the crude extract was loaded on a pre-equilibrated Ni-CAM column (Sigma) (buffer B—50 mM Na-phosphate, pH=8; 300 mM NaCl) and washed with buffer B, containing 5 mM imidazole. The protein was then eluted with buffer B, containing 150 mM imidazole, and diluted 6 fold, followed by loading onto a pre-equilibrated Q-sepharose (Amersham Pharmacia) column buffer C-20 mM Na-phosphate, pH=8; 40 mM NaCl; 5 mM βME). Fractions were eluted with a shallow linear gradient of buffer C containing 40-200 mM NaCl and subjected to TEV proteolysis for 12 hr. VDCC β 2a containing fractions were pooled (80-100 mM NaCl) and loaded onto a pre-equilibrated gel filtration column (buffer G—10 mM Tris pH=8; 10 mM βME; 200 mM NaCl). The protein was eluted with buffer G. The pooled fractions were further processed as for β 3.

Subcloning, Expression and Purification of VDCC β 2a Domain I

PCR was used to engineer EcoRI and BamHI restriction sites into the β 2a domain I construct. The oligonucleotide primers used for amplification of the β 2a domain I construct from the original β 2a plasmid were the following: sense primer E, 5'-GCGCGGATCCAGCCGTCCATCCGATTCA-GATGTG-3' (SEQ ID NO: 5); antisense primer F, 5'GCGC-GAATTCTCACTTTGCTCTCTGTTCATGCTGTAG-3' (SEQ ID NO: 6). Subsequent subcloning was as described for VDCC β 3.

The β 2a domain I was expressed as for β 3. Purification was as follows. The soluble fraction of the crude extract was loaded on a pre-equilibrated Talon column (buffer A) and washed with buffer A, containing 75 mM imidazole. The protein was then eluted with buffer A, containing 150 mM imidazole, pooled and subjected to TEV proteolysis for 12 hr. The protein was then diluted 3 fold with 300 mM NaCl, loaded on a pre-equilibrated (buffer H) hydroxylapatite column and eluted with a linear gradient of H buffer 10-140 mM K-phosphate (eluted at 70 mM K-phosphate). The pooled fractions, with the addition of 10 mM βME, were loaded onto a pre-equilibrated gel filtration column (buffer G) and eluted with buffer G. The pooled fractions were processed as above.

Subcloning, Expression and Purification of VDCC β 2a Domain II

PCR was used to engineer EcoRI and BamHI restriction sites into the β 2a domain II construct. The oligonucleotide primers used for amplification of the β 2a domain II construct from the original β 2a plasmid were the following: primer G, sense 5'-GCGCGGATCCCACTCCAAAGAGAAAA-GAATGCCC-3' (SEQ ID NO: 7); Antisense primer I, 5'-GCGCGAATTCTCAAAGGAGAGGGTTGGG-GAGATTGCT-3' (SEQ ID NO: 8). PCR product was ligated into a doubly digested (EcoRI and BamHI) pET43.1a (Novagen) plasmid, thereby encoding a C-terminal fusion to the NusA protein with a 6×His Tag and thrombin site separating the two. A modified pET43 (8×His followed by a TEV cleavage sequence was inserted between the pET43 SpeI and BamHI sites) was also prepared to express domain II in the same way as with the commercial pET43.

The β 2a domain II was expressed as above. Purification of the NusA-Domain II fusion proceeded as follows. The soluble fraction of the crude extract was loaded on a pre-equilibrated Ni-CAM column (buffer B) and washed with buffer B, containing 5 mM imidazole. The protein was then eluted with buffer B, containing 30 mM imidazole, loaded on a pre-equilibrated (H buffer) hydroxylapatite column and eluted with a linear gradient of buffer H 10-250 mM K-phosphate (eluted at 100 mM K-phosphate). The protein was then subjected to thrombin (Sigma) proteolysis (5 U/mg of fusion protein) for 14 hr. The cleaved protein was diluted 2 fold and applied to a pre-equilibrated Q-sepharose column with PBS. The flow-through fractions were pooled, divided into aliquots and flash-frozen in liquid N2.

Subcloning, Expression and Purification of VDCC β2a Removable Linker Core

Subcloning was stepwise. First, pre-digested PCR product encoding domain I was ligated into EcoRI and BamHI digested pET21d plasmid. Next, pET21d-domain I plasmid was prepared and digested with EcoRI and NotI for ligation with a pre-digested PCR product encoding domain II. Finally, PCR product, encoding the linker between domains I and II and two TEV proteolysis sites at both ends, was singly digested with EcoRI and ligated into pre-digested EcoRI vector, now containing both domain I and domain II Positive clones containing the insert in the correct orientation were identified using restriction analysis and sequencing.

PCR was used to engineer EcoRI, BamHI and NotI restriction sites into the β 2a domain I and domain II encoding fragments. The oligonucleotide primers used for amplification of the β 2a domain I fragment from the original β 2a plasmid were the following: sense primer E-5' listed above; Antisense primer J, 5'-CGCGGAATTCCTTTGCTCTCT-GTTCATGCTGTAG-3' (SEQ ID NO: 9). The oligonucleotide primers used for amplification of the β 2a domain II fragment from the original β 2a plasmid were the following: Sense primer K-5'-CGGAATTCAAGCTTCACTCCAAA-GAGAAAAGAATGCCC-3' (SEQ ID NO: 10); Antisense primer L-5' -TTATACTAGCGGCCGCTCAAAG-GAGAGGGTTGGGGAGATT-3' (SEQ ID NO: 11). The oligonucleotide primers used for amplification of the β2a linker fragment with the addition of two TEV sites from the original β2a plasmid were the following: sense primer M-5'-CGCG-GAATTCGAAAACCTGTACTTTCAGGGC-CAAGGGAAATTCTACT CCA-3' (SEQ ID NO: 12); Antisense primer N-5' CGCGGAATTCGCCCTGAAAGTACAG-GTTTTCGGGTGACGTTACACTGT TT-3' (SEQ ID NO: 13)

The VDCC β2a removable linker core was expressed as above. The soluble fraction of the crude extract was loaded onto a pre-equilibrated Ni-CAM column (buffer B) and washed with buffer B, containing 5 mM imidazole. The protein was then eluted with buffer B, containing 150 mM imidazole, pooled and diluted two fold, followed by loading onto a pre-equilibrated hydroxylapatite column (H buffer). Protein was eluted with a linear gradient of H buffer (10-250 mM K-phosphate) at about 120 mM K-phosphate. Pooled fractions were diluted 4 fold and subjected for 12 hr to TEV protease. 10 mM PME was added to the sample and loaded onto a pre-equilibrated gel filtration column (G buffer). Protein was eluted with buffer G. The pooled fractions were processed as above.

Limited Proteolysis of VDCC β2a and β3 Subunits

Papain (20 µg/ml) (Sigma-Aldrich) was activated for 30 min in activation buffer (1.25 mM EDTA; 6.25 mM cysteine; 62.5 mM βME, at pH=7), and added to 3 mg/ml VDCC β 3 or b2a in a 1:20 dilution. The final ratio of papain to β protein was 1:3000. Trypsin (60 µg/ml) was added to 3 mg/ml β 3 in a 1:20 dilution, giving a final ratio of protease to protein of 1:1000. Reactions were performed on ice. Proteolysis progress (at different time intervals) was monitored by SDS-PAGE. Proteolysis products were purified for further analysis by HPLC reverse phase chromatography using a C4 column (Vydac) with a shallow acetonitrile gradient 30-80% (both solvents were supplemented with 0.05% trifluoroacetic acid).

AID Peptide Binding Assays

Fluorescence polarization was used to determine the equilibrium dissociation constant (KD) for the interaction between a fluorescein-labeled AID peptide, purified and various VDCC β constructs. The synthetic peptide was purified by HPLC reverse chromatography using a C18 column (Vydac) with a shallow acetonitrile gradient 20-80% (both solvents were supplemented with 0.05% trifluoroacetic acid). Its sequence is derived from the AID motif of: the CaV1.1 I-II linker and is as follows: fluorescein-GGQQLEEDLRGYNSWITQGE-COOH (SEQ ID NO: 14). A mutant peptide, fluorescein-GGQQLEEDLRGSNSWITQGE-COOH (SEQ ID NO: 15) was prepared, in addition. Increasing concentrations of protein were incubated with 0.5 nM labeled peptide for 10 min in the dark at room temperature. Polarization measurements were taken with an ISS K2 fluorescence spectrophotometer at excitation and emission wavelengths of 492 and 520 nm, respectively, at 20° C., maintained by a temperature-controlled water bath. Polarization measurements were made with integration times on the order of 20 seconds, achieving a standard deviation of 5 percent of signal. Binding isotherms for the various samples were measured three independent times. Binding data were analyzed in SigmaPlot (SPSS) by nonlinear regression used to fit a binding function as defined by the following equation:

$$\Delta P = \frac{B_{max} X}{K_D + X}$$

where X is the concentration of free ligand, $\Delta P$ is the change in fluorescence polarization of the fluorophore (baseline polarization of the labeled peptide alone was subtracted), Bmax is the maximum change in polarization upon saturation and $K_D$ is the concentration of ligand required to reach half maximal binding.

CD Spectroscopy

All CD measurements were performed with an Aviv CD spectrometer model 202. Spectra were measured over the range of 280-180 nm at a scan rate of 1 nm/sec. For all measurements, a cell with 0.1 mm path length was used. Each spectrum is an average of 4 scans. The raw data were corrected by subtracting the contribution of the buffer to the CD signal. Data were smoothed and converted to molar ellipticity units. The measurements were taken at a constant temperature of 20° C., with an approximate protein concentration of 35 µM. More precise concentration of protein was obtained using the predicted extinction coefficient of the proteins and their 280 nm absorbance. The proteins' molar extinction coefficients ($M^{-1}$ $cm^{-1}$) at 280 nm are: β 3—52300; β 2a—39760; β 2a linkerless core—24870. The difference spectrum (full length β 2a—linkerless core) was calculated according to (Ausio, J., Toumadje, A., McParland, R., Becker, R. R., Johnson, W. C., Jr., and van Holde, K. E. (1987) Biochemistry 26, 975-982). Deconvolution calculations were computed with CDNN (Bohm, G., Muhr, R., and Jaenicke, R. (1992) Protein Eng 5, 191-195) using the 33 data basis set.

Electrophysiology

Preparation of Xenopus laevis oocytes, injection of mRNA of VDCC subunits, and electrophysiological recording and analysis were performed, as described (Kang, M. G., Chen, C. C., Felix, R., Letts, V. A., Frankel, W. N., Mori, Y., and Campbell, K. P. (2001) J Biol Chem 276, 32917-32924). The negative control group were oocytes expressing CaV1.2 (α1C) subunit only by mRNA injection followed by injection of protein buffer (PB). The positive control group were oocytes expressing α1C and β3 subunits by mRNA injection, followed by injection of protein buffer (PB). The oocytes of experimental groups were injected with α1C mRNA followed by injection of VDCC β proteins, two days after the mRNA injection. Injection of protein (0.4 mg of protein per oocyte) was performed similarly as mRNA injection. Oocytes injected with VDCC β proteins were incubated one more day and the expressed calcium channel currents were recorded using the two-electrode voltage-clamp technique.

Results

Using a T7 expression system, an E. coli BL-21 derivative cell line that allows for fine-tuning IPTG induction by better controlling IPTG concentration, and low temperature growths, overexpression of soluble, full-length rat VDCC β3 was obtained. In addition, the rabbit β2a isoform was subcloned and expressed in the same system. The expression vectors encoded a histidine tag on the amino terminus, followed by a TEV protease site and the ensuing desired coding sequence. VDCC β2a manifested robust expression.

Figure 1:
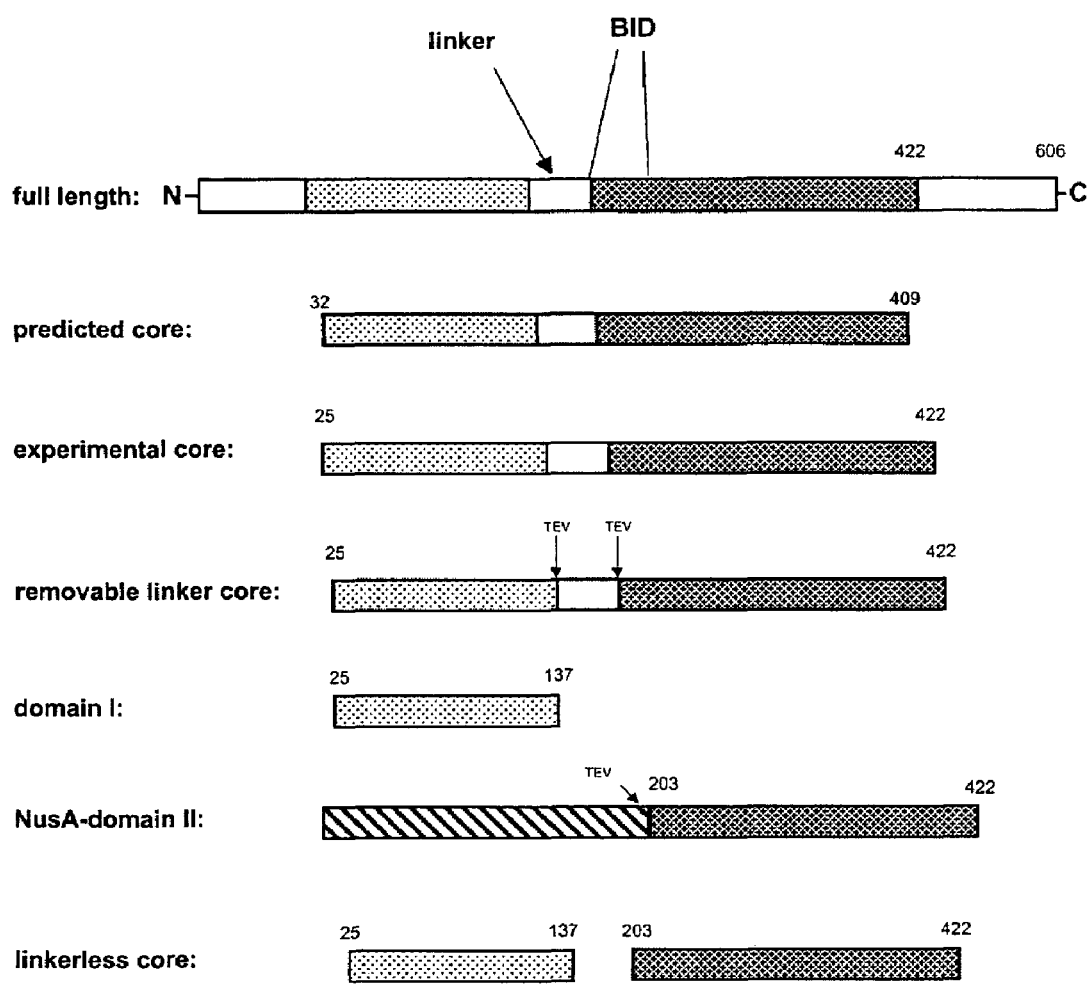
FIG. 1 is a schematic of the rabbit VDCC β2a primary sequence, a representative of the β family, and the various constructs prepared in this study. The lightly stippled box denotes the first conserved domain, domain I, and the darkly stippled box denotes the second conserved domain, domain II. The BID, a sequence responsible for binding to VDCC α1, is located as shown in the beginning of domain II (Opatowsky et al., (2003). J Biol Chem 278, 52323-52332).

Purification schemes for the VDCC β isoforms all utilized as a first step subsequent to lysis, metal chelate resin chromatography to isolate the His-tagged target proteins. This first step usually produced protein that was greater than 80-85% homogeneous. Histidine tags were removed by cleavage with TEV protease. The TEV protease is highly specific and does not cleave other sites on the protein. Full length VDCC β3 was highly sensitive to proteolysis. Therefore, efficient and rapid chromatographic processing proved essential and was applied systematically. The full-length proteins are shown in FIG. 1.

An important and classical method of probing protein structure is limited proteolysis, which when applied to the determination of domain structure, assumes that flexible and exposed regions of the protein are available to the protease and thus subject to hydrolysis.

Figure 2:
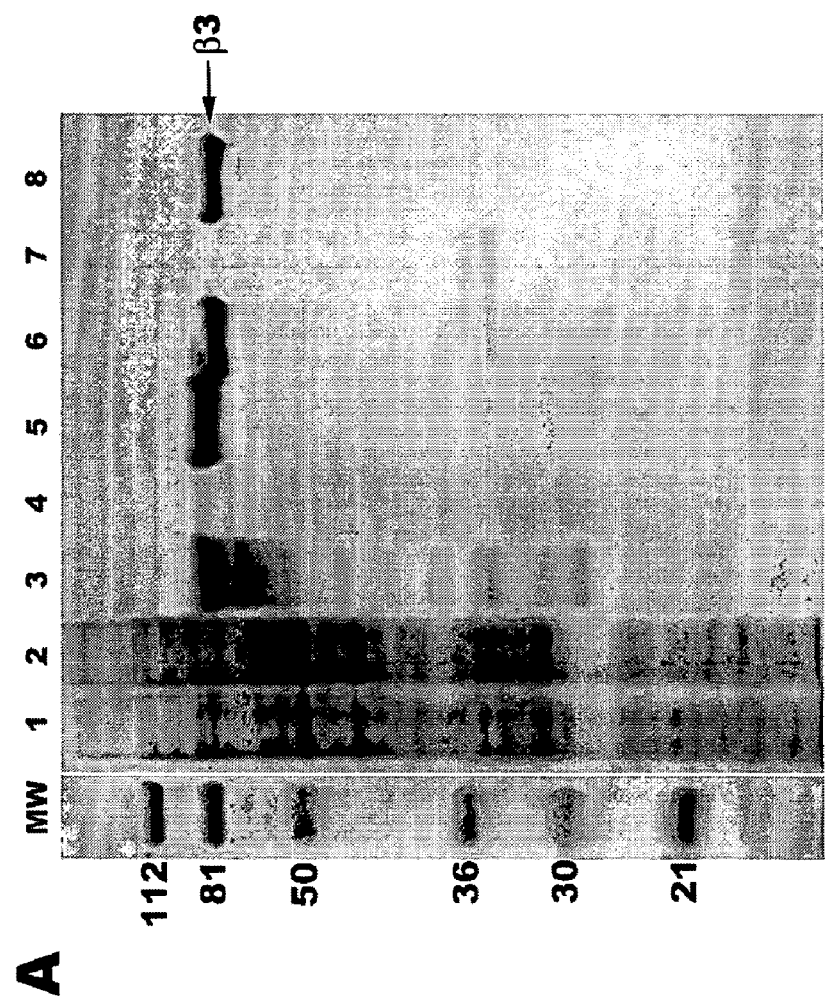
FIG. 2 demonstrates the purification of recombinant, full-length VDCC β proteins. A: SDS-PAGE of VDCC β3 purification in its various stages; MW: Molecular weight markers (kD); lane 1: soluble fraction of the crude lysate; lane 2: metal chelate column flow through fraction; lane 3: metal chelate column eluate fraction (first major purification step); lane 4: ion-exchange column flow through fraction; lane 5: ion-exchange column eluate fraction (second major purification step); lane 6: protein after TEV digestion which removes a 26 residue amino terminus including the histidine tag, producing a distinct mobility shift; lane 7: hydroxylapatite column flow through fraction; lane 8: hydroxylapatite column eluate (final major purification step). B: SDS-PAGE of purified VDCC β2a; MW: Molecular weight markers (kD); neighboring lane: gel-filtration column eluate (final major purification step) after concentration (Opatowsky et al., 2003).

Both β2a and β3 recombinant full-length proteins were subjected to limited proteolysis using both papain, a highly non-specific protease, and trypsin, a more specific protease. The time course results for limited digestion by papain are in FIG. 2. Early in the time course, a stable polypeptide emerged which was an approximately 40 kD fragment. Subsequently, this fragment was further digested such that after 16 hours, 2 two stable fragments remained, one of higher mobility and another of medium mobility. Both isoforms basically followed the same pattern (β2a seems to have an intermediate fragment).

Preparative limited proteolyses of VDCC β3 were performed, and samples were separated and analyzed by mass spectrometry and amino-terminal peptide sequencing. Electrospray mass spectrometry produced masses of 13,198 and 23,938 Dalton for the two stable fragments. N-terminal sequencing of these fragments indicated that the smaller one primarily began at residue 23 whereas the larger fragment began at residue 158. Combining these data allowed us to demarcate the boundaries of these stable domains. The smaller fragment is defined from 23 to 138 of the β3 sequence and designated domain I while the larger fragment is defined from 158 to 371 and designated domain II. The β2a domain definitions are 25 to 146 and 204 to 423 for domains I and II, respectively, as determined by sequence alignment to the β3 boundaries MALDI-MS analyses of the early proteolytic 40 kD fragment gave a cluster of masses centered around 39,420 Dalton. This mass is consistent with a fragment extending from residue 21 to 370, and fits as well with the mass spectrometry and peptide sequencing results of the stable domains. Moreover, the stable domains are derivatives of this early fragment as discerned by the time course results, requiring them to be equal or smaller than the early fragment. The large fragment was therefore a core protein.

Further support for the structural division, i.e. two domains with a flexible connecting linker, came from limited proteolysis of a recombinant protein, whose ends were engineered based on homology of the VDCC β family (see FIG. 3; predicted core).

In order to determine whether the two domains interact, constructs expressing His-tagged β2a domain I, alone, and domain II as a C-terminal fusion protein with NusA were prepared (FIG. 3). His-tagged domain I was mixed with domain II which had been isolated away from the fusion partner NusA and shown to bind in a pull-down assay, indicating stable association of the two domains (FIG. 4a). Further support for stable association of the two derives from chromatographic experiments, where gel filtration analysis of domain I alone gives an elution volume of 93 ml on a Superdex 200 size-exclusion column. When purified removable linker core protein (FIG. 3), was digested by TEV so that the domains were no longer covalently linked, to give linkerless core, and then run out on the identical column, both domains I and II coeluted at an elution volume of 83 ml (FIG. 4b). The significant shift in elution volume for domain I and coelution of both domains strongly supports association of domains I and II, with solution conditions, ruling out the presence of non-specific or adventitious association.

Figure 5:
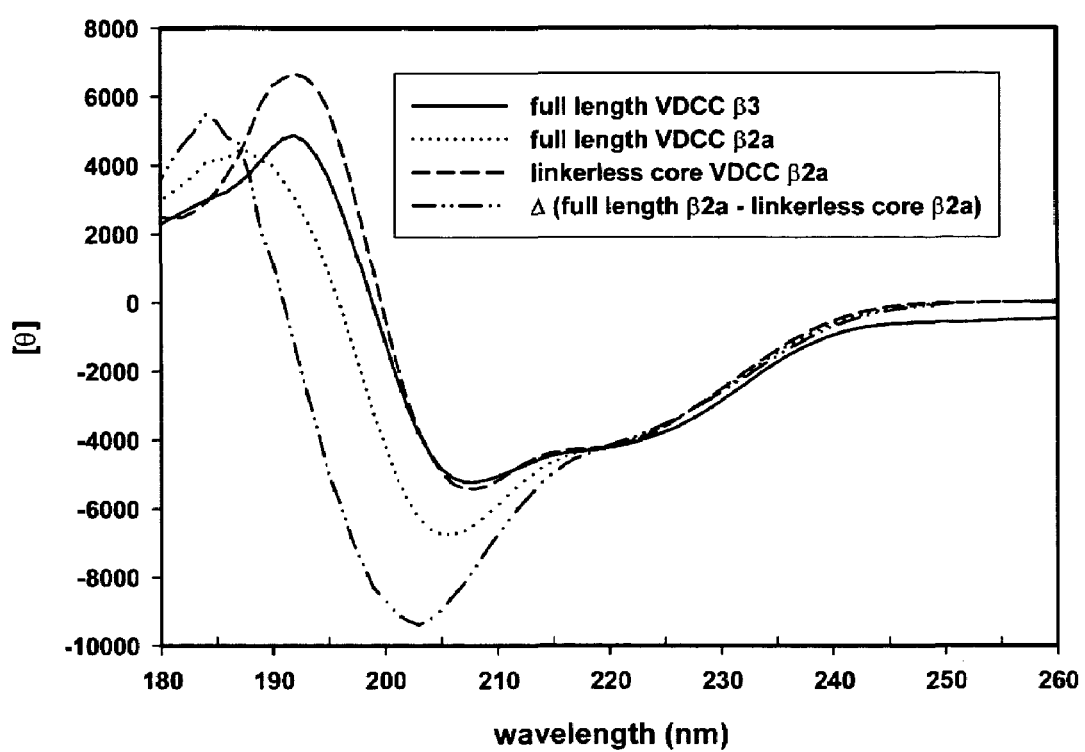
FIG. 5 demonstrates circular dichroism spectra of VDCC β proteins. Each curve is labeled as per the legend. The ordinate is molar ellipticity units (deg cm2 dmol-1) (Opatowsky et al., 2003).

CD spectra of several VDCC β forms were measured, and are shown in FIG. 5. The spectra of the full-length β3 and β2a proteins are similar, indicating comparable secondary structure. Furthermore, these spectra indicate that the proteins are of a mixed alpha helix/beta sheet type, as seen by visual inspection of the curves as well as by deconvolution calculations. The calculations point to approximately 35 percent sheet and 15 percent helix. A comparison of β3 and the β2a linkerless core spectra shows a very strong resemblance between these two proteins. In addition, the difference spectrum between β2a full length protein and the β2a linkerless core protein gives insight into the segments of protein outside of domains I and II, namely the N-terminal segment, the linker between domains and the C-terminal segment. This spectrum points to a significant fraction of random coil structure as evidenced by the shift in minimum and magnitude towards 198 nm and diminution of the other minimum at 222 nm, consonant with the limited proteolysis results.

In order to determine structure—function correlations regarding domain analysis, and to have a robust in vitro assay for further correlations with structural and electrophysiological experiments, a novel assay that measures binding of VDCC β proteins to an α1 I-II linker-derived AID peptide was developed. The assay employed fluorescence polarization measurements. AID peptides of 18-20 residue length were synthesized, some of them labeled with fluorescein attached at the amino-terminus. Labeled peptide was then titrated with increasing concentrations of β, and the fluorescence polarization emitted by the labeled peptide was determined. Fluorescence emission polarization is proportional to the rotational correlation time (tumbling) of the labeled molecule. Tumbling, in part, depends on the molecular volume, i.e. larger molecules have larger volume and slower tumbling which in turn gives rise to increased polarization of emitted light. If the peptide associates with β, its effective molecular volume greatly increases, as evidenced by values of polarization fluorescence emissions. Equilibrium isotherm titrations were performed with full-length β2a and linkerless core β2a. The binding curves (FIGS. 6a and 6b) indicate high affinity single site binding on the order of 6-15 nM. The binding is specific since addition of unlabeled AID peptide lowers the polarization to basal levels, i.e. it effectively competes with the labeled peptide (data not shown)

The assay was further validated by testing a mutant AID peptide, which has a single amino acid change (Y to S, which has been shown to have less than five percent binding capability of WT. No binding of the mutant AID was detected with the assay, at concentrations of up to 350 nM β2a protein, though WT protein at this concentration reached saturation binding.

Figure 6:
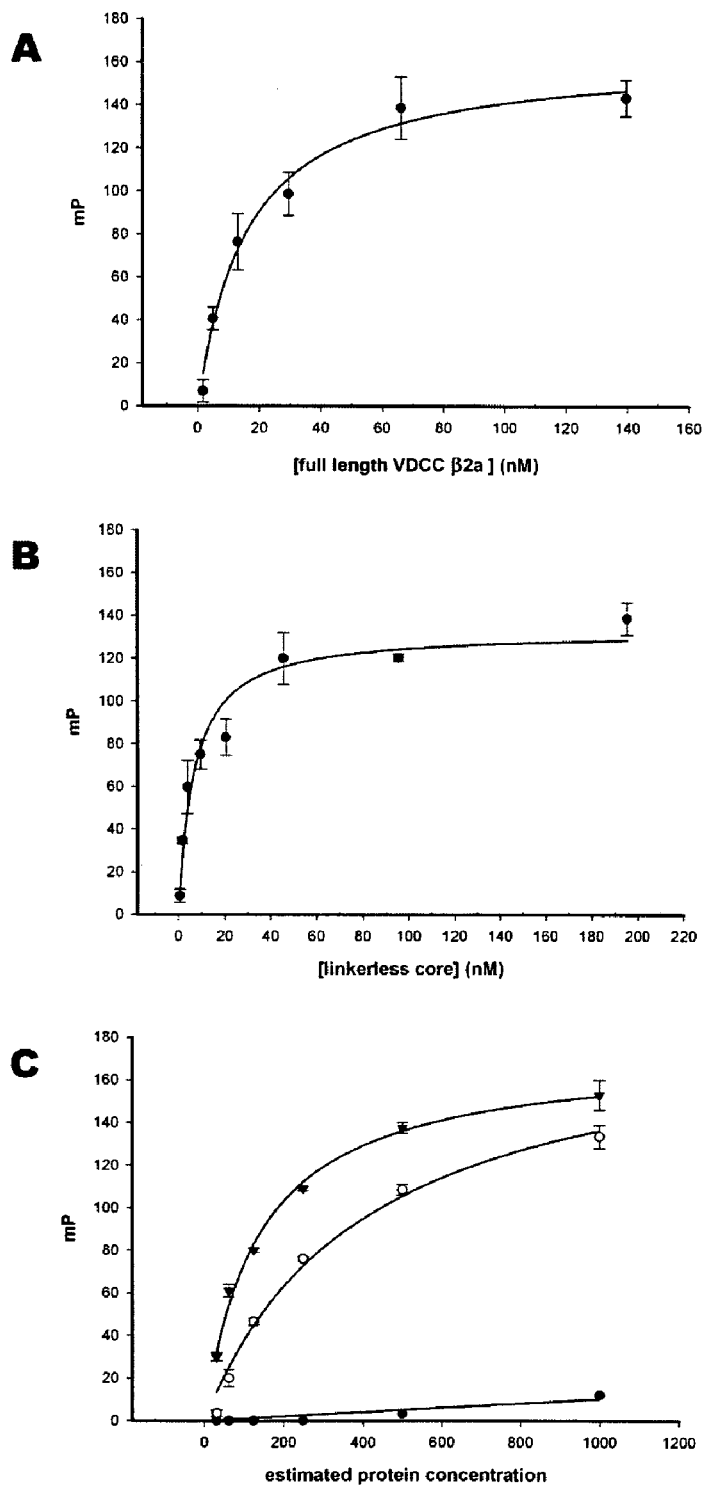
FIG. 6 demonstrates binding isotherms of VDCC β with a fluorescein labeled AID peptide as measured by fluorescence polarization. A: full-length β2a gives a KD of 16.1±3.8 nM. B: linkerless core i.e. domain I plus domain II gives a KD of 6.6±1.3 nM. C: relative binding curves: filled circles are domain I alone; empty circles NusA-domain II fusion after incubation with TEV protease; filled triangles are domain I plus NusA-domain II fusion after incubation with TEV protease. Estimated protein concentration is in nM units (Opatowsky et al., 2003).
Figure 8:
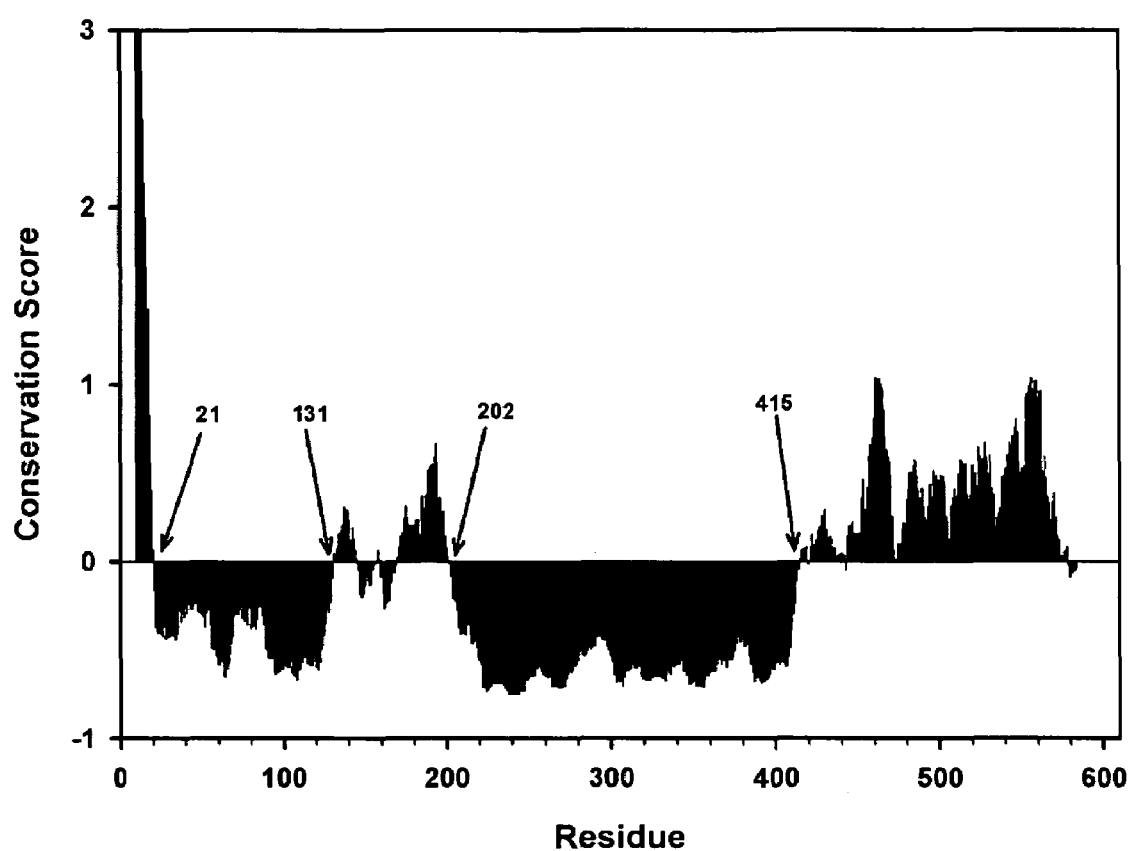
FIG. 8 demonstrates VDCC β protein family sequence conservation. 24 protein sequences of VDCC β were selected from the NCBI database, based on a search with Blast. Splice variants were removed and the selection included several invertebrate and vertebrate sequences. These sequences were run on the ConSeq server (http://conseq.bioinfo.tau.ac.il), which uses the Max4Site algorithm (Pupko, T., Bell, R. E., Mayrose, I., Glaser, F., and Ben-Tal, N. (2002) Bioinformatics 18 Suppl 1, S71-77) to compute sequence conservation scores. Scores account for evolutionary distances and are normalized to units of standard deviation. Zero represents the average evolutionary rate and less than 0 indicates increasing conservation. The scores were then averaged in a window of ±five residues (i.e. 11 total residues) for every residue and plotted as seen in the histogram. Arrows indicate the residue numbers of blocks of significant conservation. These blocks correspond quite well with the biochemically defined domains I and II. The reference sequence for numbering is rabbit β2a (Opatowsky et al., 2003).

The binding assay was then used to determine which domains of β are required for association with the AID peptide (FIG. 6c). Binding of the β2a domain I was assessed, which was negligible in the estimated concentration regime tested. The NusA-domain II fusion, which contained a TEV protease site separating NusA and domain II was incubated with TEV protease and the labeled peptide for one hour and then fluorescence polarization measured, where domain II demonstrated significant binding affinity for the AID. Incubation of the β2a domain I protein and the NusA-domain II fusion protein, containing a TEV protease site separating NusA and domain II, with TEV protease and the labeled peptide demonstrated that the presumed domain I-domain II complex binds with even higher affinity. Since identical amounts of the various proteins were taken in the three stages of this experiment, the curves provided a relative measure of binding for the different domains and their individual contributions. Thus, domain I does not bind by itself to the AID at high affinity whereas domain II does. However, it is clear that domain I somehow contributes to the increased binding of the AID for the presumed domain I-domain II complex.

In order to determine that the bacterially expressed, recombinant proteins were physiologically active, two-electrode, two-voltage-clamp measurements of *Xenopus* oocytes expressing α1 and microinjected with our protein samples was performed. Increased current amplitude and a shift of the steady-state activation was determined in I-V plots of Cav1.2 currents (FIG. 7), by injection of β proteins (except domain I), demonstrating the functional activity of the β proteins. Data values and statistical analyses are described in Table 1. The current amplitude increase and change of steady-state activation are statistically significant in all experimental groups except a group injected with β2a domain I protein.

TABLE 1

Electrophysiological Parameters of the Cav1.2 oocyte expression plus protein microinjections

| Properties | α1.2 | α1.2 + β3 mRNA | α1.2 + Full β$_3$ Pro. | α1.2 + Core β$_3$ Pro. |
|---|---|---|---|---|
| Current amplitude (A) | | | | |
| I at 20 mV | −0.15 ± 0.01 | −0.56 ± 0.08** | −0.47 ± 0.04*** | −0.45 ± 0.04*** |
| I at 30 mV | −0.16 ± 0.01 | −0.48 ± 0.07** | −0.44 ± 0.03*** | −0.41 ± 0.03*** |
| n | 10 | 11 | 10 | 8 |

TABLE 1-continued

Electrophysiological Parameters of the Cav1.2 oocyte expression plus protein microinjections Steady-state activation parameters from I-V curve

| | | | | |
|---|---|---|---|---|
| $V_{1/2}$ (mV) | 22.60 ± 4.22 | 10.67 ± 1.95** | 10.03 ± 3.36* | 10.65 ± 4.46* |
| k (mV) | 11.91 ± 0.84 | 9.08 ± 0.36** | 10.56 ± 0.42 | 10.06 ± 1.15 |
| n | 10 | 11 | 10 | 8 |

| Properties | α1.2 + Full β$_2$ Pro. | α1.2 + Core β$_2$ Pro. | α1.2 + d1 + d2 β$_2$ Pro. | α1.2 + d1 β$_2$ Pro. |
|---|---|---|---|---|

Current amplitude (A)

| | | | | |
|---|---|---|---|---|
| I at 20 mV | −0.71 ± 0.09** | −0.87 ± 0.09*** | −0.44 ± 0.04*** | −0.16 ± 0.01 |
| I at 30 mV | −0.49 ± 0.06** | −0.70 ± 0.07*** | −0.34 ± 0.03** | −0.18 ± 0.02 |
| n | 11 | 11 | 12 | 9 |

Steady-state activation parameters from I-V curve

| | | | | |
|---|---|---|---|---|
| $V_{1/2}$ (mV) | 3.68 ± 0.33*** | 6.84 ± 0.83*** | 3.24 ± 0.93*** | 24.00 ± 3.01 |
| k (mV) | 8.48 ± 0.53*** | 8.43 ± 0.23*** | 9.49 ± 0.92 | 12.18 ± 0.49 |
| n | 11 | 11 | 12 | 9 |

Values are presented as mean ± SEM.
*$p < 0.05$,
**$p < 0.01$, and
***$p < 0.001$ (respect to aI.2),
I: current,
V: potential,
$V_{1/2}$: membrane potential for half-maximal activation,
k: slope factor,
n: cell number,
Pro.: Protein,
d: domain.

Furthermore, the results show that the core protein electrophysiological activity corresponds well to full-length protein activity. In addition, the injection of purified domain I and domain II proteins prepared by proteolysis of full length protein and subsequent purification, comparable to β2a linkerless core protein from our in vitro experiments, still enabled significant changes in the current amplitude and activation shift in a qualitatively similar manner as native protein. It should be noted that the injected recombinant β2a proteins were found subsequently to contain a mutation (P122R) due to the PCR subcloning. This mutation had no effect on the proteins' electrophysiological activity.

Example 2

Crystallization of the VDCC β Subunit Functional Core

Materials and Methods

Subcloning, Expression and Purification

The VDCC β2a linkerless core construct was subcloned into a modified pET21-d vector and expressed as previously described (Opatowsky, Y., Chomsky-Hecht, O., Kang, M. G., Campbell, K. P., and Hirsch, J. A. (2003). J Biol Chem 278, 52323-52332). A VDCC β2a fused core construct i.e. domain I fused to domain II was prepared as follows. Subcloning was sequential PCR was used to engineer BamHI and EcoRI restriction sites into the β2a domain I encoding gene. Primers used were the following: sense, 5'-GCGCGGATCCAGC-CGTCCATCCGATTCAGATGTG-3' (SEQ ID NO: 16); antisense, 5'-CGCGGAATTCCTTTGCTCTCTGTTCAT-GCTGTAG-3' (SEQ ID NO: 17). The PCR product was ligated into a doubly digested (BamHI, EcoRI) pET21-d vector. Next, NotI and EcoRI sites were introduced into the domain II fragment by PCR using the sense primer, 5'-CG-GAATTCAAGCTTCACTCCAAAGAGAAAA-GAATGCCC-3' (SEQ ID NO: 18) and the antisense primer, 5'-TTATACTAGCGGCCGCTCAAAG-GAGAGGGTTGGGGAGATT-3' (SEQ ID NO: 19). Finally, the domain II PCR product was ligated into a doubly digested (EcoRI NotI) pET21-d vector, already containing the domain I encoding fragment. Positive clones were identified by restriction analysis and sequencing. The resulting gene encodes domain I fused to domain II with four residues (EFKL); SEQ ID No: 39) between them that arise due to the cloning procedure.

Expression of the proteins was essentially as described previously (Opatowsky et al., 2003, supra). In brief, protein was expressed in transformed Tuner (Novagen) E. coli grown in 2xYT media, containing 100 μg/ml ampicillin and 34 μg/ml of chloramphenicol at 16° C. for 14 hours. Cells were then harvested by centrifugation and frozen for subsequent use. Cell paste was suspended in 100 ml lysis buffer (300 mM NaCl; 50 mM NaPO4, pH 8; 1 mg DNase). After lysis by French press, cell debris was removed by centrifugation at 20,000×g. The soluble fraction was loaded onto a pre-equilibrated metal-chelate Ni-CAM (Sigma) column (buffer A: 300 mM NaCl; 50 mM NaPO4, pH 8) and washed with buffer A supplemented with 7 mM imidazole until a stable baseline was achieved. The protein was eluted with buffer A supplemented with 150 mM imidazole, diluted six fold with 10% glycerol, and loaded onto a Q-Sepharose (Amersham Pharmacia) column, pre-equilibrated with buffer B (70 mM NaCl; 20 mM NaPO4, pH 8). Fractions were eluted with a shallow gradient of buffer C (400 mM NaCl; 20 mM NaPO4, pH 8).

VDCC β2a containing fractions (180-220 mM NaCl) were pooled and subjected to TEV protease digestion, in order to remove the 8×His tag. Proteolysis continued for 12 hours, and subsequently the protein was loaded onto a hydroxylapatite (Calbiochem) column, pre-equilibrated with buffer D (200 mM NaCl; 50 mM NaPO4, pH 8), washed with buffer D until a flat baseline was achieved. Then, the protein was eluted with buffer E (200 mM NaCl; 200 mM NaPO4, pH 8; 5 mM β-mercaptoethanol), and applied to a pre-equilibrated Superdex-200 gel-filtration column (Amersham Pharmacia) with buffer F (200 mM NaCl; 20 mM Tris, pH 8; 5 mM β-mercaptoethanol). The elution peak was concentrated to 12 mg/ml using spin concentrators (Vivascience), divided into aliquots and flash frozen in liquid N2.

Crystallization

Initial screens of both proteins were performed at 4° C. and 19° C. with Hampton Screen I and II (Hampton Research) in 96-well sitting-drop plates (Corning). Drop size was 2 μl, with a sample-reservoir ratio of 1:1. After 24 hours, microcrystals and crystalline hits appeared with many high molecular weight PEG and ammonium-sulfate conditions. Crystallization was refined using hanging-drop vapor diffusion plates, by varying different precipitant concentrations versus different pHs and buffers. The addition of low concentrations of alcohols and salts, both at 4° C. and 19° C., gave optimal growth conditions for both the fused core and linkerless core forms. Both protein types gave thick rod shaped crystals at 1.6 M ammonium sulfate; 0.1 M Hepes, pH 7; 5 mM β-mercaptoethanol, grown at 4° C. (crystal form I). Crystals appeared after several hours and diffracted for 48 hours post setup. The fused core protein also gave plate shape crystals at three percent PEG 20,000 (Fluka); 0.1 M Bicine, pH 9; 100 mM NaCl, 5 mM β-mercaptoethanol, grown at 19° C. (crystal form II). These crystals appeared after 12 hours and diffracted for no longer than 36 hours post set up.

Data Collection

Prior to flash freezing in cryo-loops, crystals were gradually transferred to cryoprotecting solutions, containing, in addition to cryoprotectant (30% sucrose for the ammonium sulfate crystals, and 35% glycerol for the PEG crystals), all of the mother-liqueur components. Heavy atom soak crystals were prepared by adding a final concentration of 1 mM heavy atom solution to the mother liqueur, for 5 min prior to the cryoprotectant soak. Flash frozen crystals were then placed on the 110° K N2-cooled goniometer head for data collection. Using home x-ray source (rotating anode), crystals were screened for diffraction quality. Synchrotron data collection was conducted at the European Synchrotron Radiation Facility (ESRF) in Grenoble, France. The diffraction data were processed with DENZO/SCALEPACK (Otwinowski and Minor, 1997).

Results

Figure 9:
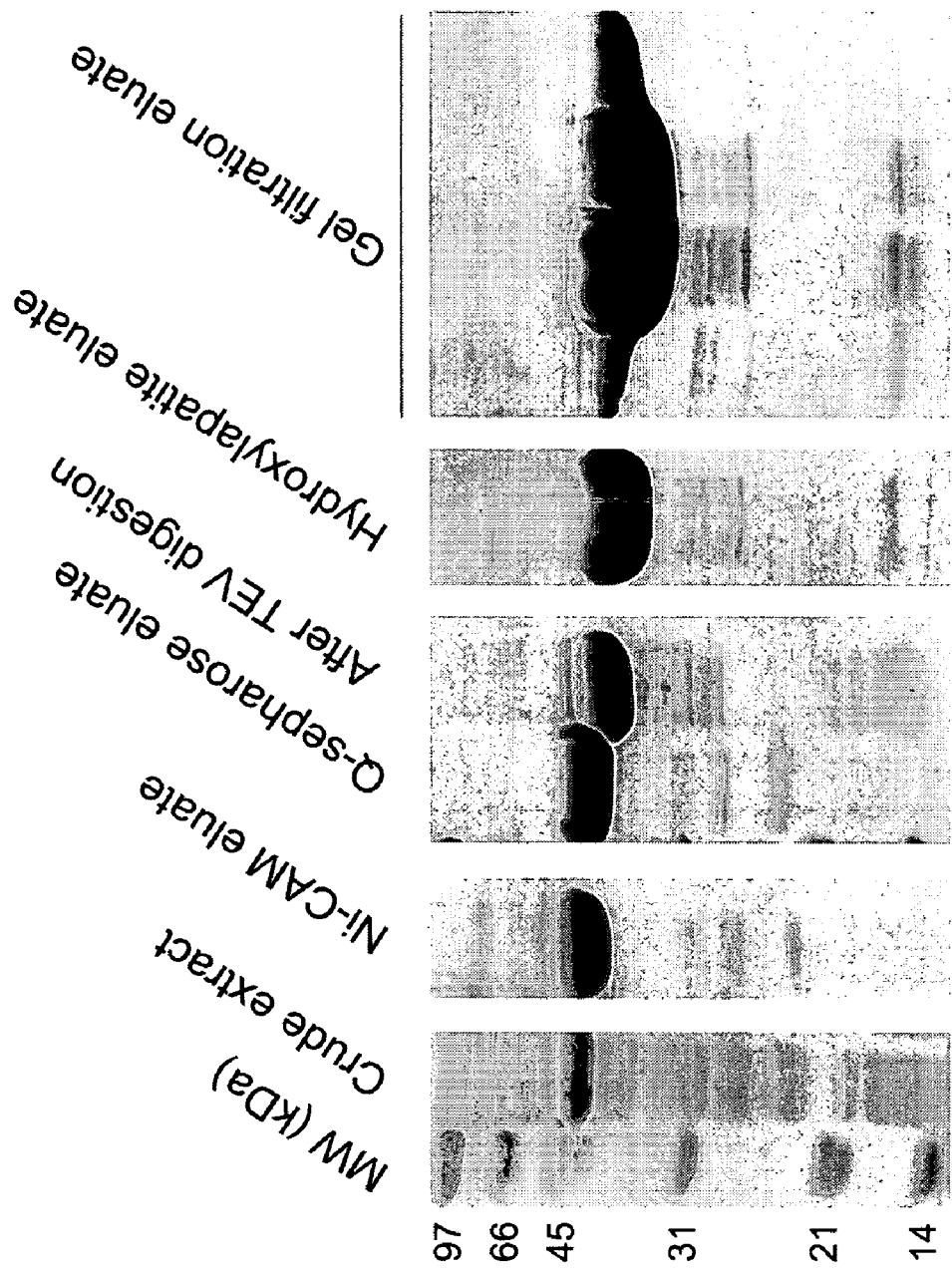
FIG. 9 is a photograph of an SDS-PAGE of the fused core construct purification steps. The gel-filtration eluate was used for crystallization.

Functional cores of the voltage-dependent calcium channel β subunit (β2a isoform), with an amino acid sequence corresponding to SRPSDSDVSL EEDREAVRRE AERQAQAQLE KAKTKPVAFA VRTNVSYSAA HEDDVPVPGM AISFEAKDFL HVKEKFNNDW WIGRLVKEGC EIGFIPSPVK LENMRLQHEQ RAK EFKL HSKEKRMPFF KKTEHTPPYD VVPSMRPVVL VGPSLKGYEV TDMMQKALFD FLKHRFEGRI SITRVTADIS LAKRSVLNNP SKHAIIERSN TRSSLAEVQS EIERIFELAR TLQLVVLDAD TINHPAQLSK TSLAPIVVYV KISSPKVLQR LIKSRGKSQA KHLNVQMVAA DKLAQCPPEL FDVILDENQL EDACEHLADY LEAYWKATHP PSSNLPNPLL* (SEQ ID NO: 20), and SRPSDSDVSL EEDREAVRRE. AERQAQAQLE KAKTKPVAFA VRTNVSYSAA HEDDVPVPGM AISFEAKDFL HVKEKFNNDW WIGRLVKEGC EIG-FIPSRVK LENMRLQHEQ RAK EFKL HSKEKRMPFF KKTEHTPPYD VVPSMRPVVL VGPSLKGYEV TDMMQKALFD FLKHRFEGRI SITRVTADIS LAKRSVLNNP SKHAIIERSN TRSSLAEVQS EIERIFELAR TLQLVVLDAD TINHPAQLSK TSLAPIVVYV KISSPKVLQR LIKSRGKSQA KHLNVQMVAA DKLAQCPPEL FDVILDENQL EDACEHLADY LEAYWKATHP PSSNLPNPLL* (SEQ ID NO: 21), respectively, were expressed in *E. coli*, and purified to homogeneity (FIG. 9). The functional cores were crystallized, and two crystal forms predominated (FIG. 10). While crystal form II (dmin=2.3 Å) (panel B) should provide us with a detailed atomic structure, form I (dmin=3.6 Å) (panel A) may provide structural information about conformational variability of these two-domain molecules.

To date, attempts to obtain experimental phasing by isomorphous replacement have been thwarted, since crystal form II suffers from significant non-isomorphism, as evident by the large deviations in the unit cell size along the longest axis and by the high c2 values (>20) obtained by scaling independent data sets, including native versus native sets (FIG. 11). Additional data processing statistics for the voltage gated calcium channel β subunit crystals are provided in Table 2.

TABLE 2

Properties of the crystals of VDCC β subunit functional core:

| Protein | Fused core | Fused core | Linkerless core |
|---|---|---|---|
| Crystal form | Form II | Form I | Form I |
| Wavelength (Å) | 0.933 | 0.976 | 0.976 |
| Space group | $P2_12_12$ | $P4_12_12$ | $P4_12_12$ |
| Unit-cell | a = 34.8 | a = b = 75.6 | a = b = 76.5 |
| Parameters (Å) | b = 74.1 | c = 164.4 | c = 164.9 |
|  | c = 163.8 | $\alpha = \beta = \gamma = 90°$ | $\alpha = \beta = \gamma = 90°$ |
|  | $\alpha = \beta = \gamma = 90°$ | | |
| Total reflections | 71732 | 25341 | 46242 |
| Unique reflections | 18271 | 6853 | 6448 |
| Completeness (%) | 92.8 (87.9) | 96.5 (98.1) | 100 (100) |
| Rmerge (%) | 4.8 (31) | 5.3 (49) | 10 (43) |
| I/σ | 15.4 (4.3) | 19.5 (2) | 13.2 (4) |
| Resolution range (Å) | 50-2.3 | 50-3.4 | 50-3.55 |
| Beamline | ID-14-2 | BM-14 | BM-14 |

**Values in parentheses are for the highest resolution shells. Data were collected at the ESRF, Grenoble, France Example 3

Structural Determination of the VDCC β Subunit

Materials and Methods

Expression and Purification

Selenomethionine-substituted VDCC β functional core was prepared and crystallized for multiwavelength anomalous diffraction (MAD). Protein was produced in *E. coli* BL21 (DE3) as described in Example 1, by inhibition of the methionine pathway (Van Duyne, G. D., Standaert, R. F., Karplus, P. A., Schreiber, S. L., and Clardy, J. (1993). J Mol Biol 229, 105-124). An overnight starter culture was grown from a single transformed colony in 10% LB medium. LB media was removed prior to the introduction of 2 L of New Minimal Media (Budisa, N., Steipe, B., Demange, P., Eckerskorn, C., Kellermann, J., and Huber, R. (1995). High-level biosynthetic substitution of methionine in proteins by its analogs 2-aminohexanoic acid, selenomethionine, telluromethionine and ethionine in *Escherichia coli*. Eur J Biochem 230, 788-796), fortified with Kao and Michayluk vitamin solution (Sigma), and 100 µg/ml ampicillin and 34 µg/ml chloramphenicol. Cells were grown at 37° C. to OD600=0.3, whereupon the temperature was lowered to 16° C. Lysine, phenylalanine and threonine (100 mg/L), isoleucine, leucine and valine (50 mg/L) and DL-selenomethionine (50 mg/L) were added 45 min before induction (A600=0.6). Expression was induced with 200 µM IPTG over a 14 hr period. Purification of the SeMet protein was similar to that of the native protein (Example 2), except that 5 mM β-ME was added to all solutions to prevent oxidation. The efficiency of SeMet incorporation was confirmed by mass spectrometry.

Crystallization and Structure Determination

SeMet protein crystals were grown at 19° C. by hanging drop vapor diffusion with conditions near those of native protein (Example 1). Equal volumes (1-2 µl) of diluted frozen stock protein (6-12 mg/ml) were mixed with reservoir solution containing 1-4% PEG 20K, 0.1 M Bicine pH 9, 1-3% MPD and 5 mM β-mercaptoethanol. Orthorhombic crystals were allowed to grow for no longer than 20 hr, then cryoprotected by sequential dilutions with mother liquor added with 35% glycerol. The crystals were mounted in cryoloops and flash frozen with liquid N2.

For co-crystallization of VDCC β functional core and purified AID peptide, equal volumes of equimolar (1-2 µl; 300 µM) protein (SEQ ID NO: 20 and 21, respectively) and AID peptide, having an amino acid sequence of QQLEEDLR-GYMSWITQGE (SEQ ID NO: 22) were mixed and equilibrated for 30 min. This solution was screened by hanging drops and gave co-crystals at about the same conditions as described above. Co-crystals have the same space group symmetry as protein crystals with similar unit cell dimensions.

Diffraction data for the SeMet protein crystals and the co-crystals were measured at the ESRF, under standard cryogenic conditions, and processed with HKL software package (Otwinowski, Z., and Minor, W. (1997). Method Enzymol 276, 307-326). A three-wavelength MAD experiment was performed on a single SeMet protein crystal. The anomalous absorption peak, followed by its inflection point and a remote with some anomalous signal were chosen for the wavelengths Scaled data sets for each wavelength were then rescaled by local scaling and 6 selenium sites located using SOLVE (Terwilliger, T. C. (2003). SOLVE and RESOLVE: automated structure solution and density modification. Methods Enzymol 374, 22-37). A clear heavy atom solution was obtained and heavy atom parameters refined to produce experimental phases, using SOLVE. These phases were then used for density modification by RESOLVE (Terwilliger, T. C. (2003). SOLVE and RESOLVE: automated structure solution and density modification. Methods Enzymol 374, 22-37) or SOLOMON (Abrahams, J. P., and Leslie, A. G. W. (1996). Methods used in the structure determination of bovine mitochondrial F-1 ATPase. Acta Cryst D52, 30-42), whose outputs gave two complementary 2.9 Å electron density maps of high quality. A model of β was built with O (Jones et al., 1991), and refined with CNS (Br•nger, A. T., Adams, P. D., Clore, G. M., DeLano, W. L., Gros, P., Grosse-Kunstleve, R. W., Jiang, J.-S., Kuszewki, J., Nilges, M., Pannu, N. S., et al (1998). Acta Cryst D54, 905-921). At that point, the model was refined against a non-isomorphous 2.3 Å data set using CNS, REFMAC5 (Murshudov, G. N., Vagin, A. A., and Dodson, E. J. (1997). Acta Crystallographica Section D—Biological Crystallography 53, 240-255) and ARP (Morris, R. J., Perraakis, A., and Lamzin, V. S. (2003). Methods Enzymol 374, 229-244) with rounds of model rebuilding.

The β/AID peptide co-crystal structure was determined by molecular replacement. Initially, a 3 Å data set measured on the home source was used. Despite the similarity in crystal forms between the β crystals and the co-crystals, rigid body refinement was not sufficient to obtain electron density maps showing the peptide. After molecular replacement (MR) with CNS, using the 2.3 Å refined β model, clear and unmistakable density was found for the bound peptide. MR was required due to a shift of β by several angstroms along one axis. The peptide model was built including changes in β and refined against a 2.2 Å data set collected subsequently. Rounds of model building and refinement were performed as above. The current models have good stereochemistry (Laskowski, R. A., Macarthur, M. W., Moss, D. S., and Thornton, J. M. (1993) Journal of Applied Crystallography 26, 283-291). Both of these crystals utilized protein that bears a mutation in domain I which does not affect function (Opatowsky, Y. Chomsky-Hecht, O., Kang, M. G., Campbell, K. P., and Hirsch, J. A. (2003). J Biol Chem 278, 52323-52332).

Diffraction data were collected on an alternative crystal form described in Example 1. This crystal form diffracts to about 3.5 Å and could be obtained using both WT and mutant protein, as well as truncated linker core and linkerless core proteins. Electron density maps and models of the truncated linker core and linkerless tetragonal crystals were obtained by MR with MolRep (Vagin, A., and Teplyakov, A. (2000). Acta Crystallogr D Biol Crystallogr 56 Pt 12, 1622-1624), using the 2.3 Å b model. No gross changes in structure were noted between the WT and mutant protein nor between truncated linker core and linkerless core proteins.

In Vitro Binding Assays

Full length VDCC β2a was mutated by the QuikChange (Stratagene) method. The altered sequence was confirmed by DNA sequencing. Expression, purification, and fluorescence polarization measurements of the mutant proteins were as described (Opatowsky, Y., Chomsky-Hecht, O., Kang, M. G., Campbell, K. P., and Hirsch, J. A. (2003). J Biol Chem 278, 52323-52332).

CD Spectroscopy

CD measurements were performed with an Aviv CD spectrometer model 202. Spectra were measured over the range of 260-180 nm at a scan rate of 1 nm/sec. For all measurements, a cell with 1 mm path length was used. The raw data were corrected by subtracting the contribution of the buffer to the CD signal. Data were smoothed and converted to molar ellipticity units. Concentration of peptide was obtained using its predicted extinction coefficient at 280 nm.

Molecular Graphics

Figure 4:
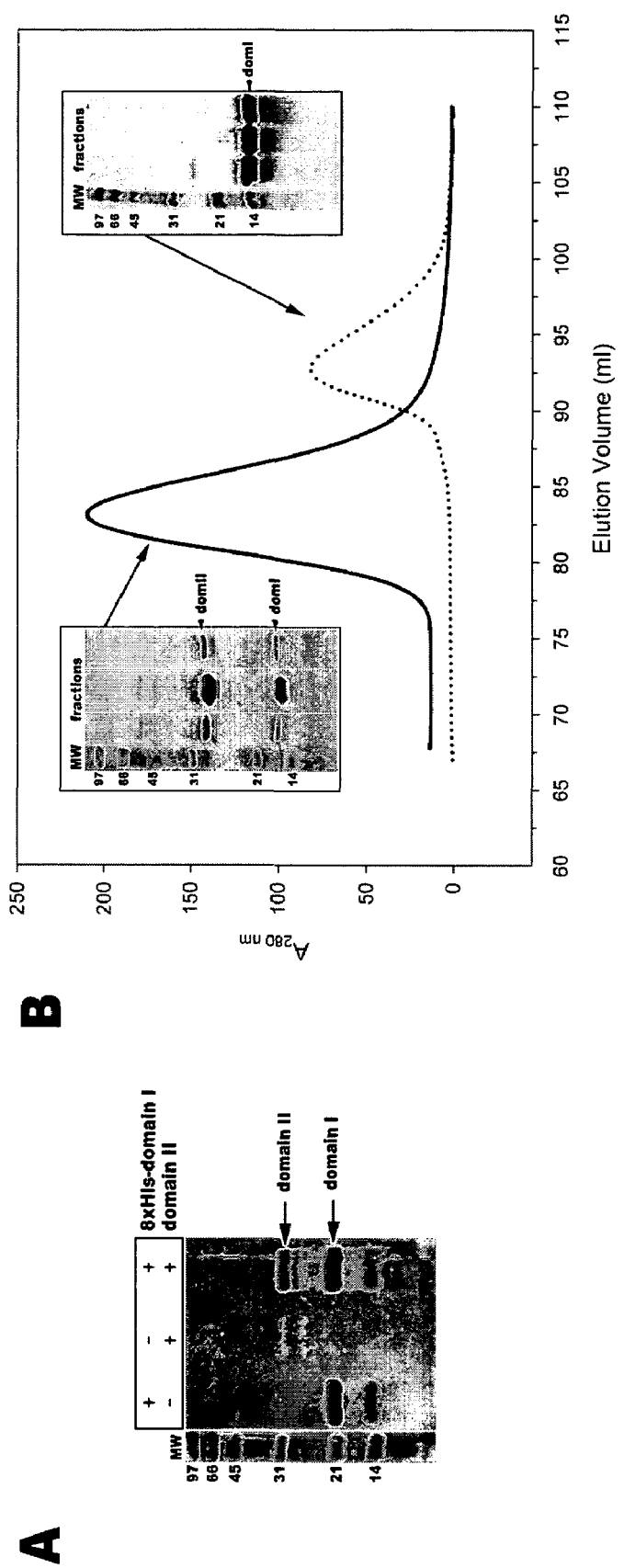
FIG. 4 demonstrates the association of domains I and II. A: SDS-PAGE gel stained with Coomassie blue of a pull-down assay. Domain I contains a polyhistidine tag with which it was immobilized, while domain II was without a tag. Protein input is indicated by the key above the gel. Left lane: domain I pulled down with metal-chelate resin; center lane: domain II pulled down with metal-chelate resin (there is a small degree of non-specific binding to the resin); right lane: immobilized domain I after incubation with domain II for 20 minutes in phosphate buffer pH 7, containing 300 mM NaCl. Protein input was on the order of 10 mg protein. Beads were washed five times with buffer for all experiments. The output of domain II in the right lane is dramatically enhanced due to association with domain I. Relevant bands are labeled. B: Gel-filtration chromatography elution profile of domain I alone (dotted trace) and linkerless core (solid line), after digestion with TEV protease to remove the linker. The insets show SDS-PAGE gels of the relevant central fractions from each peak. As can be easily discerned, domain I and II coelute in the left-hand peak. Relevant bands are labeled (Opatowsky et al., 2003).

FIGS. 4, 6a,b and 7a were prepared with Bobscript (Esnouf, R. M. (1999). Acta Crystallographica Section D-Biological Crystallography 55, 938-940), and Raster3D (Merritt, E. A., and Bacon, D. J. (1997). Macromolecular Crystallography, Pt B 277, 505-524). FIGS. 6c and 7b were prepared with Molscript (Kraulis, P. J. (1991). Journal of Applied Crystallography 24, 946-950) and Raster3D. FIG. 9 was prepared with GRASP (Nicholls, A., Sharp, K. A., and Honig, B. (1991). Proteins 11, 281-296).

Results

The structure of the rabbit β2a functional core was determined by performing a three-wavelength MAD experiment on a single crystal of seleno-methionine substituted protein. Experimental electron density maps at 2.9 Å resolution enabled tracing of the complete molecule with two clearly defined domains, as anticipated. Refinement of the atomic model continued with a 2.3 Å data set. Diffraction data to 3.5 Å was obtained for an alternate crystal form, crystallized with two different forms of the functional core protein. A molecular replacement solution and refinement indicated no significant conformational differences between this and its higher resolution form. Thus, the analysis focused on the high-resolution form.

Subsequently, the β functional core was co-crystallized with an 18 residue AID peptide, whose sequence was: QQLEEDLRGYMSWITQGE (SEQ ID NO: 22), derived from the CaV1.1 AID sequence. This crystal form unequivocally contained the AID peptide, as β also co-crystallized with a fluorescein-labeled peptide that gave bright yellow crystals Diffraction data on the co-crystal was measured to a $d_{min}$ of 2.2 Å (data presented in Table 3) and the is AID/β complex structure was determined by molecular replacement and rounds of model building and refinement.

The initial electron density for the bound AID peptide is shown in FIG. 15a. Residues 25-33 (N-terminus), 203-217 (truncated linker), and 416-422 (C-terminus) of β are not visible in the electron density maps.

Example 4

Molecular Architecture of the VDCC β Subunit

The structure revealed a two-domain construction (FIG. 12a), with dimensions 94×54×48 Å, and defined a new variant of the membrane associated guanylate kinase (MAGUK) protein family.

MAGUK proteins have been defined generally by sequences that contain three modules, namely PDZ, SH3 and guanylate kinase-like (Guk) domains. Many of the members contain multiples of the PDZ domain. Family members function as molecular scaffolds, using their various domains to

TABLE 3

Crystallographic data of the β functional core co-crystallized with AID

| Data collection and phasing statistics | SeMet β | | | β | AID/β |
|---|---|---|---|---|---|
| | $\lambda_1$ | $\lambda_2$ | $\lambda_3$ | β | AID/β |
| Wavelength (Å) | 0.97905 | 0.97854 | 0.90499 | 0.933 | 1.0069 |
| Space group | | $P2_12_12$ | | $P2_12_12$ | $P2_12_12$ |
| Unit-cell | | a = 74.3 | | a = 74.1 | a = 72.8 |
| Parameters | | b = 165.7 | | b = 163.8 | b = 168.3 |
| (Å) | | c = 34.6 | | c = 34.8 | c = 34.2 |
| Total reflections | 84558 | 76495 | 63504 | 71732 | 89743 |
| Unique reflections | 9990 | 9969 | 8411 | 18271 | 19123 |
| Completeness (%)[a] | 98.8 (94.7) | 98.6 (93.7) | 95.4 (91.8) | 92.8 (87.9) | 85.7 (63.2) |
| $R_{merge}$ (%)[a,b] | 6.1 (21) | 5.9 (19) | 9.6 (21) | 4.8 (31) | 5.9 (31) |
| I/σ[a] | 30.1 (9.7) | 29.1 (9.7) | 25.6 (10.5) | 15.4 (4.3) | 21.3 (3.9) |
| Resolution range (Å) | 50-2.9 | 50-2.9 | 50-3.0 | 50-2.3 | 50-2.2 |
| f'/f'' | −9.68/2.30 | −7.68/4.10 | −1.33/3.14 | | |
| Phasing power (anomalous) | 0.4 | 0.6 | 0.6 | | |
| Phasing power (dispersive) | 0.5 ($\lambda_2$ vs $\lambda_1$) | 0.7 ($\lambda_3$ vs $\lambda_2$) | 0.9 ($\lambda_1$ vs $\lambda_3$) | | |
| Figures of Merit | | 0.39 | | | |
| Beamline (ESRF) | BM-14 | BM-14 | BM-14 | ID-14-2 | ID-29 |

| Refinement statistics | β | AID/β |
|---|---|---|
| No. of reflections (working/test) | 17294/935 | 17364/1283 |
| $d_{min}$ (Å) | 2.3 | 2.2 |
| $R_{work}/R_{free}$ | 26.1/28.8 | 23.3/28.8 |
| Rms deviation from ideality | | |
| Bond lengths (Å) | 0.013 | 0.011 |
| Bond angles | 1.3° | 1.3° |
| B factors (Å²) (rmsd of bonded atoms-main/side chain) | 1.1/2.1 | 1.0/2.1 |
| Average B factor (Å²) | 62.7 | 44.1 |
| No. of protein atoms/solvent | 2299/91 | 2541/130 |

[a]Values for the highest resolution shell are given in parentheses
[b]Rmerge = ΣhklΣi|Ihkl, i − <I>hkI|/ΣhklΣi|Ihkl, i| where Ihkl is the intensity of a reflection and <I>hkl is the average of all observations of this reflection and its symmetry equivalents create a web of protein-protein interactions at, or near, the cell membrane. While VDCC β lacked the PDZ domain, its domain I is most similar to MAGUK SH3 domains, and its domain II is a GuK-like domain. β, in fact, represents a minimal MAGUK, having eliminated the PDZ domain and dressed down its GuK domain as detailed below. The structure of the SH3 and GuK domains from a MAGUK protein, PSD-95, served as a critical foil for the structural analysis (McGee, A. W., Dakoji, S. R., Olsen, O., Bredt, D. S., Lim, W. A., and Prehoda, K. E. (2001). Mol Cell 8, 1291-1301; Tavares, G. A., Panepucci, E. H., and Brunger, A. T. (2001). Structural characterization of the intramolecular interaction between the SH3 and guanylate kinase domains of PSD-95. Mol Cell 8, 1313-1325).

The structure of domain I resembles an "adorned" SH3 domain. The fold is shown schematically in FIG. 12b. Long α-helices are appended to the module's amino-terminus and as an insertion between the fourth and fifth strands. Strand E belongs formally to the SH3 architecture while it is nominally part of domain II since limited proteolysis removes the polypeptide connecting helix 2 to strand E, leaving it with the latter domain. Helix 1, not seen in PSD-95, is found in the β structure to partially unwind towards the visible end of its N-terminus. Helix 2 is present in PSD-95 but with a somewhat different orientation. The RMS deviation after superposition between domain I and the Crk SH3 domain (Wu et al., 1995) is 1.3 Å for 52 Ca atoms while the RMSD between domain I and the SH3 of PSD is 1.3 Å for 61 Ca atoms.

A significant difference between domain I, and the SH3 fold, lies in β's unusually long extended RT-loop. Using its length, as seen in FIG. 6a, the β RT-loop takes a different conformation than that of PSD-95, folding in toward the n-Src loop and interacting with W104, thereby occluding the canonical polyproline binding groove. Both helices 1 and 2 make important interactions with parts of the SH3 fold. Helix 1 (E46, A49, L53) contains hydrophobic interactions with the RT loop (residues 80-84) and strands A, B, C and D so that it is well integrated into the fold. At the same time, helix 2 interacts with the hydrophobic core of the domain through interactions from its side chains L125 and M128. Thus, helix 2 projects outward from the SH3 fold precisely where the polyproline lies in its groove on the superposed Crk SH3 domain. Moreover, L125 anchors the helix at about the same position of conserved hydrophobic residues in polyproline ligands i.e. the amino terminus of helix 2 uses similar structural determinants to anchor itself to the domain as do canonical SH3 ligands.

Domain II has strong structural homology to GuK and the GuK-like domains found in MAGUKs (FIG. 14b), and in general, to the P-loop kinase superfamily. The GuK fold has three subdomains: the core, comprised of a parallel five-stranded β-sheet sandwiched by five helices, the mononucleotide binding (NMP) subdomain and the helical lid subdomain. VDCC β contains both the core and lid subdomains but substitutes the NMP subdomain with a structurally unrelated subdomain of about the same length, comprising several short helices, which we have called the "ear" lobe (FIG. 15b). In contrast, the MAGUKs retained the NMP subdomain, comprising a three-stranded sheet and two helices including the ability to bind mononucleotides, in some cases. The RMSD between domain II and yeast Guk (Stehle and Schulz, 1992) is 1.6 Å for 128 Ca atoms and between PSD-95 GuK is 2.2 Å for 86 Ca atoms. These superpositions underline the stronger resemblance of β domain II in the two relevant subdomains to yGuK versus PSD-95.

Since β lacks the NMP subdomain, it is not expected to bind GMP but it remains possible that the ear lobe will bind a small molecule since it does create clefts between itself and the central sheet and itself and strand 5 of domain 1. Another important difference between β and GuK or PSD-95 is the P-loop, also known as the Walker A box, which connects strand 1 and helix 1. As seen in FIG. 13a and FIG. 14b, β's P-loop is significantly longer than PSD and GuK. P loops in the kinase family are important for the binding of ATP phosphate moieties used for phosphotransfer. The composition and conformation of β's loop is pivotal for binding its target as described below. The lid subdomain is retained in all three structures in different orientations. β's lid orientation most closely approximates that of apoGuK (open) versus that of GuK with ADP bound (closed) and PSD-95 (very closed). The difference in orientation may have important consequences for protein target binding. Finally, ATP will not bind A, as β lacks an essential arginine, R131 in yGuK, required for nucleotide binding in all guanylate kinases. In β, the arginine has been replaced with a leucine. This crucial structural difference between GuK and β predicts that phosphotransferase activity has been lost by β and most probably the whole MAGUK family.

How do the two domains interact and how does that organization compare to PSD-95? Strand E of domain I is covalently linked by a short four residue turn to domain II. In addition, other interactions include hydrogen bonds from domain II helix 5 made with the distal loop of domain I. Side chains from the ear lobe and a turn before strand 4 of domain II interact with strand E of domain I. While the individual domains and topology are similar to PSD-95, the actual 3D picture is quite different. Due to PSD-95's very long strand E, the nature of the domain apposition varies. PSD-95's strand F couples with strand E, but is derived from the PSD-95 GuK domain. This is absent in β. The drastically different domain orientation is visualized in FIG. 6c where we have superposed the GuK-like domains. In addition, the domain interface in β is more intimate, burying more accessible surface area (1500 Å2 versus 1200 Å2) than for PSD-95.

Example 5

Protein-Protein Interaction Paradigm for GuKs

Materials and Methods

The GuK domain of the MAGUK family acts as a novel protein-protein interaction domain. Its function is required since several mutant phenotypic alleles of the founding member of the family, *Drosophila* Discs large (dlg) encode truncated proteins which have their GuK domain deleted. Subsequently, several instances of GuK domains from MAGUK proteins have been shown to bind to various protein targets. Some of the target proteins are motor proteins, used for transporting cargoes to various cellular locations. However, it is unknown how the GuK domains bind these targets.

The AID peptide is found bound to β domain II, consistent with earlier studies that had defined a region of interaction with the AID. The AID forms an α-helix that nestles into a groove on the protein, shaped by the juxtaposition of the lid subdomain and the core subdomain P-loop, helix 1, strand 5 and helix 5. Thus, the AID binds in the same location as does ATP in GuK, visualized in FIG. 14b. Perhaps even more striking, is the superposition of the adenosine moiety from ATP or ADP and the W369 of the AID. While the helical cylinder fits into the groove, the AID has two legs stapling it down. One leg consists of W369 and I370 W369 binds in a deep pit on the domain II surface and makes many interactions with domain II residues (summarized in FIG. 15b). The stereochemistry of W369 is crucial. Most importantly, its Nε1 makes a hydrogen bond to the main chain carbonyl of M246 on β. Consequently, one can easily justify its absolute conservation (FIG. 12b). The second leg consists of G365 and Y366. Y366 is buried completely, making van der Waals interactions with β. Concomitantly, its hydroxyl group makes bifurcated hydrogen-bonds to two water molecules. These, in turn, mediate hydrogen-bonds to β main chain carbonyl (389) or amine (345) groups. These residues are absolutely conserved except in the AID of the electric ray where the glycine is replaced with an arginine. The balance of connections involves van der Waals or hydrophobic interactions. Importantly, interactions between AID and domain II are not localized to one region in sequence space of β so that earlier definitions of the β interacting domain (BID), residues 218 to 250 i.e. strand E of domain I and strand 1, P-loop, and half of helix 1 of domain II are misleading. Three regions in sequence space contribute to the AID binding site, so that for proper binding of the AID one requires almost the complete domain II.

Complexation of the AID with β results in the burial of 1640 Å2 of accessible surface area. The average value for buried surface area amongst protein-protein interaction interfaces is around 1600 Å2. However, the nature of the interface is somewhat unusual. Janin and coworkers, in a survey of protein-protein interaction interfaces, arrived at average number of hydrogen bonds and the amino acid propensity in these interfaces (Lo Conte, L., Chothia, C., and Janin, J. (1999). J Mol Biol 285, 2177-2198). They find that these interfaces are more polar and involve more hydrogen bonds and ion pairs than protein interiors. In this way, the AID/β interface more resembles a protein interior. There are a paucity of hydrogen bonds (four, two being solvent mediated, versus an average of ten), one probable ion pair, and almost all of the remaining interactions are van der Waals or hydrophobic interactions. The β residues in the interface are almost entirely non-polar, while we do not detect a large number of solvent molecules in the interface.

The binding of β to mutagenized AID sequences has been investigated extensively in earlier work. Results of these studies are summarized in FIG. 15c and complement our structural data. They underline the exquisite specificity of W369 and the importance of Y366 and I370. Perturbation of these residues essentially abrogates binding. In general, the importance of residues for binding correlates well their relative burial upon association as computed from the crystal structure. Interestingly, mutation of Gly365 to arginine does not negate binding, suggesting that β will accommodate a bulkier side chain. The sequence conservation of glycine and its stereochemistry may be explained though the dynamics of complexation, described below. Changes in other residues, particularly those of the AID's solvent exposed helical face have little effect on binding.

Mutagenesis of the β subunit and examination of the effects on AID association is less extensive. The BID had several residues mutated (De Waard et al., 1994). Those that had no effect on binding may be rationalized via the structure since they are far from the binding site. Two prolines that were changed to arginines but are distal from the binding site and affected binding should disrupt the protein folding since they are buried. We have characterized two new mutations of β that were designed based on the structure, M246 and L392. M246 is found towards the C-terminal end of the BID, and L392 in the N-terminal end of helix 5. Both residues were changed to alanine and binding constants to AID peptide measured by fluorescence polarization. Both mutants lowered the affinity by one to two orders of magnitude (WT: KD=26±6 nM; M246: 1.7±0.3 mM; L392: 0.34±0.04 mM). These results corroborate our structural data that show the binding site to be composed of sequences outside of the BID.

A comprehensive search of the PDB, using FlexProt (Shatsky et al., 2002), for complexes that showed similarity to the AID/β interface led us to one hit. The crystal structure of the plasmid maintenance system from S. pyogenes constitutes a complex of the z toxin bound to its antitoxin e (Meinhart et al., 2003). While the RMSD is 1.8 Å for 82 out of 183 Cα atoms with a four percent sequence identity, the mode of interaction and even the general architecture of the toxin is quite similar to β's domain II. The toxin has a P-loop kinase fold and generated the proposal that it acts as a phosphotransferase. Mutation of residues putatively required for enzymatic activity abrogated toxicity, suggesting that the catalytic function is responsible for its killing potential. The antitoxin apparently acts by binding the toxin with its first helix inserting into the groove between the toxin's lid and core subdomains. Aromatics bury themselves into positions overlapping, in superpositions, that of W369 and the adenosine base of ATP/ADP of the GuKs.

The comparative structural analysis of the GuK fold lead us to the conclusion that this widely extant protein fold, found in every type of organism, evolved from an enzyme with phosphotransferase capacity to a protein-protein interaction module, losing on its way catalytic activity. Moreover, its ligand-binding site was resculptured to enable protein-protein interactions. Striking examples of this resculpturing are the change of the absolutely required arginine (in yGuK, Arg131) into a leucine in β and the protein target using aromatic side chains in the place of the nucleotide base. In the case of z toxin, catalytic activity is retained and the protein-protein interface facilitates inhibition, while in the case of VDCC β, catalytic activity has been lost to an interface which obtains high affinity and stable binding for its protein target. We propose that the MAGUK family uses the same strategy for binding its protein targets through its GuK domain.

Example 6

VDCC Assembly

The structural determinations herein have important implications for understanding VDCC functional aspects. One aspect, its mechanism for chaperoning the channel has been well-described. It has been shown that the α1 I-II linker contains an endoplasmic retention signal. β then successfully competes with an unknown ER retention protein in binding the linker via the AID, thereby masking the retention signal. This frees the channel to exit the ER and move ultimately to the plasma membrane with β still attached.

Given the crystallographic data that the AID is in an α-helical conformation in the complex, it is important to determine the secondary structure when alone in solution. To address this question, a circular dichroism (CD) spectrum of the peptide was measured. The spectrum, shown in FIG. 16, indicates a random coil structure. This implies that, at least in our in vitro system, the AID peptide undergoes a coil to helix transition during its association with β. We then measured the helical propensity of the AID peptide, by taking a CD spectrum with the peptide in a mixed water/trifluorethanol solution. The spectrum shows significant helical formation. Based on these data, it seems reasonable to posit that the AID associates with β in a coil conformation and undergoes a helical transition upon reaching its high affinity bound state. This hypothesis is consistent with several observations.

One, the nature of the protein-protein interface is largely non-polar and provides the ideal environment for a folding surface, akin to the lower dielectric characteristic of the mixed water/trifluorethanol solvent in the CD measurements. Such an environment is markedly more favorable energetically for the peptide backbone to make its hydrogen-bonds than when faced with an aqueous environment.

Two, the binding kinetics measured for the AID with β ($k_{on}$~2·6·105 M−1·s−1; $k_{off}$~5·10$^{-3}$ s$^{-1}$) suggest that the association is not a diffusion-controlled rigid body fast reaction ($k_{on}$~10$^7$ M$^{-1}$·s$^{-1}$) (Schreiber, G. (2002). Curr Opin Struct Biol 12, 41-47). The values are consistent with a folding step wherein the AID encounters β, low affinity binding occurs and then the AID folds into its helix conformation, locking in the high affinity-binding mode with its myriad interactions. Binding reversibility was established both in vitro and in situ as assessed by electrophysiological assays (Restituito, S., Cens, T., Rousset, M., and Charnet, P. (2001). Biophys J 81, 89-96). In this vein, reversibility could be prevented in an AID mutant replacing the glycine with arginine. Since the data indicates that the AID folds onto β, the conserved glycine provides the reversibility by its low helical propensity.

Three, an established method for detecting AID/β binding uses overlay assays wherein a fusion protein bearing the AID sequence is electrophoresed in a SDS system, transferred to nitrocellulose and labeled β protein is used to probe the filter (Marquart, A. F. V. (1997). FEBS Letters 407, 137-140; Pragnell, M., De Waard, M., Mori, Y., Tanabe, T., Snutch, T. P., and Campbell, K. P. (1994). Nature 368, 67-70). Despite the denaturing manner by which the AID is treated, β succeeds in binding avidly, suggesting that it can associate while the AID is initially unfolded.

Thus, β acts not merely as chaperone, accompanying α1 through the trafficking/processing pathway but also as a chaperonin for the I-II linker section of the channel. Such activity plays a role in ensuring the fidelity of channel assembly. Moreover, helix induction does not occur just in the AID site. Importantly, the protein sequence of the I-II linker, starting from the C-terminal end of membrane domain I i.e. the end of its S6 through the AID sequence motif, is predicted to be one long α-helix by all secondary structure algorithms tested, thus β association with the I-II linker induces helix formation of the AID that is then propagated towards the S6 helix along the polypeptide sequence of the I-II linker.

Example 7

Channel Structure and Function

Several groups have recently made progress towards elucidating the physical organization of VDCCs, using electron microscopy (Murata et al., 2001; Serysheva et al., 2002; Wang et al., 2003; Wolf et al., 2003). A monomeric complex has area dimensions of 110-150×120-165 Å. Identification of the extracellular α2δ has been made, along with a localization of β. The dimensions of the β functional core would fit well into the density. The β subunit, considering its elongated shape, comprises a significant fraction of the intracellular mass of the channel. This observation may be visualized in FIG. 17a, where a schematic α1 subunit has been drawn to an estimated scale with β bound to the α1 I-II linker that contains the AID.

Voltage dependent channels feature two salient molecular characteristics: (i) they are highly ion selective; (ii) they enable permeation of these ions in reaction to the membrane electrical potential. Gating is controlled by the interaction the between voltage sensor (S1-4) subdomain and the helical pore subdomain (S5-6). The conformation of the pore in closed (Kcsa) and open (MthK) positions is known for K+ channels. In order to transition between these two conformational states, it appears that S5 moves, induced by the voltage sensor, which in turn creates lateral torque on S6, causing its helix to bend near a glycine and move out radially, opening the channel. Using this information as a structural template, the S6 of the α1 membrane domain I is followed immediately by the I-II linker. The I-II linker starts with an absolutely conserved sequence (GEF), with the AID positioned exactly 22 residues later in all cases and whose intervening sequences are highly conserved (FIG. 13b). This structure is bound in a noncovalent but stable manner to β. We infer that VDCC gating is not exclusively controlled physically by the voltage-sensor and the pore-lining helices but rather by a complex, conserved and exact physical organization of those elements with the intracellular domains like the I-II linker/β complex. Thus, intracellular elements impinge directly on gating in a manner partially akin to the MthK, KirBac and the Girk channels, gated by ligand binding of intracellular domains.

How might these intracellular elements like the I-II linker/β complex impinge on gating? The AID-β complex structure demonstrates that the AID and β almost seamlessly fuse into a united surface. The resulting electrostatic potential produced shows that β domain II has a patch of negative potential (FIG. 17b), coincident and contiguous to the locale of AID binding. This patch will react to changes in the electrostatic potential of the surrounding environment as a result of membrane depolarization and the channel opening with its flux of $Ca^{2+}$ ions diffusing from the channel mouth. Hence, the bound β reconfigures the electrostatics of the intracellular side of the channel. Secondly, β orders a part of the channel physically connected to its gate, essentially changing its shape, length and mechanical properties, such as rigidity. Thirdly, through β binding, the gate is now connected to a linker with much greater mass and depending on isoform constrained in its movement by its own independent attachment to the membrane.

Of the known modulatory effects of β, one common denominator is that β seems to shift the equilibrium towards the open channel state i.e. activation. All three aspects of the I-II linker/β just described should facilitate this effect. Upon depolarization, the I-II linker/β negative patch may move in reaction to the changing electrostatic potential of α1, supplementing the radial torque on S6 from the voltage sensor. The presumed helical conformation will lend the requisite rigidity for any movements of the AID-β particle to be communicated to the gate. Also, the additional mass weighing on membrane domain I may destabilize the closed conformation of its S6. Thus, β's action on the channel state is best categorized as allosteric modulation.

Regarding channel inactivation and its kinetics, our structural model fits well with current models that propose a hinged-lid mechanism (Stotz et al., 2004). Here, the AID/β surface serves as the lid, the channel opens, $Ca^{2+}$ accumulates at the mouth, and attracts the lid by Coulombic forces and in coordination with $Ca^{2+}$-dependent inactivation determinants of the α1 C-terminus. Subsequently, residues in the AID that are solvent exposed i.e. those not involved in binding β and other residues of the linker find their receptor site possibly in the channel mouth, thereby blocking ion flow and inactivating the channel. According to this inactivation mechanism, the hinge, which enables the lid to swivel may be located at the link between S6 and the I-II linker i.e. the conserved glycine sequence at its start. Another prediction of this model will be the slowing of inactivation if β's movement is constrained through its N-terminus since the "lid" would then not be able to move as easily towards the channel mouth. This notion then explains the slow inactivation of β2α, whose N-terminus is anchored in the membrane by palmitoylation. When the palmitoylation site is mutated, inactivation parameters resemble that of the other isoforms and splice variants.

The structure of β determined represents only part of the molecule. For β3, the functional core represents about 70 percent of the molecule while it is less for the other isoforms. Many studies have demonstrated functions encoded by regions outside of the core, such as inactivation, influenced by the N-terminus or the linker between β domain I and II. Likewise, the C-terminus whose size and sequence varies dramatically between isoforms has been shown to be important for binding other sites on the α1 subunit. The functional core architecture, therefore, maintains the central functions of the molecule. At the same time, extraneous polypeptide regions elaborate functional specificity. Furthermore, functional specificity may be tuned not only by isoform but also by splicing alterations. These splicing permutations fall outside the core architecture.

The molecular architecture of the β functional core indicates that this protein has evolved to maximize protein-protein interactions with other partners. Recent examples of novel proteins that associate with β are the members of the small G-protein subfamily, Gem, Rad, and Rem, and HP1g, involved in gene silencing, indicating its role as nexus of some of the signaling pathways tied to calcium.

What is claimed is:

1. A crystallized voltage-dependent calcium channel (VDCC) β2a subunit functional core, wherein the crystal effectively diffracts X-rays for the determination of the atomic coordinates of the VDCC β2a subunit functional core to a resolution of better than 5.0 Angstroms, wherein said crystal is made by vapor diffusion from a VDCC β2a subunit functional core protein concentrated to 12 mg/ml with: a) a reservoir solution of 1.6 M ammonium sulfate, 0.1 M Hepes pH 7.0, 5 mM β-mercaptoethanol and grown at 4° C., or b) a reservoir solution of 3% PEG 20,000, 0.1 M Bicine pH 9, 0.1 M NaCl, 5 mM β-mercaptoethanol and grown at 19° C. and wherein the amino acid sequence of said VDCC β2a subunit functional core has at least 95% identity to SEQ ID NO: 20 or SEQ ID NO: 21, or at least 95% identity to either of said sequences without the four amino acid linker located at residues 114-117 of SEQ ID NO: 20 or 21.

2. The crystal of claim 1, wherein the voltage-dependent calcium channel β2a functional core is a member of the membrane associated guanylate kinase protein family.

3. The crystal of claim 1, wherein the voltage-dependent calcium channel β2a functional core has secondary structural elements that include five beta strands and two helices in the N-terminal domain, designated as strands A, B, C, D, and F, and alpha helices 1 and 2, and five beta strands and eight alpha helices in the C-terminal domain designated as strands 1, 2, 3, 4, and 5, and alpha helices α1, α2, α3, α4.1, α4.2, α5, E1, E2 and E3.

4. A crystallized voltage-dependent calcium channel (VDCC) β2a subunit functional core in complex with an α1 interaction domain (AID) peptide; wherein said AID peptide has at least 92% sequence identity to SEQ ID NO: 22 and wherein the sequence of said VDCC β2a functional core is as set forth in SEQ ID NO: 21; wherein the crystal effectively diffracts X-rays for the determination of the atomic coordinates of said VDCC β2a functional core:AID complex to a resolution of better than 5.0 Angstroms, and wherein said crystal is made by vapor diffusion from protein stocks of 6-12 mg/mi and a reservoir solution of 1-4% PEG 20K, 0.1 M Bicine pH 9, 1-3% 2-methyl-2,4-pentanediol (MPD) and 5 mM β-mercaptoethanol and grown at 19° C.

5. The crystal of claim 4, wherein the voltage-dependent calcium channel β2a functional core is a member of the membrane associated guanylate kinase protein family.

6. The crystal of claim 4, wherein the voltage-dependent calcium channel β2a functional core has secondary structural elements that include five beta strands and two helices in the N-terminal domain, designated as strands A, B, C, D, and F, and alpha helices 1 and 2, and five beta strands and eight alpha helices in the C-terminal domain designated as strands 1, 2, 3, 4, and 5, and alpha helices α1, α2, α3, α4.1, α4.2, α5, E1, E2 and E3.

7. A crystallized voltage-dependent calcium channel (VDCC) β2a subunit functional core in complex with an ccl interaction domain (AID) peptide; wherein the sequence of said AID peptide is as set forth in SEQ ID NO: 22 and wherein said VDCC β2a functional core has at least 95% identity to SEQ ID NO: 21; wherein the crystal effectively diffracts X-rays for the determination of the atomic coordinates of said VDCC β2a functional core:AID complex to a resolution of better than 5.0 Angstroms, and wherein said crystal is made by vapor diffusion from protein stocks of 6-12 mg/ml and a reservoir solution of 1-4% PEG 20K, 0.1 M Bicine pH 9, 1-3% 2-methyl-2,4-pentanediol (MPD) and 5 mM β-mercaptoethanol and grown at 19° C.

8. The crystal of claim 7, wherein the voltage-dependent calcium channel β2a functional core is a member of the membrane associated guanylate kinase protein family.

9. The crystal of claim 7, wherein the voltage-dependent calcium channel β2a functional core has secondary structural elements that include five beta strands and two helices in the N-terminal domain, designated as strands A, B, C, D, and E, and alpha helices 1 and 2, and five beta strands and eight alpha helices in the C-terminal domain designated as strands 1, 2, 3, 4, and 5, and alpha helices α1, α2, α3, α4.1, α4.2, α5, E1, E2 and E3.

10. A crystallized voltage-dependent calcium channel (VDCC) β2a subunit functional core, wherein the crystal effectively diffracts X-rays for the determination of the atomic coordinates of the VDCC β2a functional core to a resolution of better than 5.0 Angstroms, said crystal characterized as:
   a. Form I of a crystallized VDCC β2a functional core, wherein said crystal has a space group of $P4_12_12$ with unit cell dimensions of a=b=75.6 Å, c=164.4 Å and α=β=γ=90°; or
   b. Form II of a crystallized VDCC β2a functional core, wherein said crystal has a space group of $P2_12_12$, with unit cell dimensions of a=74.Å, b=163.8Å, c=34.8 Å and α=β=γ=90°;
wherein the amino acid sequence of said VDCC β2a functional core is SEQ ID NO: 21.

11. The crystal of claim 10, wherein the voltage-dependent calcium channel β2a functional core is a member of the membrane associated guanylate kinase protein family.

12. The crystal of claim 10, wherein the voltage-dependent calcium channel β2a functional core has secondary structural elements that include five beta strands and two helices in the N-terminal domain, designated as strands A, B, C, D, and F, and alpha helices 1 and 2, and five beta strands and eight alpha helices in the C-terminal domain designated as strands 1, 2, 3, 4, and 5, and alpha helices α1, α2, α3, α4.1, α4.2, α5, E1, E2 and E3.

13. A crystallized voltage-dependent calcium channel (VDCC) β2a subunit functional core, wherein the crystal effectively diffracts X-rays for the determination of the atomic coordinates of the VDCC β2a functional core to a resolution of better than 5.0 Angstroms, wherein said crystal has a space group of $P4_12_12$ with unit cell dimensions of a=b=76.5 Å, c=164.9 Å and α=β=γ=90°; and the β2a functional core is the amino acid sequence SEQ ID NO: 20 without the four amino acid linker located at residues 114-117.

14. The crystal of claim 13, wherein the voltage-dependent calcium channel β2a functional core is a member of the membrane associated guanylate kinase protein family.

15. The crystal of claim 13, wherein the voltage-dependent calcium channel β2a functional core has secondary structural elements that include five beta strands and two helices in the N-terminal domain, designated as strands A, B, C, D, and F, and alpha helices 1 and 2, and five beta strands and eight alpha helices in the C-terminal domain designated as strands 1, 2, 3, 4, and 5, and alpha helices α1, α2, α3, α4.1, α4.2, α5, E1, E2 and E3.

16. A crystallized voltage-dependent calcium channel (VDCC) β2a subunit functional core in complex with an ccl interaction domain (AID) peptide, wherein the crystal effectively diffracts X-rays for the determination of the atomic coordinates of the VDCC β2a functional core:AID peptide complex to a resolution of better than 5.0 Angstroms wherein said crystal has a space group of $P2_12_12$, with unit cell dimensions of a=72.8 Å, b=168.3 Å, c=34.2 Å and α=β=γ=90°; and wherein the amino acid sequence of said AID peptide is SEQ ID NO: 22 and the β2a functional core is SEQ ID NO: 21.

17. The crystal of claim 16, wherein the voltage-dependent calcium channel β2a functional core is a member of the membrane associated guanylate kinase protein family.

18. The crystal of claim 16, wherein the voltage-dependent calcium channel β2a functional core has secondary structural elements that include five beta strands and two helices in the N-terminal domain, designated as strands A, B, C, D, and F, and alpha helices 1 and 2, and five beta strands and eight alpha helices in the C-terminal domain designated as strands 1, 2, 3, 4, and 5, and alpha helices α1, α2, α3, α4.1, α4.2, α5, E1, E2 and E3.

* * * * *

```
                          SEQUENCE LISTING

<160> NUMBER OF SEQ ID NOS: 38

<210> SEQ ID NO 1
   <211> LENGTH: 31
   <212> TYPE: DNA
   <213> ORGANISM: Rattus norvegicus

<400> SEQUENCE: 1
gcgcggatcc tatgacgact cctacgtccc c                                      31

<210> SEQ ID NO 2
   <211> LENGTH: 31
   <212> TYPE: DNA
   <213> ORGANISM: Rattus norvegicus

<400> SEQUENCE: 2
gcgcggatcc tatgacgact cctacgtgcc c                                      31

<210> SEQ ID NO 3
   <211> LENGTH: 30
   <212> TYPE: DNA
   <213> ORGANISM: Oryctolagus cuniculus

<400> SEQUENCE: 3
gcgcggatcc cttgacaggc acctcgcggc                                        30

<210> SEQ ID NO 4
   <211> LENGTH: 25
   <212> TYPE: DNA
   <213> ORGANISM: Oryctolagus cuniculus

<400> SEQUENCE: 4
cgccgaattc tcattggcgg atgta                                             25

<210> SEQ ID NO 5
   <211> LENGTH: 34
   <212> TYPE: DNA
   <213> ORGANISM: Oryctolagus cuniculus

<400> SEQUENCE: 5
gcgcggatcc agccgtccat ccgattcaga tgtg                                   34

<210> SEQ ID NO 6
   <211> LENGTH: 37
   <212> TYPE: DNA
   <213> ORGANISM: Oryctolagus cuniculus
```

-continued

<400> SEQUENCE: 6
gcgcgaattc tcactttgct ctctgttcat gctgtag        37

<210> SEQ ID NO 7
<211> LENGTH: 34
<212> TYPE: DNA
<213> ORGANISM: Oryctolagus cuniculus

<400> SEQUENCE: 7
gcgcggatcc cactccaaag agaaagaat gccc            34

<210> SEQ ID NO 8
<211> LENGTH: 37
<212> TYPE: DNA
<213> ORGANISM: Oryctolagus cuniculus

<400> SEQUENCE: 8
gcgcgaattc tcaaaggaga gggttgggga gattgct        37

<210> SEQ ID NO 9
<211> LENGTH: 34
<212> TYPE: DNA
<213> ORGANISM: Oryctolagus cuniculus

<400> SEQUENCE: 9
cgcggaattc ctttgctctc tgttcatgct gtag           34

<210> SEQ ID NO 10
<211> LENGTH: 38
<212> TYPE: DNA
<213> ORGANISM: Oryctolagus cuniculus

<400> SEQUENCE: 10
cggaattcaa gcttcactcc aaagagaaaa gaatgccc       38

<210> SEQ ID NO 11
<211> LENGTH: 40
<212> TYPE: DNA
<213> ORGANISM: Oryctolagus cuniculus

<400> SEQUENCE: 11
ttatactagc ggccgctcaa aggagagggt tggggagatt     40

<210> SEQ ID NO 12
<211> LENGTH: 50
<212> TYPE: DNA
<213> ORGANISM: Oryctolagus cuniculus

<400> SEQUENCE: 12
cgcggaattc gaaaacctgt actttcaggg ccaagggaaa ttctactcca    50

<210> SEQ ID NO 13
<211> LENGTH: 50
<212> TYPE: DNA
<213> ORGANISM: Oryctolagus cuniculus

<400> SEQUENCE: 13
cgcggaattc gccctgaaag tacaggtttt cgggtgacgt tacactgttt    50

<210> SEQ ID NO 14
<211> LENGTH: 20
<212> TYPE: PRT

<213> ORGANISM: Oryctolagus cuniculus

<400> SEQUENCE: 14

Gly Gly Gln Gln Leu Glu Glu Asp Leu Arg Gly Tyr Asn Ser Trp Ile
1               5                   10                  15

Thr Gln Gly Glu
            20

<210> SEQ ID NO 15
<211> LENGTH: 20
<212> TYPE: PRT
<213> ORGANISM: Oryctolagus cuniculus

<400> SEQUENCE: 15

Gly Gly Gln Gln Leu Glu Glu Asp Leu Arg Gly Ser Asn Ser Trp Ile
1               5                   10                  15

Thr Gln Gly Glu
            20

<210> SEQ ID NO 16
<211> LENGTH: 34
<212> TYPE: DNA
<213> ORGANISM: Oryctolagus cuniculus

<400> SEQUENCE: 16
gcgcggatcc agccgtccat ccgattcaga tgtg                            34

<210> SEQ ID NO 17
<211> LENGTH: 34
<212> TYPE: DNA
<213> ORGANISM: Oryctolagus cuniculus

<400> SEQUENCE: 17
cgcggaattc ctttgctctc tgttcatgct gtag                            34

<210> SEQ ID NO 18
<211> LENGTH: 38
<212> TYPE: DNA
<213> ORGANISM: Oryctolagus cuniculus

<400> SEQUENCE: 18
cggaattcaa gcttcactcc aaagagaaaa gaatgccc                        38

<210> SEQ ID NO 19
<211> LENGTH: 40
<212> TYPE: DNA
<213> ORGANISM: Oryctolagus cuniculus

<400> SEQUENCE: 19
ttatactagc ggccgctcaa aggagagggt tggggagatt                      40

<210> SEQ ID NO 20
<211> LENGTH: 337
<212> TYPE: PRT
<213> ORGANISM: Oryctolagus cuniculus

<400> SEQUENCE: 20

Ser Arg Pro Ser Asp Ser Asp Val Ser Leu Glu Glu Asp Arg Glu Ala
1               5                   10                  15

Val Arg Arg Glu Ala Glu Arg Gln Ala Gln Ala Gln Leu Glu Lys Ala
            20                  25                  30

Lys Thr Lys Pro Val Ala Phe Ala Val Arg Thr Asn Val Ser Tyr Ser

-continued

```
            35                  40                  45
Ala Ala His Glu Asp Asp Val Pro Val Pro Gly Met Ala Ile Ser Phe
 50                  55                  60

Glu Ala Lys Asp Phe Leu His Val Lys Glu Lys Phe Asn Asn Asp Trp
 65                  70                  75                  80

Trp Ile Gly Arg Leu Val Lys Glu Gly Cys Glu Ile Gly Phe Ile Pro
                 85                  90                  95

Ser Pro Val Lys Leu Glu Asn Met Arg Leu Gln His Glu Gln Arg Ala
             100                 105                 110

Lys Glu Phe Lys Leu His Ser Lys Glu Lys Arg Met Pro Phe Phe Lys
         115                 120                 125

Lys Thr Glu His Thr Pro Pro Tyr Asp Val Val Pro Ser Met Arg Pro
     130                 135                 140

Val Val Leu Val Gly Pro Ser Leu Lys Gly Tyr Glu Val Thr Asp Met
145                 150                 155                 160

Met Gln Lys Ala Leu Phe Asp Phe Leu Lys His Arg Phe Glu Gly Arg
                165                 170                 175

Ile Ser Ile Thr Arg Val Thr Ala Asp Ile Ser Leu Ala Lys Arg Ser
            180                 185                 190

Val Leu Asn Asn Pro Ser Lys His Ala Ile Ile Glu Arg Ser Asn Thr
        195                 200                 205

Arg Ser Ser Leu Ala Glu Val Gln Ser Glu Ile Glu Arg Ile Phe Glu
    210                 215                 220

Leu Ala Arg Thr Leu Gln Leu Val Val Leu Asp Ala Asp Thr Ile Asn
225                 230                 235                 240

His Pro Ala Gln Leu Ser Lys Thr Ser Leu Ala Pro Ile Val Val Tyr
                245                 250                 255

Val Lys Ile Ser Ser Pro Lys Val Leu Gln Arg Leu Ile Lys Ser Arg
            260                 265                 270

Gly Lys Ser Gln Ala Lys His Leu Asn Val Gln Met Val Ala Ala Asp
        275                 280                 285

Lys Leu Ala Gln Cys Pro Pro Glu Leu Phe Asp Val Ile Leu Asp Glu
    290                 295                 300

Asn Gln Leu Glu Asp Ala Cys Glu His Leu Ala Asp Tyr Leu Glu Ala
305                 310                 315                 320

Tyr Trp Lys Ala Thr His Pro Pro Ser Ser Asn Leu Pro Asn Pro Leu
                325                 330                 335

Leu

<210> SEQ ID NO 21
<211> LENGTH: 337
<212> TYPE: PRT
<213> ORGANISM: Oryctolagus cuniculus

<400> SEQUENCE: 21

Ser Arg Pro Ser Asp Ser Asp Val Ser Leu Glu Glu Asp Arg Glu Ala
 1               5                  10                  15

Val Arg Arg Glu Ala Glu Arg Gln Ala Gln Ala Gln Leu Glu Lys Ala
             20                  25                  30

Lys Thr Lys Pro Val Ala Phe Ala Val Arg Thr Asn Val Ser Tyr Ser
         35                  40                  45

Ala Ala His Glu Asp Asp Val Pro Val Pro Gly Met Ala Ile Ser Phe
     50                  55                  60

Glu Ala Lys Asp Phe Leu His Val Lys Glu Lys Phe Asn Asn Asp Trp
```

```
                65                  70                  75                  80
Trp Ile Gly Arg Leu Val Lys Glu Gly Cys Glu Ile Gly Phe Ile Pro
                    85                  90                  95

Ser Arg Val Lys Leu Glu Asn Met Arg Leu Gln His Glu Gln Arg Ala
                100                 105                 110

Lys Glu Phe Lys Leu His Ser Lys Glu Lys Arg Met Pro Phe Phe Lys
            115                 120                 125

Lys Thr Glu His Thr Pro Pro Tyr Asp Val Pro Ser Met Arg Pro
        130                 135                 140

Val Val Leu Val Gly Pro Ser Leu Lys Gly Tyr Glu Val Thr Asp Met
145                 150                 155                 160

Met Gln Lys Ala Leu Phe Asp Phe Leu Lys His Arg Phe Glu Gly Arg
                165                 170                 175

Ile Ser Ile Thr Arg Val Thr Ala Asp Ile Ser Leu Ala Lys Arg Ser
                180                 185                 190

Val Leu Asn Asn Pro Ser Lys His Ala Ile Ile Glu Arg Ser Asn Thr
            195                 200                 205

Arg Ser Ser Leu Ala Glu Val Gln Ser Glu Ile Glu Arg Ile Phe Glu
        210                 215                 220

Leu Ala Arg Thr Leu Gln Leu Val Val Leu Asp Ala Asp Thr Ile Asn
225                 230                 235                 240

His Pro Ala Gln Leu Ser Lys Thr Ser Leu Ala Pro Ile Val Val Tyr
                245                 250                 255

Val Lys Ile Ser Ser Pro Lys Val Leu Gln Arg Leu Ile Lys Ser Arg
                260                 265                 270

Gly Lys Ser Gln Ala Lys His Leu Asn Val Gln Met Val Ala Ala Asp
            275                 280                 285

Lys Leu Ala Gln Cys Pro Pro Glu Leu Phe Asp Val Ile Leu Asp Glu
        290                 295                 300

Asn Gln Leu Glu Asp Ala Cys Glu His Leu Ala Asp Tyr Leu Glu Ala
305                 310                 315                 320

Tyr Trp Lys Ala Thr His Pro Pro Ser Ser Asn Leu Pro Asn Pro Leu
                325                 330                 335

Leu

<210> SEQ ID NO 22
<211> LENGTH: 18
<212> TYPE: PRT
<213> ORGANISM: Oryctolagus cuniculus

<400> SEQUENCE: 22

Gln Gln Leu Glu Glu Asp Leu Arg Gly Tyr Met Ser Trp Ile Thr Gln
1               5                   10                  15

Gly Glu

<210> SEQ ID NO 23
<211> LENGTH: 606
<212> TYPE: PRT
<213> ORGANISM: Oryctolagus cuniculus

<400> SEQUENCE: 23

Met Leu Asp Arg His Leu Ala Ala Pro His Thr Gln Gly Leu Val Leu
1               5                   10                  15

Glu Gly Ser Ala Asp Ser Tyr Thr Ser Arg Pro Ser Asp Ser Asp Val
            20                  25                  30
```

-continued

```
Ser Leu Glu Glu Asp Arg Glu Ala Val Arg Arg Glu Ala Glu Arg Gln
         35                  40                  45

Ala Gln Ala Gln Leu Glu Lys Ala Lys Thr Lys Pro Val Ala Phe Ala
     50                  55                  60

Val Arg Thr Asn Val Ser Tyr Ser Ala Ala His Glu Asp Asp Val Pro
 65                  70                  75                  80

Val Pro Gly Met Ala Ile Ser Phe Glu Ala Lys Asp Phe Leu His Val
                 85                  90                  95

Lys Glu Lys Phe Asn Asn Asp Trp Trp Ile Gly Arg Leu Val Lys Glu
            100                 105                 110

Gly Cys Glu Ile Gly Phe Ile Pro Ser Pro Val Lys Leu Glu Asn Met
        115                 120                 125

Arg Leu Gln His Glu Gln Arg Ala Lys Gln Gly Lys Phe Tyr Ser Ser
    130                 135                 140

Lys Ser Gly Gly Asn Ser Ser Ser Leu Gly Asp Ile Val Pro Ser
145                 150                 155                 160

Ser Arg Lys Ser Thr Pro Pro Ser Ser Ala Ile Asp Ile Asp Ala Thr
                165                 170                 175

Gly Leu Asp Ala Glu Glu Asn Asp Ile Pro Ala Asn His Arg Ser Pro
            180                 185                 190

Lys Pro Ser Ala Asn Ser Val Thr Ser Pro His Ser Lys Glu Lys Arg
        195                 200                 205

Met Pro Phe Phe Lys Lys Thr Glu His Thr Pro Pro Tyr Asp Val Val
    210                 215                 220

Pro Ser Met Arg Pro Val Val Leu Val Gly Pro Ser Leu Lys Gly Tyr
225                 230                 235                 240

Glu Val Thr Asp Met Met Gln Lys Ala Leu Phe Asp Phe Leu Lys His
                245                 250                 255

Arg Phe Glu Gly Arg Ile Ser Ile Thr Arg Val Thr Ala Asp Ile Ser
            260                 265                 270

Leu Ala Lys Arg Ser Val Leu Asn Asn Pro Ser Lys His Ala Ile Ile
        275                 280                 285

Glu Arg Ser Asn Thr Arg Ser Ser Leu Ala Glu Val Gln Ser Glu Ile
    290                 295                 300

Glu Arg Ile Phe Glu Leu Ala Arg Thr Leu Gln Leu Val Val Leu Asp
305                 310                 315                 320

Ala Asp Thr Ile Asn His Pro Ala Gln Leu Ser Lys Thr Ser Leu Ala
                325                 330                 335

Pro Ile Val Val Tyr Val Lys Ile Ser Ser Pro Lys Val Leu Gln Arg
            340                 345                 350

Leu Ile Lys Ser Arg Gly Lys Ser Gln Ala Lys His Leu Asn Val Gln
        355                 360                 365

Met Val Ala Ala Asp Lys Leu Ala Gln Cys Pro Pro Glu Leu Phe Asp
    370                 375                 380

Val Ile Leu Asp Glu Asn Gln Leu Glu Asp Ala Cys Glu His Leu Ala
385                 390                 395                 400

Asp Tyr Leu Glu Ala Tyr Trp Lys Ala Thr His Pro Pro Ser Ser Asn
                405                 410                 415

Leu Pro Asn Pro Leu Leu Ser Arg Thr Leu Ala Thr Ser Ala Leu Pro
            420                 425                 430

Val Ser Pro Thr Leu Ala Ser Asn Ser Gln Gly Ser Gln Gly Asp Gln
        435                 440                 445

Arg Thr Asp Arg Ser Ala Pro Ala Arg Ser Ala Ser Gln Ala Glu Glu
```

-continued

```
              450                 455                 460
Glu Pro Cys Leu Glu Pro Ala Lys Lys Ser Gln His Arg Ser Ser Ser
465                 470                 475                 480

Ser Ala Pro His His Asn His Arg Ser Gly Thr Ser Arg Gly Leu Ser
                485                 490                 495

Arg Gln Glu Thr Phe Asp Ser Glu Thr Gln Glu Ser Arg Asp Ser Ala
                500                 505                 510

Tyr Val Glu Pro Lys Glu Asp Tyr Ser His Glu His Val Asp His Tyr
            515                 520                 525

Ala Pro His Arg Asp His Asn His Arg Asp Glu Thr His Arg Ser Ser
            530                 535                 540

Asp His Arg His Arg Glu Thr Arg His Arg Ser Arg Asp Met Asp Arg
545                 550                 555                 560

Glu Gln Asp His Asn Glu Cys Asn Lys Gln Arg Ser Arg His Lys Ser
                565                 570                 575

Lys Asp Arg Tyr Cys Asp Lys Asp Gly Glu Val Ile Ser Lys Lys Arg
            580                 585                 590

Asn Glu Ala Gly Glu Trp Asn Arg Asp Val Tyr Ile Arg Gln
            595                 600                 605

<210> SEQ ID NO 24
<211> LENGTH: 484
<212> TYPE: PRT
<213> ORGANISM: homo sapiens

<400> SEQUENCE: 24

Met Tyr Asp Asp Ser Tyr Val Pro Gly Phe Glu Asp Ser Glu Ala Gly
1               5                   10                  15

Ser Ala Asp Ser Tyr Thr Ser Arg Pro Ser Leu Asp Ser Asp Val Ser
                20                  25                  30

Leu Glu Glu Asp Arg Glu Ser Ala Arg Arg Glu Val Glu Ser Gln Ala
            35                  40                  45

Gln Gln Gln Leu Glu Arg Ala Lys His Lys Pro Val Ala Phe Ala Val
        50                  55                  60

Arg Thr Asn Val Ser Tyr Cys Gly Val Leu Asp Glu Glu Cys Pro Val
65                  70                  75                  80

Gln Gly Ser Gly Val Asn Phe Glu Ala Lys Asp Phe Leu His Ile Lys
                85                  90                  95

Glu Lys Tyr Ser Asn Asp Trp Trp Ile Gly Arg Leu Val Lys Glu Gly
                100                 105                 110

Gly Asp Ile Ala Phe Ile Pro Ser Pro Gln Arg Leu Glu Ser Ile Arg
            115                 120                 125

Leu Lys Gln Glu Gln Lys Ala Arg Arg Ser Gly Asn Pro Ser Ser Leu
        130                 135                 140

Ser Asp Ile Gly Asn Arg Arg Ser Pro Pro Ser Leu Ala Lys Gln
145                 150                 155                 160

Lys Gln Lys Gln Ala Glu His Val Pro Pro Tyr Asp Val Val Pro Ser
                165                 170                 175

Met Arg Pro Val Val Leu Val Gly Pro Ser Leu Lys Gly Tyr Glu Val
                180                 185                 190

Thr Asp Met Met Gln Lys Ala Leu Phe Asp Phe Leu Lys His Arg Phe
            195                 200                 205

Asp Gly Arg Ile Ser Ile Thr Arg Val Thr Ala Asp Leu Ser Leu Ala
        210                 215                 220
```

```
Lys Arg Ser Val Leu Asn Asn Pro Gly Lys Arg Thr Ile Ile Glu Arg
225                 230                 235                 240

Ser Ser Ala Arg Ser Ile Ala Glu Val Gln Ser Glu Ile Glu Arg
            245                 250                 255

Ile Phe Glu Leu Ala Lys Ser Leu Gln Leu Val Val Leu Asp Ala Asp
                260                 265                 270

Thr Ile Asn His Pro Ala Gln Leu Ala Lys Thr Ser Leu Ala Pro Ile
            275                 280                 285

Ile Val Phe Val Lys Val Ser Ser Pro Lys Val Leu Gln Arg Leu Ile
290                 295                 300

Arg Ser Arg Gly Lys Ser Gln Met Lys His Leu Thr Val Gln Met Met
305                 310                 315                 320

Ala Tyr Asp Lys Leu Val Gln Cys Pro Pro Glu Ser Phe Asp Val Ile
                325                 330                 335

Leu Asp Glu Asn Gln Leu Glu Asp Ala Cys Glu His Leu Ala Glu Tyr
            340                 345                 350

Leu Glu Val Tyr Trp Arg Ala Thr His His Pro Ala Pro Gly Pro Gly
        355                 360                 365

Leu Leu Gly Pro Pro Ser Ala Ile Pro Gly Leu Gln Asn Gln Gln Leu
    370                 375                 380

Leu Gly Glu Arg Gly Glu His Ser Pro Leu Glu Arg Asp Ser Leu
385                 390                 395                 400

Met Pro Ser Asp Glu Ala Ser Glu Ser Ser Arg Gln Ala Trp Thr Gly
                405                 410                 415

Ser Ser Gln Arg Ser Ser Arg His Leu Glu Glu Asp Tyr Ala Asp Ala
            420                 425                 430

Tyr Gln Asp Leu Tyr Gln Pro His Arg Gln His Thr Ser Gly Leu Pro
                435                 440                 445

Ser Ala Asn Gly His Asp Pro Gln Asp Arg Leu Leu Ala Gln Asp Ser
            450                 455                 460

Glu His Asn His Ser Asp Arg Asn Trp Gln Arg Asn Arg Pro Trp Pro
465                 470                 475                 480

Lys Asp Ser Tyr

<210> SEQ ID NO 25
<211> LENGTH: 419
<212> TYPE: PRT
<213> ORGANISM: Anopheles gambiae

<400> SEQUENCE: 25

Gln Gln Gly Ser Ala Asp Ser Asn Tyr Ser Gln Pro Ser Ser Asp Leu
1               5                   10                  15

Ser Leu Asp Glu Glu Lys Glu Ser Leu Arg Arg Glu Lys Glu Arg Gln
            20                  25                  30

Ala Leu Gly Gln Leu Glu Lys Ala Arg Ser Lys Pro Val Ala Phe Ala
        35                  40                  45

Val Arg Thr Asn Val Ser Tyr Asp Gly Ser Leu Asp Asp Asp Ser Pro
50                  55                  60

Val His Gly Ser Ala Val Ser Phe Glu Val Gly Asp Phe Leu His Ile
65                  70                  75                  80

Lys Glu Lys Tyr Asp Asn Asn Trp Trp Ile Gly Arg Leu Val Lys Glu
                85                  90                  95

Gly Cys Glu Val Gly Phe Ile Pro Ser Pro Val Lys Leu Glu His Ile
                100                 105                 110
```

```
Arg Met Gln Ala Ser Ala Ala Arg Ser Ser Lys Leu Tyr Thr Ser Lys
        115                 120                 125

Gly Ser Ser Ser Gly Asn Leu Gly Ala Ser Gly Val Pro Gly Ala
    130                 135                 140

Glu Pro Ser Arg Gly Asp Asp Ser Asp Ser Met Gly Ala Ser Arg His
145                 150                 155                 160

Gly Lys Thr Pro Leu Ala Thr Pro Pro Thr Lys Glu Lys Arg Lys Pro
                165                 170                 175

Phe Phe Lys Lys Gln Glu Thr Ser Ser Pro Tyr Asp Val Val Pro Ser
            180                 185                 190

Met Arg Pro Val Val Leu Val Gly Pro Ser Leu Lys Gly Tyr Glu Val
        195                 200                 205

Thr Asp Met Met Gln Lys Ala Leu Phe Asp Phe Leu Lys His Arg Phe
    210                 215                 220

Glu Ser Arg Ile Ile Ile Thr Arg Val Gln Ala Asp Ile Ser Leu Ala
225                 230                 235                 240

Lys Arg Ser Leu Met Asn Asn Pro Ser Lys Arg Ala Ile Met Glu Arg
                245                 250                 255

Ser Asn Ser Arg Ser Ser Cys Leu Ala Glu Val Gln Ala Glu Ile Glu
            260                 265                 270

Arg Ile Phe Glu Leu Ala Arg Thr Leu Gln Leu Val Val Leu Asp Cys
        275                 280                 285

Asp Thr Ile Asn His Pro Ser Gln Leu Ala Lys Thr Ser Leu Ala Pro
    290                 295                 300

Thr Ile Val Tyr Leu Lys Ile Ala Ser Ser Lys Val Leu Gln Arg Leu
305                 310                 315                 320

Ile Lys Ser Arg Gly Lys Ala Gln Ala Lys Asn Leu Ser Val Gln Met
                325                 330                 335

Val Ala Ala Glu Lys Leu Ser Gln Cys Pro Pro Glu Met Phe Asp Val
            340                 345                 350

Ile Leu Asp Glu Asn Gln Leu Glu Glu Ala Cys Asn His Leu Ala Glu
        355                 360                 365

Tyr Leu Glu Ala Tyr Trp Arg Ala Thr His Pro Val Arg Pro Thr
    370                 375                 380

Pro Ser Val Pro Arg Pro Leu Pro Ser Gln Glu Ala Ser Pro Ser Gly
385                 390                 395                 400

Glu Gln Pro Gly Arg Met Gly Pro Pro Pro Thr Gly Arg Leu Phe
                405                 410                 415

Val Ser Thr

<210> SEQ ID NO 26
<211> LENGTH: 304
<212> TYPE: PRT
<213> ORGANISM: Mus musculus

<400> SEQUENCE: 26

Met Ala Gly Asn Phe Asp Ser Glu Glu Arg Ser Ser Trp Tyr Trp Gly
1               5                   10                  15

Arg Leu Ser Arg Gln Glu Ala Val Ala Leu Leu Gln Gly Gln Arg His
            20                  25                  30

Gly Val Phe Leu Val Arg Asp Ser Thr Ser Pro Gly Asp Tyr Val
        35                  40                  45

Leu Ser Val Ser Glu Asn Ser Arg Val Ser His Tyr Ile Ile Asn Ser
    50                  55                  60
```

```
Ser Gly Pro Arg Pro Val Pro Ser Pro Ala Gln Pro Pro
 65                  70                  75                  80

Gly Val Ser Pro Ser Arg Leu Arg Ile Gly Asp Gln Glu Phe Asp Ser
                 85                  90                  95

Leu Pro Ala Leu Leu Glu Phe Tyr Lys Ile His Tyr Leu Asp Thr Thr
            100                 105                 110

Thr Leu Ile Glu Pro Val Ala Arg Ser Arg Gln Gly Ser Gly Val Ile
        115                 120                 125

Leu Arg Gln Glu Glu Ala Glu Tyr Val Arg Ala Leu Phe Asp Phe Asn
    130                 135                 140

Gly Asn Asp Glu Glu Asp Leu Pro Phe Lys Lys Gly Asp Ile Leu Arg
145                 150                 155                 160

Ile Arg Asp Lys Pro Glu Glu Gln Trp Trp Asn Ala Glu Asp Ser Glu
                165                 170                 175

Gly Lys Arg Gly Met Ile Pro Val Pro Tyr Val Glu Lys Tyr Arg Pro
            180                 185                 190

Ala Ser Ala Ser Val Ser Ala Leu Ile Gly Gly Asn Gln Glu Gly Ser
        195                 200                 205

His Pro Gln Pro Leu Gly Gly Pro Glu Pro Gly Pro Tyr Ala Gln Pro
    210                 215                 220

Ser Val Asn Thr Pro Leu Pro Asn Leu Gln Asn Gly Pro Ile Tyr Ala
225                 230                 235                 240

Arg Val Ile Gln Lys Arg Val Pro Asn Ala Tyr Asp Lys Thr Ala Leu
                245                 250                 255

Ala Leu Glu Val Gly Glu Leu Val Lys Val Thr Lys Ile Asn Val Ser
            260                 265                 270

Gly Gln Trp Glu Gly Glu Cys Asn Gly Lys Arg Gly His Phe Pro Phe
        275                 280                 285

Thr His Val Arg Leu Leu Asp Gln Gln Asn Pro Asp Glu Asp Phe Ser
    290                 295                 300

<210> SEQ ID NO 27
<211> LENGTH: 187
<212> TYPE: PRT
<213> ORGANISM: Saccharomyces cerevisiae

<400> SEQUENCE: 27

Met Ser Arg Pro Ile Val Ile Ser Gly Pro Ser Gly Thr Gly Lys Ser
1               5                   10                  15

Thr Leu Leu Lys Lys Leu Phe Ala Glu Tyr Pro Asp Ser Phe Gly Phe
            20                  25                  30

Ser Val Ser Ser Thr Thr Arg Thr Pro Arg Ala Gly Glu Val Asn Gly
        35                  40                  45

Lys Asp Tyr Asn Phe Val Ser Val Asp Glu Phe Lys Ser Met Ile Lys
    50                  55                  60

Asn Asn Glu Phe Ile Glu Trp Ala Gln Phe Ser Gly Asn Tyr Tyr Gly
65                  70                  75                  80

Ser Thr Val Ala Ser Val Lys Gln Val Ser Lys Ser Gly Lys Thr Cys
                85                  90                  95

Ile Leu Asp Ile Asp Met Gln Gly Val Lys Ser Val Lys Ala Ile Pro
            100                 105                 110

Glu Leu Asn Ala Arg Phe Leu Phe Ile Ala Pro Pro Ser Val Glu Asp
        115                 120                 125

Leu Lys Lys Arg Leu Glu Gly Arg Gly Thr Glu Thr Glu Glu Ser Ile
    130                 135                 140
```

```
Asn Lys Arg Leu Ser Ala Ala Gln Ala Glu Leu Ala Tyr Ala Glu Thr
145                 150                 155                 160

Gly Ala His Asp Lys Val Ile Val Asn Asp Asp Leu Asp Lys Ala Tyr
            165                 170                 175

Lys Glu Leu Lys Asp Phe Ile Phe Ala Glu Lys
        180                 185
```

<210> SEQ ID NO 28
<211> LENGTH: 724
<212> TYPE: PRT
<213> ORGANISM: Rattus norvegicus

<400> SEQUENCE: 28

```
Met Asp Cys Leu Cys Ile Val Thr Thr Lys Lys Tyr Arg Tyr Gln Asp
1               5                   10                  15

Glu Asp Thr Pro Pro Leu Glu His Ser Pro Ala His Leu Pro Asn Gln
            20                  25                  30

Ala Asn Ser Pro Pro Val Ile Val Asn Thr Asp Thr Leu Glu Ala Pro
        35                  40                  45

Gly Tyr Glu Leu Gln Val Asn Gly Thr Glu Gly Glu Met Glu Tyr Glu
50                  55                  60

Glu Ile Thr Leu Glu Arg Gly Asn Ser Gly Leu Gly Phe Ser Ile Ala
65                  70                  75                  80

Gly Gly Thr Asp Asn Pro His Ile Gly Asp Asp Pro Ser Ile Phe Ile
                85                  90                  95

Thr Lys Ile Ile Pro Gly Gly Ala Ala Ala Gln Asp Gly Arg Leu Arg
            100                 105                 110

Val Asn Asp Ser Ile Leu Phe Val Asn Glu Val Asp Val Arg Glu Val
        115                 120                 125

Thr His Ser Ala Ala Val Glu Ala Leu Lys Glu Ala Gly Ser Ile Val
130                 135                 140

Arg Leu Tyr Val Met Arg Arg Lys Pro Pro Ala Glu Lys Val Met Glu
145                 150                 155                 160

Ile Lys Leu Ile Lys Gly Pro Lys Gly Leu Gly Phe Ser Ile Ala Gly
                165                 170                 175

Gly Val Gly Asn Gln His Ile Pro Gly Asp Asn Ser Ile Tyr Val Thr
            180                 185                 190

Lys Ile Ile Glu Gly Gly Ala Ala His Lys Asp Gly Arg Leu Gln Ile
        195                 200                 205

Gly Asp Lys Ile Leu Ala Val Asn Ser Val Gly Leu Glu Asp Val Met
210                 215                 220

His Glu Asp Ala Val Ala Ala Leu Lys Asn Thr Tyr Asp Val Val Tyr
225                 230                 235                 240

Leu Lys Val Ala Lys Pro Ser Asn Ala Tyr Leu Ser Asp Ser Tyr Ala
                245                 250                 255

Pro Pro Asp Ile Thr Thr Ser Tyr Ser Gln His Leu Asp Asn Glu Ile
            260                 265                 270

Ser His Ser Ser Tyr Leu Gly Thr Asp Tyr Pro Thr Ala Met Thr Pro
        275                 280                 285

Thr Ser Pro Arg Arg Tyr Ser Pro Val Ala Lys Asp Leu Leu Gly Glu
290                 295                 300

Glu Asp Ile Pro Arg Glu Pro Arg Arg Ile Val Ile His Arg Gly Ser
305                 310                 315                 320

Thr Gly Leu Gly Phe Asn Ile Val Gly Gly Glu Asp Gly Glu Gly Ile
```

-continued

```
                325                 330                 335
Phe Ile Ser Phe Ile Leu Ala Gly Gly Pro Ala Asp Leu Ser Gly Glu
            340                 345                 350
Leu Arg Lys Gly Asp Gln Ile Leu Ser Val Asn Gly Val Asp Leu Arg
            355                 360                 365
Asn Ala Ser His Glu Gln Ala Ile Ala Leu Lys Asn Ala Gly Gln
        370                 375                 380
Thr Val Thr Ile Ile Ala Gln Tyr Lys Pro Glu Glu Tyr Ser Arg Phe
385                 390                 395                 400
Glu Ala Lys Ile His Asp Leu Arg Glu Gln Leu Met Asn Ser Ser Leu
                405                 410                 415
Gly Ser Gly Thr Ala Ser Leu Arg Ser Asn Pro Lys Arg Gly Phe Tyr
            420                 425                 430
Ile Arg Ala Leu Phe Asp Tyr Asp Lys Thr Lys Asp Cys Gly Phe Leu
            435                 440                 445
Ser Gln Ala Leu Ser Phe Arg Phe Gly Asp Val Leu His Val Ile Asp
        450                 455                 460
Ala Gly Asp Glu Glu Trp Trp Gln Ala Arg Arg Val His Ser Asp Ser
465                 470                 475                 480
Glu Thr Asp Asp Ile Gly Phe Ile Pro Ser Lys Arg Arg Val Glu Arg
                485                 490                 495
Arg Glu Trp Ser Arg Leu Lys Ala Lys Asp Trp Gly Ser Ser Ser Gly
            500                 505                 510
Ser Gln Gly Arg Glu Asp Ser Val Leu Ser Tyr Glu Thr Val Thr Gln
            515                 520                 525
Met Glu Val His Tyr Ala Arg Pro Ile Ile Ile Leu Gly Pro Thr Lys
        530                 535                 540
Asp Arg Ala Asn Asp Asp Leu Leu Ser Glu Phe Pro Asp Lys Phe Gly
545                 550                 555                 560
Ser Cys Val Pro His Thr Thr Arg Pro Lys Arg Glu Tyr Glu Ile Asp
                565                 570                 575
Gly Arg Asp Tyr His Phe Val Ser Ser Arg Glu Lys Met Glu Lys Asp
            580                 585                 590
Ile Gln Ala His Lys Phe Ile Glu Ala Gly Gln Tyr Asn Ser His Leu
            595                 600                 605
Tyr Gly Thr Ser Val Gln Ser Val Arg Glu Val Ala Glu Gln Gly Lys
        610                 615                 620
His Cys Ile Leu Asp Val Ser Ala Asn Ala Val Arg Arg Leu Gln Ala
625                 630                 635                 640
Ala His Leu His Pro Ile Ala Ile Phe Ile Arg Pro Arg Ser Leu Glu
                645                 650                 655
Asn Val Leu Glu Ile Asn Lys Arg Ile Thr Glu Glu Gln Ala Arg Lys
            660                 665                 670
Ala Phe Asp Arg Ala Thr Lys Leu Glu Gln Glu Phe Thr Glu Cys Phe
            675                 680                 685
Ser Ala Ile Val Glu Gly Asp Ser Phe Glu Ile Tyr His Lys Val
        690                 695                 700
Lys Arg Val Ile Glu Asp Leu Ser Gly Pro Tyr Ile Trp Val Pro Ala
705                 710                 715                 720
Arg Glu Arg Leu

<210> SEQ ID NO 29
<211> LENGTH: 1873
```

```
<212> TYPE: PRT
<213> ORGANISM: homo sapiens

<400> SEQUENCE: 29

Met Glu Pro Ser Ser Pro Gln Asp Glu Gly Leu Arg Lys Lys Gln Pro
1               5                   10                  15

Lys Lys Pro Val Pro Glu Ile Leu Pro Ser Pro Arg Ala Leu Phe
            20                  25                  30

Cys Leu Thr Leu Glu Asn Pro Leu Arg Lys Ala Cys Ile Ser Ile Val
            35                  40                  45

Glu Trp Lys Pro Phe Glu Thr Ile Ile Leu Leu Thr Ile Phe Ala Asn
50                      55                  60

Cys Val Ala Leu Ala Val Tyr Leu Pro Met Pro Glu Asp Asp Asn Asn
65                  70                  75                  80

Ser Leu Asn Leu Gly Leu Glu Lys Leu Glu Tyr Phe Phe Leu Ile Val
                85                  90                  95

Phe Ser Ile Glu Ala Ala Met Lys Ile Ile Ala Tyr Gly Phe Leu Phe
            100                 105                 110

His Gln Asp Ala Tyr Leu Arg Ser Gly Trp Asn Val Leu Asp Phe Thr
            115                 120                 125

Ile Val Phe Leu Gly Val Phe Thr Val Ile Leu Glu Gln Val Asn Val
            130                 135                 140

Ile Gln Ser His Thr Ala Pro Met Ser Ser Lys Gly Ala Gly Leu Asp
145                 150                 155                 160

Val Lys Ala Leu Arg Ala Phe Arg Val Leu Arg Pro Leu Arg Leu Val
                165                 170                 175

Ser Gly Val Pro Ser Leu Gln Val Val Leu Asn Ser Ile Phe Lys Ala
            180                 185                 190

Met Leu Pro Leu Phe His Ile Ala Leu Leu Val Leu Phe Met Val Ile
            195                 200                 205

Ile Tyr Ala Ile Ile Gly Leu Glu Leu Phe Lys Gly Lys Met His Lys
210                 215                 220

Thr Cys Tyr Phe Ile Gly Thr Asp Ile Val Ala Thr Val Glu Asn Glu
225                 230                 235                 240

Glu Pro Ser Pro Cys Ala Arg Thr Gly Ser Gly Arg Arg Cys Thr Ile
                245                 250                 255

Asn Gly Ser Glu Cys Arg Gly Gly Trp Pro Gly Pro Asn His Gly Ile
            260                 265                 270

Thr His Phe Asp Asn Phe Gly Phe Ser Met Leu Thr Val Tyr Gln Cys
            275                 280                 285

Ile Thr Met Glu Gly Trp Thr Asp Val Leu Tyr Trp Val Asn Asp Ala
290                 295                 300

Ile Gly Asn Glu Trp Pro Trp Ile Tyr Phe Val Thr Leu Ile Leu Leu
305                 310                 315                 320

Gly Ser Phe Phe Ile Leu Asn Leu Val Leu Gly Val Leu Ser Gly Glu
                325                 330                 335

Phe Thr Lys Glu Arg Glu Lys Ala Lys Ser Arg Gly Thr Phe Gln Lys
            340                 345                 350

Leu Arg Glu Lys Gln Gln Leu Asp Glu Asp Leu Arg Gly Tyr Met Ser
            355                 360                 365

Trp Ile Thr Gln Gly Glu Val Met Asp Val Glu Asp Phe Arg Glu Gly
            370                 375                 380

Lys Leu Ser Leu Asp Glu Gly Gly Ser Asp Thr Glu Ser Leu Tyr Glu
385                 390                 395                 400
```

```
Ile Ala Gly Leu Asn Lys Ile Ile Gln Phe Ile Arg His Trp Arg Gln
            405                 410                 415

Trp Asn Arg Ile Phe Arg Trp Lys Cys His Asp Ile Val Lys Ser Lys
        420                 425                 430

Val Phe Tyr Trp Leu Val Ile Leu Ile Val Ala Leu Asn Thr Leu Ser
            435                 440                 445

Ile Ala Ser Glu His His Asn Gln Pro Leu Trp Leu Thr Arg Leu Gln
450                 455                 460

Asp Ile Ala Asn Arg Val Leu Leu Ser Leu Phe Thr Thr Glu Met Leu
465                 470                 475                 480

Met Lys Met Tyr Gly Leu Gly Leu Arg Gln Tyr Phe Met Ser Ile Phe
                485                 490                 495

Asn Arg Phe Asp Cys Phe Val Val Cys Ser Gly Ile Leu Glu Ile Leu
            500                 505                 510

Leu Val Glu Ser Gly Ala Met Thr Pro Leu Gly Ile Ser Val Leu Arg
        515                 520                 525

Cys Ile Arg Leu Leu Arg Ile Phe Lys Ile Thr Lys Tyr Trp Thr Ser
530                 535                 540

Leu Ser Asn Leu Val Ala Ser Leu Leu Asn Ser Ile Arg Ser Ile Ala
545                 550                 555                 560

Ser Leu Leu Leu Leu Leu Phe Leu Phe Ile Val Ile Phe Ala Leu Leu
                565                 570                 575

Gly Met Gln Leu Phe Gly Gly Arg Tyr Asp Phe Glu Asp Thr Glu Val
            580                 585                 590

Arg Arg Ser Asn Phe Asp Asn Phe Pro Gln Ala Leu Ile Ser Val Phe
        595                 600                 605

Gln Val Leu Thr Gly Glu Asp Trp Thr Ser Met Met Tyr Asn Gly Ile
    610                 615                 620

Met Ala Tyr Gly Gly Pro Ser Tyr Pro Gly Met Leu Val Cys Ile Tyr
625                 630                 635                 640

Phe Ile Ile Leu Phe Val Cys Gly Asn Tyr Ile Leu Leu Asn Val Phe
                645                 650                 655

Leu Ala Ile Ala Val Asp Asn Leu Ala Glu Ala Glu Ser Leu Thr Ser
            660                 665                 670

Ala Gln Lys Ala Lys Ala Glu Glu Lys Lys Arg Arg Lys Met Ser Lys
        675                 680                 685

Gly Leu Pro Asp Lys Ser Glu Glu Lys Ser Thr Met Ala Lys Lys
    690                 695                 700

Leu Glu Gln Lys Pro Lys Gly Glu Gly Ile Pro Thr Thr Ala Lys Leu
705                 710                 715                 720

Lys Ile Asp Glu Phe Glu Ser Asn Val Asn Glu Val Lys Asp Pro Tyr
                725                 730                 735

Pro Ser Ala Asp Phe Pro Gly Asp Asp Glu Glu Asp Glu Pro Glu Ile
            740                 745                 750

Pro Leu Ser Pro Arg Pro Arg Pro Leu Ala Glu Leu Gln Leu Lys Glu
        755                 760                 765

Lys Ala Val Pro Ile Pro Glu Ala Ser Ser Phe Phe Ile Phe Ser Pro
    770                 775                 780

Thr Asn Lys Ile Arg Val Leu Cys His Arg Ile Val Asn Ala Thr Trp
785                 790                 795                 800

Phe Thr Asn Phe Ile Leu Leu Phe Ile Leu Leu Ser Ser Ala Ala Leu
                805                 810                 815
```

-continued

```
Ala Ala Glu Asp Pro Ile Arg Ala Asp Ser Met Arg Asn Gln Ile Leu
            820                 825                 830

Lys His Phe Asp Ile Gly Phe Thr Ser Val Phe Thr Val Glu Ile Val
            835                 840                 845

Leu Lys Met Thr Thr Tyr Gly Ala Phe Leu His Lys Gly Ser Phe Cys
            850                 855                 860

Arg Asn Tyr Phe Asn Met Leu Asp Leu Leu Val Val Ala Val Ser Leu
865                 870                 875                 880

Ile Ser Met Gly Leu Glu Ser Ser Ala Ile Ser Val Val Lys Ile Leu
                885                 890                 895

Arg Val Leu Arg Val Leu Arg Pro Leu Arg Ala Ile Asn Arg Ala Lys
            900                 905                 910

Gly Leu Lys His Val Val Gln Cys Met Phe Val Ala Ile Ser Thr Ile
            915                 920                 925

Gly Asn Ile Val Leu Val Thr Thr Leu Leu Gln Phe Met Phe Ala Cys
            930                 935                 940

Ile Gly Val Gln Leu Phe Lys Gly Lys Phe Phe Arg Cys Thr Asp Leu
945                 950                 955                 960

Ser Lys Met Thr Glu Glu Glu Cys Arg Gly Tyr Tyr Tyr Val Tyr Lys
                965                 970                 975

Asp Gly Asp Pro Met Gln Ile Glu Leu Arg His Arg Glu Trp Val His
            980                 985                 990

Ser Asp Phe His Phe Asp Asn Val Leu Ser Ala Met Met Ser Leu Phe
            995                 1000                1005

Thr Val Ser Thr Phe Glu Gly Trp Pro Gln Leu Leu Tyr Lys Ala
            1010                1015                1020

Ile Asp Ser Asn Ala Glu Asp Val Gly Pro Ile Tyr Asn Asn Arg
            1025                1030                1035

Val Glu Met Ala Ile Phe Phe Ile Ile Tyr Ile Ile Leu Ile Ala
            1040                1045                1050

Phe Phe Met Met Asn Ile Phe Val Gly Phe Val Ile Val Thr Phe
            1055                1060                1065

Gln Glu Gln Gly Glu Thr Glu Tyr Lys Asn Cys Glu Leu Asp Lys
            1070                1075                1080

Asn Gln Arg Gln Cys Val Gln Tyr Ala Leu Lys Ala Arg Pro Leu
            1085                1090                1095

Arg Cys Tyr Ile Pro Lys Asn Pro Tyr Gln Tyr Gln Val Trp Tyr
            1100                1105                1110

Ile Val Thr Ser Ser Tyr Phe Glu Tyr Leu Met Phe Ala Leu Ile
            1115                1120                1125

Met Leu Asn Thr Ile Cys Leu Gly Met Gln His Tyr Asn Gln Ser
            1130                1135                1140

Glu Gln Met Asn His Ile Ser Asp Ile Leu Asn Val Ala Phe Thr
            1145                1150                1155

Ile Ile Phe Thr Leu Glu Met Ile Leu Lys Leu Met Ala Phe Lys
            1160                1165                1170

Ala Arg Gly Tyr Phe Gly Asp Pro Trp Asn Val Phe Asp Phe Leu
            1175                1180                1185

Ile Val Ile Gly Ser Ile Ile Asp Val Ile Leu Ser Glu Ile Asp
            1190                1195                1200

Thr Phe Leu Ala Ser Ser Gly Gly Leu Tyr Cys Leu Gly Gly Gly
            1205                1210                1215

Cys Gly Asn Val Asp Pro Asp Glu Ser Ala Arg Ile Ser Ser Ala
```

-continued

```
         1220                1225               1230
Phe Phe Arg Leu Phe Arg Val Met Arg Leu Ile Lys Leu Leu Ser
    1235                1240               1245

Arg Ala Glu Gly Val Arg Thr Leu Leu Trp Thr Phe Ile Lys Ser
    1250                1255               1260

Phe Gln Ala Leu Pro Tyr Val Ala Leu Leu Ile Val Met Leu Phe
    1265                1270               1275

Phe Ile Tyr Ala Val Ile Gly Met Gln Met Phe Gly Lys Ile Ala
    1280                1285               1290

Leu Val Asp Gly Thr Gln Ile Asn Arg Asn Asn Asn Phe Gln Thr
    1295                1300               1305

Phe Pro Gln Ala Val Leu Leu Leu Phe Arg Cys Ala Thr Gly Glu
    1310                1315               1320

Ala Trp Gln Glu Ile Leu Leu Ala Cys Ser Tyr Gly Lys Leu Cys
    1325                1330               1335

Asp Pro Glu Ser Asp Tyr Ala Pro Gly Glu Glu Tyr Thr Cys Gly
    1340                1345               1350

Thr Asn Phe Ala Tyr Tyr Tyr Phe Ile Ser Phe Tyr Met Leu Cys
    1355                1360               1365

Ala Phe Leu Val Ile Asn Leu Phe Val Ala Val Ile Met Asp Asn
    1370                1375               1380

Phe Asp Tyr Leu Thr Arg Asp Trp Ser Ile Leu Gly Pro His His
    1385                1390               1395

Leu Asp Glu Phe Lys Ala Ile Trp Ala Glu Tyr Asp Pro Glu Ala
    1400                1405               1410

Lys Gly Arg Ile Lys His Leu Asp Val Val Thr Leu Leu Arg Arg
    1415                1420               1425

Ile Gln Pro Pro Leu Gly Phe Gly Lys Phe Cys Pro His Arg Val
    1430                1435               1440

Ala Cys Lys Arg Leu Val Gly Met Asn Met Pro Leu Asn Ser Asp
    1445                1450               1455

Gly Thr Val Thr Phe Asn Ala Thr Leu Phe Ala Leu Val Gly Thr
    1460                1465               1470

Ala Leu Lys Ile Lys Thr Glu Gly Asn Phe Glu Gln Ala Asn Glu
    1475                1480               1485

Glu Leu Arg Ala Ile Ile Lys Lys Ile Trp Lys Arg Thr Ser Met
    1490                1495               1500

Lys Leu Leu Asp Gln Val Met Pro Pro Ile Gly Asp Asp Glu Val
    1505                1510               1515

Thr Val Gly Lys Phe Tyr Ala Thr Phe Leu Ile Gln Glu Asp Phe
    1520                1525               1530

Arg Lys Phe Met Lys Arg Gln Glu Glu Tyr Tyr Gly Tyr Arg Pro
    1535                1540               1545

Lys Lys Asp Ile Val Gln Ile Gln Ala Gly Leu Arg Thr Ile Glu
    1550                1555               1560

Glu Glu Ala Ala Pro Glu Ile Cys Arg Thr Val Ser Gly Asp Leu
    1565                1570               1575

Ala Ala Glu Glu Glu Leu Glu Arg Ala Met Val Glu Ala Ala Met
    1580                1585               1590

Glu Glu Gly Ile Phe Arg Arg Thr Gly Gly Leu Phe Gly Gln Val
    1595                1600               1605

Asp Asn Phe Leu Glu Arg Thr Asn Ser Leu Pro Pro Val Met Ala
    1610                1615               1620
```

-continued

```
Asn Gln Arg Pro Leu Gln Phe Ala Glu Ile Glu Met Glu Glu Met
    1625                1630                1635

Glu Ser Pro Val Phe Leu Glu Asp Phe Pro Gln Asp Pro Arg Thr
    1640                1645                1650

Asn Pro Leu Ala Arg Ala Asn Thr Asn Ala Asn Ala Asn Val
    1655                1660                1665

Ala Tyr Gly Asn Ser Asn His Ser Asn Ser His Val Phe Ser Ser
    1670                1675                1680

Val His Tyr Glu Arg Glu Phe Pro Glu Glu Thr Glu Thr Pro Ala
    1685                1690                1695

Thr Arg Gly Arg Ala Leu Gly Gln Pro Cys Arg Val Leu Gly Pro
    1700                1705                1710

His Ser Lys Pro Cys Val Glu Met Leu Lys Gly Leu Leu Thr Gln
    1715                1720                1725

Arg Ala Met Pro Arg Gly Gln Ala Pro Pro Ala Pro Cys Gln Cys
    1730                1735                1740

Pro Arg Val Glu Ser Ser Met Pro Glu Asp Arg Lys Ser Ser Thr
    1745                1750                1755

Pro Gly Ser Leu His Glu Glu Thr Pro His Ser Arg Ser Thr Arg
    1760                1765                1770

Glu Asn Thr Ser Arg Cys Ser Ala Pro Ala Thr Ala Leu Leu Ile
    1775                1780                1785

Gln Lys Ala Leu Val Arg Gly Gly Leu Gly Thr Leu Ala Ala Asp
    1790                1795                1800

Ala Asn Phe Ile Met Ala Thr Gly Gln Ala Leu Gly Asp Ala Cys
    1805                1810                1815

Gln Met Glu Pro Glu Glu Val Glu Ile Met Ala Thr Glu Leu Leu
    1820                1825                1830

Lys Gly Arg Glu Ala Pro Gly Met Ala Ser Ser Leu Gly Cys
    1835                1840                1845

Leu Asn Leu Gly Ser Ser Leu Gly Ser Leu Asp Gln His Gln Gly
    1850                1855                1860

Ser Gln Glu Thr Leu Ile Pro Pro Arg Leu
    1865                1870

<210> SEQ ID NO 30
<211> LENGTH: 2221
<212> TYPE: PRT
<213> ORGANISM: homo sapiens

<400> SEQUENCE: 30

Met Val Asn Glu Asn Thr Arg Met Tyr Ile Pro Glu Glu Asn His Gln
1               5                   10                  15

Gly Ser Asn Tyr Gly Ser Pro Arg Pro Ala His Ala Asn Met Asn Ala
                20                  25                  30

Asn Ala Ala Ala Gly Leu Ala Pro Glu His Ile Pro Thr Pro Gly Ala
            35                  40                  45

Ala Leu Ser Trp Gln Ala Ala Ile Asp Ala Ala Arg Gln Ala Lys Leu
        50                  55                  60

Met Gly Ser Ala Gly Asn Ala Thr Ile Ser Thr Val Ser Ser Thr Gln
    65                  70                  75                  80

Arg Lys Arg Gln Gln Tyr Gly Lys Pro Lys Lys Gln Gly Ser Thr Thr
                85                  90                  95

Ala Thr Arg Pro Pro Arg Ala Leu Leu Cys Leu Thr Leu Lys Asn Pro
```

```
            100                 105                 110
Ile Arg Arg Ala Cys Ile Ser Ile Val Glu Trp Lys Pro Phe Glu Ile
        115                 120                 125
Ile Ile Leu Leu Thr Ile Phe Ala Asn Cys Val Ala Leu Ala Ile Tyr
130                 135                 140
Ile Pro Phe Pro Glu Asp Asp Ser Asn Ala Thr Asn Ser Asn Leu Glu
145                 150                 155                 160
Arg Val Glu Tyr Leu Phe Leu Ile Ile Phe Thr Val Glu Ala Phe Leu
                165                 170                 175
Lys Val Ile Ala Tyr Gly Leu Leu Phe His Pro Asn Ala Tyr Leu Arg
            180                 185                 190
Asn Gly Trp Asn Leu Leu Asp Phe Ile Ile Val Val Gly Leu Phe
            195                 200                 205
Ser Ala Ile Leu Glu Gln Ala Thr Lys Ala Asp Gly Ala Asn Ala Leu
        210                 215                 220
Gly Gly Lys Gly Ala Gly Phe Asp Val Lys Ala Leu Arg Ala Phe Arg
225                 230                 235                 240
Val Leu Arg Pro Leu Arg Leu Val Ser Gly Val Pro Ser Leu Gln Val
                245                 250                 255
Val Leu Asn Ser Ile Ile Lys Ala Met Val Pro Leu Leu His Ile Ala
            260                 265                 270
Leu Leu Val Leu Phe Val Ile Ile Tyr Ala Ile Ile Gly Leu Glu
            275                 280                 285
Leu Phe Met Gly Lys Met His Lys Thr Cys Tyr Asn Gln Glu Gly Ile
        290                 295                 300
Ala Asp Val Pro Ala Glu Asp Pro Ser Pro Cys Ala Leu Glu Thr
305                 310                 315                 320
Gly His Gly Arg Gln Cys Gln Asn Gly Thr Val Cys Lys Pro Gly Trp
                325                 330                 335
Asp Gly Pro Lys His Gly Ile Thr Asn Phe Asp Asn Phe Ala Phe Ala
            340                 345                 350
Met Leu Thr Val Phe Gln Cys Ile Thr Met Glu Gly Trp Thr Asp Val
        355                 360                 365
Leu Tyr Trp Val Asn Asp Ala Val Gly Arg Asp Trp Pro Trp Ile Tyr
370                 375                 380
Phe Val Thr Leu Ile Ile Ile Gly Ser Phe Phe Val Leu Asn Leu Val
385                 390                 395                 400
Leu Gly Val Leu Ser Gly Glu Phe Ser Lys Glu Arg Glu Lys Ala Lys
                405                 410                 415
Ala Arg Gly Asp Phe Gln Lys Leu Arg Glu Lys Gln Gln Leu Glu Glu
            420                 425                 430
Asp Leu Lys Gly Tyr Leu Asp Trp Ile Thr Gln Ala Glu Asp Ile Asp
        435                 440                 445
Pro Glu Asn Glu Asp Glu Gly Met Asp Glu Glu Lys Pro Arg Asn Met
        450                 455                 460
Ser Met Pro Thr Ser Glu Thr Glu Ser Val Asn Thr Glu Asn Val Ala
465                 470                 475                 480
Gly Gly Asp Ile Glu Gly Glu Asn Cys Gly Ala Arg Leu Ala His Arg
                485                 490                 495
Ile Ser Lys Ser Lys Phe Ser Arg Tyr Trp Arg Arg Trp Asn Arg Phe
            500                 505                 510
Cys Arg Arg Lys Cys Arg Ala Ala Val Lys Ser Asn Val Phe Tyr Trp
        515                 520                 525
```

-continued

```
Leu Val Ile Phe Leu Val Phe Leu Asn Thr Leu Thr Ile Ala Ser Glu
            530                 535                 540
His Tyr Asn Gln Pro Asn Trp Leu Thr Glu Val Gln Asp Thr Ala Asn
545                 550                 555                 560
Lys Ala Leu Leu Ala Leu Phe Thr Ala Glu Met Leu Leu Lys Met Tyr
                565                 570                 575
Ser Leu Gly Leu Gln Ala Tyr Phe Val Ser Leu Phe Asn Arg Phe Asp
            580                 585                 590
Cys Phe Val Val Cys Gly Gly Ile Leu Glu Thr Ile Leu Val Glu Thr
            595                 600                 605
Lys Ile Met Ser Pro Leu Gly Ile Ser Val Leu Arg Cys Val Arg Leu
            610                 615                 620
Leu Arg Ile Phe Lys Ile Thr Arg Tyr Trp Asn Ser Leu Ser Asn Leu
625                 630                 635                 640
Val Ala Ser Leu Leu Asn Ser Val Arg Ser Ile Ala Ser Leu Leu Leu
                645                 650                 655
Leu Leu Phe Leu Phe Ile Ile Ile Phe Ser Leu Leu Gly Met Gln Leu
            660                 665                 670
Phe Gly Gly Lys Phe Asn Phe Asp Glu Met Gln Thr Arg Arg Ser Thr
            675                 680                 685
Phe Asp Asn Phe Pro Gln Ser Leu Leu Thr Val Phe Gln Ile Leu Thr
690                 695                 700
Gly Glu Asp Trp Asn Ser Val Met Tyr Asp Gly Ile Met Ala Tyr Gly
705                 710                 715                 720
Gly Pro Ser Phe Pro Gly Met Leu Val Cys Ile Tyr Phe Ile Ile Leu
                725                 730                 735
Phe Ile Cys Gly Asn Tyr Ile Leu Leu Asn Val Phe Leu Ala Ile Ala
            740                 745                 750
Val Asp Asn Leu Ala Asp Ala Glu Ser Leu Thr Ser Ala Gln Lys Glu
            755                 760                 765
Glu Glu Glu Glu Lys Glu Arg Lys Lys Leu Ala Arg Thr Ala Ser Pro
770                 775                 780
Glu Lys Lys Gln Glu Leu Val Glu Lys Pro Ala Val Gly Glu Ser Lys
785                 790                 795                 800
Glu Glu Lys Ile Glu Leu Lys Ser Ile Thr Ala Asp Gly Glu Ser Pro
                805                 810                 815
Pro Ala Thr Lys Ile Asn Met Asp Asp Leu Gln Pro Asn Glu Asn Glu
            820                 825                 830
Asp Lys Ser Pro Tyr Pro Asn Pro Glu Thr Thr Gly Glu Glu Asp Glu
            835                 840                 845
Glu Glu Pro Glu Met Pro Val Gly Pro Arg Pro Arg Pro Leu Ser Glu
            850                 855                 860
Leu His Leu Lys Glu Lys Ala Val Pro Met Pro Glu Ala Ser Ala Phe
865                 870                 875                 880
Phe Ile Phe Ser Ser Asn Asn Arg Phe Arg Leu Gln Cys His Arg Ile
                885                 890                 895
Val Asn Asp Thr Ile Phe Thr Asn Leu Ile Leu Phe Phe Ile Leu Leu
            900                 905                 910
Ser Ser Ile Ser Leu Ala Ala Glu Asp Pro Val Gln His Thr Ser Phe
            915                 920                 925
Arg Asn His Ile Leu Phe Tyr Phe Asp Ile Val Phe Thr Thr Ile Phe
            930                 935                 940
```

```
Thr Ile Glu Ile Ala Leu Lys Ile Leu Gly Asn Ala Asp Tyr Val Phe
945                 950                 955                 960

Thr Ser Ile Phe Thr Leu Glu Ile Ile Leu Lys Met Thr Ala Tyr Gly
            965                 970                 975

Ala Phe Leu His Lys Gly Ser Phe Cys Arg Asn Tyr Phe Asn Ile Leu
            980                 985                 990

Asp Leu Leu Val Val Ser Val Ser Leu Ile Ser Phe Gly Ile Gln Ser
        995                 1000                1005

Ser Ala Ile Asn Val Val Lys Ile Leu Arg Val Leu Arg Val Leu
    1010                1015                1020

Arg Pro Leu Arg Ala Ile Asn Arg Ala Lys Gly Leu Lys His Val
    1025                1030                1035

Val Gln Cys Val Phe Val Ala Ile Arg Thr Ile Gly Asn Ile Val
    1040                1045                1050

Ile Val Thr Thr Leu Leu Gln Phe Met Phe Ala Cys Ile Gly Val
    1055                1060                1065

Gln Leu Phe Lys Gly Lys Leu Tyr Thr Cys Ser Asp Ser Ser Lys
    1070                1075                1080

Gln Thr Glu Ala Glu Cys Lys Gly Asn Tyr Ile Thr Tyr Lys Asp
    1085                1090                1095

Gly Glu Val Asp His Pro Ile Ile Gln Pro Arg Ser Trp Glu Asn
    1100                1105                1110

Ser Lys Phe Asp Phe Asp Asn Val Leu Ala Ala Met Met Ala Leu
    1115                1120                1125

Phe Thr Val Ser Thr Phe Glu Gly Trp Pro Glu Leu Leu Tyr Arg
    1130                1135                1140

Ser Ile Asp Ser His Thr Glu Asp Lys Gly Pro Ile Tyr Asn Tyr
    1145                1150                1155

Arg Val Glu Ile Ser Ile Phe Phe Ile Ile Tyr Ile Ile Ile Ile
    1160                1165                1170

Ala Phe Phe Met Met Asn Ile Phe Val Gly Phe Val Ile Val Thr
    1175                1180                1185

Phe Gln Glu Gln Gly Glu Gln Glu Tyr Lys Asn Cys Glu Leu Asp
    1190                1195                1200

Lys Asn Gln Arg Gln Cys Val Glu Tyr Ala Leu Lys Ala Arg Pro
    1205                1210                1215

Leu Arg Arg Tyr Ile Pro Lys Asn Gln His Gln Tyr Lys Val Trp
    1220                1225                1230

Tyr Val Val Asn Ser Thr Tyr Phe Glu Tyr Leu Met Phe Val Leu
    1235                1240                1245

Ile Leu Leu Asn Thr Ile Cys Leu Ala Met Gln His Tyr Gly Gln
    1250                1255                1260

Ser Cys Leu Phe Lys Ile Ala Met Asn Ile Leu Asn Met Leu Phe
    1265                1270                1275

Thr Gly Leu Phe Thr Val Glu Met Ile Leu Lys Leu Ile Ala Phe
    1280                1285                1290

Lys Pro Lys Gly Tyr Phe Ser Asp Pro Trp Asn Val Phe Asp Phe
    1295                1300                1305

Leu Ile Val Ile Gly Ser Ile Ile Asp Val Ile Leu Ser Glu Thr
    1310                1315                1320

Asn His Tyr Phe Cys Asp Ala Trp Asn Thr Phe Asp Ala Leu Ile
    1325                1330                1335

Val Val Gly Ser Ile Val Asp Ile Ala Ile Thr Glu Val Asn Pro
```

-continued

```
                1340                1345                1350
Ala Glu His Thr Gln Cys Ser Pro Ser Met Asn Ala Glu Glu Asn
    1355                1360                1365

Ser Arg Ile Ser Ile Thr Phe Phe Arg Leu Phe Arg Val Met Arg
    1370                1375                1380

Leu Val Lys Leu Leu Ser Arg Gly Glu Gly Ile Arg Thr Leu Leu
    1385                1390                1395

Trp Thr Phe Ile Lys Ser Phe Gln Ala Leu Pro Tyr Val Ala Leu
    1400                1405                1410

Leu Ile Val Met Leu Phe Phe Ile Tyr Ala Val Ile Gly Met Gln
    1415                1420                1425

Val Phe Gly Lys Ile Ala Leu Asn Asp Thr Thr Glu Ile Asn Arg
    1430                1435                1440

Asn Asn Asn Phe Gln Thr Phe Pro Gln Ala Val Leu Leu Leu Phe
    1445                1450                1455

Arg Cys Ala Thr Gly Glu Ala Trp Gln Asp Ile Met Leu Ala Cys
    1460                1465                1470

Met Pro Gly Lys Lys Cys Ala Pro Glu Ser Glu Pro Ser Asn Ser
    1475                1480                1485

Thr Glu Gly Glu Thr Pro Cys Gly Ser Ser Phe Ala Val Phe Tyr
    1490                1495                1500

Phe Ile Ser Phe Tyr Met Leu Cys Ala Phe Leu Ile Ile Asn Leu
    1505                1510                1515

Phe Val Ala Val Ile Met Asp Asn Phe Asp Tyr Leu Thr Arg Asp
    1520                1525                1530

Trp Ser Ile Leu Gly Pro His His Leu Asp Glu Phe Lys Arg Ile
    1535                1540                1545

Trp Ala Glu Tyr Asp Pro Glu Ala Lys Gly Arg Ile Lys His Leu
    1550                1555                1560

Asp Val Val Thr Leu Leu Arg Arg Ile Gln Pro Pro Leu Gly Phe
    1565                1570                1575

Gly Lys Leu Cys Pro His Arg Val Ala Cys Lys Arg Leu Val Ser
    1580                1585                1590

Met Asn Met Pro Leu Asn Ser Asp Gly Thr Val Met Phe Asn Ala
    1595                1600                1605

Thr Leu Phe Ala Leu Val Arg Thr Ala Leu Arg Ile Lys Thr Glu
    1610                1615                1620

Gly Asn Leu Glu Gln Ala Asn Glu Glu Leu Arg Ala Ile Ile Lys
    1625                1630                1635

Lys Ile Trp Lys Arg Thr Ser Met Lys Leu Leu Asp Gln Val Val
    1640                1645                1650

Pro Pro Ala Gly Asp Asp Glu Val Thr Val Gly Lys Phe Tyr Ala
    1655                1660                1665

Thr Phe Leu Ile Gln Glu Tyr Phe Arg Lys Phe Lys Lys Arg Lys
    1670                1675                1680

Glu Gln Gly Leu Val Gly Lys Pro Ser Gln Arg Asn Ala Leu Ser
    1685                1690                1695

Leu Gln Ala Gly Leu Arg Thr Leu His Asp Ile Gly Pro Glu Ile
    1700                1705                1710

Arg Arg Ala Ile Ser Gly Asp Leu Thr Ala Glu Glu Glu Leu Asp
    1715                1720                1725

Lys Ala Met Lys Glu Ala Val Ser Ala Ala Ser Glu Asp Asp Ile
    1730                1735                1740
```

-continued

Phe Arg Arg Ala Gly Gly Leu Phe Gly Asn His Val Ser Tyr Tyr
1745                1750                1755

Gln Ser Asp Gly Arg Ser Ala Phe Pro Gln Thr Phe Thr Thr Gln
1760                1765                1770

Arg Pro Leu His Ile Asn Lys Ala Gly Ser Ser Gln Gly Asp Thr
1775                1780                1785

Glu Ser Pro Ser His Glu Lys Leu Val Asp Ser Thr Phe Thr Pro
1790                1795                1800

Ser Ser Tyr Ser Ser Thr Gly Ser Asn Ala Asn Ile Asn Asn Ala
1805                1810                1815

Asn Asn Thr Ala Leu Gly Arg Leu Pro Arg Pro Ala Gly Tyr Pro
1820                1825                1830

Ser Thr Val Ser Thr Val Glu Gly His Gly Pro Pro Leu Ser Pro
1835                1840                1845

Ala Ile Arg Val Gln Glu Val Ala Trp Lys Leu Ser Ser Asn Arg
1850                1855                1860

Glu Arg His Val Pro Val Cys Glu Asp Leu Glu Leu Arg Arg Asp
1865                1870                1875

Ser Gly Ser Ala Gly Thr Gln Ala His Cys Leu Leu Leu Arg Arg
1880                1885                1890

Ala Asn Pro Ser Arg Cys His Ser Arg Glu Ser Gln Ala Ala Met
1895                1900                1905

Ala Gly Gln Glu Glu Thr Ser Gln Asp Glu Thr Tyr Glu Val Lys
1910                1915                1920

Met Asn His Asp Thr Glu Ala Cys Ser Glu Pro Ser Leu Leu Ser
1925                1930                1935

Thr Glu Met Leu Ser Tyr Gln Asp Asp Glu Asn Arg Gln Leu Thr
1940                1945                1950

Leu Pro Glu Glu Asp Lys Arg Asp Ile Arg Gln Ser Pro Lys Arg
1955                1960                1965

Gly Phe Leu Arg Ser Ala Ser Leu Gly Arg Arg Ala Ser Phe His
1970                1975                1980

Leu Glu Cys Leu Lys Arg Gln Lys Asp Arg Gly Gly Asp Ile Ser
1985                1990                1995

Gln Lys Thr Val Leu Pro Leu His Leu Val His His Gln Ala Leu
2000                2005                2010

Ala Val Ala Gly Leu Ser Pro Leu Leu Gln Arg Ser His Ser Pro
2015                2020                2025

Ala Ser Phe Pro Arg Pro Phe Ala Thr Pro Pro Ala Thr Pro Gly
2030                2035                2040

Ser Arg Gly Trp Pro Pro Gln Pro Val Pro Thr Leu Arg Leu Glu
2045                2050                2055

Gly Val Glu Ser Ser Glu Lys Leu Asn Ser Ser Phe Pro Ser Ile
2060                2065                2070

His Cys Gly Ser Trp Ala Glu Thr Thr Pro Gly Gly Gly Gly Ser
2075                2080                2085

Ser Ala Ala Arg Arg Val Arg Pro Val Ser Leu Met Val Pro Ser
2090                2095                2100

Gln Ala Gly Ala Pro Gly Arg Gln Phe His Gly Ser Ala Ser Ser
2105                2110                2115

Leu Val Glu Ala Val Leu Ile Ser Glu Gly Leu Gly Gln Phe Ala
2120                2125                2130

-continued

Gln Asp Pro Lys Phe Ile Glu Val Thr Thr Gln Glu Leu Ala Asp
        2135                2140                2145

Ala Cys Asp Met Thr Ile Glu Glu Met Glu Ser Ala Ala Asp Asn
        2150                2155                2160

Ile Leu Ser Gly Gly Ala Pro Gln Ser Pro Asn Gly Ala Leu Leu
        2165                2170                2175

Pro Phe Val Asn Cys Arg Asp Ala Gly Gln Asp Arg Ala Gly Gly
        2180                2185                2190

Glu Glu Asp Ala Gly Cys Val Arg Ala Arg Gly Ala Pro Ser Glu
        2195                2200                2205

Glu Glu Leu Gln Asp Ser Arg Val Tyr Val Ser Ser Leu
        2210                2215                2220

<210> SEQ ID NO 31
<211> LENGTH: 2161
<212> TYPE: PRT
<213> ORGANISM: homo sapiens

<400> SEQUENCE: 31

Met Met Met Met Met Met Lys Lys Met Gln His Gln Arg Gln Gln
1               5                   10                  15

Gln Ala Asp His Ala Asn Glu Ala Asn Tyr Ala Arg Gly Thr Arg Leu
                20                  25                  30

Pro Leu Ser Gly Glu Gly Pro Thr Ser Gln Pro Asn Ser Ser Lys Gln
            35                  40                  45

Thr Val Leu Ser Trp Gln Ala Ala Ile Asp Ala Ala Arg Gln Ala Lys
        50                  55                  60

Ala Ala Gln Thr Met Ser Thr Ser Ala Pro Pro Pro Val Gly Ser Leu
65                  70                  75                  80

Ser Gln Arg Lys Arg Gln Gln Tyr Ala Lys Ser Lys Lys Gln Gly Asn
                85                  90                  95

Ser Ser Asn Ser Arg Pro Ala Arg Ala Leu Phe Cys Leu Ser Leu Asn
            100                 105                 110

Asn Pro Ile Arg Arg Ala Cys Ile Ser Ile Val Glu Trp Lys Pro Phe
        115                 120                 125

Asp Ile Phe Ile Leu Leu Ala Ile Phe Ala Asn Cys Val Ala Leu Ala
    130                 135                 140

Ile Tyr Ile Pro Phe Pro Glu Asp Asp Ser Asn Ser Thr Asn His Asn
145                 150                 155                 160

Leu Glu Lys Val Glu Tyr Ala Phe Leu Ile Ile Phe Thr Val Glu Thr
                165                 170                 175

Phe Leu Lys Ile Ile Ala Tyr Gly Leu Leu Leu His Pro Asn Ala Tyr
            180                 185                 190

Val Arg Asn Gly Trp Asn Leu Leu Asp Phe Val Ile Val Ile Val Gly
        195                 200                 205

Leu Phe Ser Val Ile Leu Glu Gln Leu Thr Lys Glu Thr Glu Gly Gly
    210                 215                 220

Asn His Ser Ser Gly Lys Ser Gly Gly Phe Asp Val Lys Ala Leu Arg
225                 230                 235                 240

Ala Phe Arg Val Leu Arg Pro Leu Arg Leu Val Ser Gly Val Pro Ser
                245                 250                 255

Leu Gln Val Val Leu Asn Ser Ile Ile Lys Ala Met Val Pro Leu Leu
            260                 265                 270

His Ile Ala Leu Leu Val Leu Phe Val Ile Ile Ile Tyr Ala Ile Ile
        275                 280                 285

-continued

```
Gly Leu Glu Leu Phe Ile Gly Lys Met His Lys Thr Cys Phe Phe Ala
        290                 295                 300
Asp Ser Asp Ile Val Ala Glu Asp Pro Ala Pro Cys Ala Phe Ser
305                 310                 315                 320
Gly Asn Gly Arg Gln Cys Thr Ala Asn Gly Thr Glu Cys Arg Ser Gly
                325                 330                 335
Trp Val Gly Pro Asn Gly Gly Ile Thr Asn Phe Asp Asn Phe Ala Phe
                340                 345                 350
Ala Met Leu Thr Val Phe Gln Cys Ile Thr Met Glu Gly Trp Thr Asp
            355                 360                 365
Val Leu Tyr Trp Met Asn Asp Ala Met Gly Phe Glu Leu Pro Trp Val
    370                 375                 380
Tyr Phe Val Ser Leu Val Ile Phe Gly Ser Phe Val Leu Asn Leu
385                 390                 395                 400
Val Leu Gly Val Leu Ser Gly Glu Phe Ser Lys Glu Arg Glu Lys Ala
                405                 410                 415
Lys Ala Arg Gly Asp Phe Gln Lys Leu Arg Glu Lys Gln Gln Leu Glu
                420                 425                 430
Glu Asp Leu Lys Gly Tyr Leu Asp Trp Ile Thr Gln Ala Glu Asp Ile
            435                 440                 445
Asp Pro Glu Asn Glu Glu Glu Gly Gly Glu Glu Gly Lys Arg Asn Thr
    450                 455                 460
Ser Met Pro Thr Ser Glu Thr Glu Ser Val Asn Thr Glu Asn Val Ser
465                 470                 475                 480
Gly Glu Gly Glu Asn Arg Gly Cys Cys Gly Ser Leu Cys Gln Ala Ile
                485                 490                 495
Ser Lys Ser Lys Leu Ser Arg Arg Trp Arg Arg Trp Asn Arg Phe Asn
                500                 505                 510
Arg Arg Arg Cys Arg Ala Ala Val Lys Ser Val Thr Phe Tyr Trp Leu
                515                 520                 525
Val Ile Val Leu Val Phe Leu Asn Thr Leu Thr Ile Ser Ser Glu His
    530                 535                 540
Tyr Asn Gln Pro Asp Trp Leu Thr Gln Ile Gln Asp Ile Ala Asn Lys
545                 550                 555                 560
Val Leu Leu Ala Leu Phe Thr Cys Glu Met Leu Val Lys Met Tyr Ser
                565                 570                 575
Leu Gly Leu Gln Ala Tyr Phe Val Ser Leu Phe Asn Arg Phe Asp Cys
            580                 585                 590
Phe Val Val Cys Gly Gly Ile Thr Glu Thr Ile Leu Val Glu Leu Glu
            595                 600                 605
Ile Met Ser Pro Leu Gly Ile Ser Val Phe Arg Cys Val Arg Leu Leu
    610                 615                 620
Arg Ile Phe Lys Val Thr Arg His Trp Thr Ser Leu Cys Asn Leu Val
625                 630                 635                 640
Ala Ser Leu Leu Asn Ser Met Lys Ser Ala Ser Leu Leu Leu Leu
                645                 650                 655
Leu Phe Leu Phe Ile Ile Ile Phe Ser Leu Leu Gly Met Gln Leu Phe
            660                 665                 670
Gly Gly Lys Phe Asn Phe Asp Glu Thr Gln Thr Lys Arg Ser Thr Phe
            675                 680                 685
Asp Asn Phe Pro Gln Ala Leu Leu Thr Val Phe Gln Ile Leu Thr Gly
    690                 695                 700
```

-continued

Glu Asp Trp Asn Ala Val Met Tyr Asp Gly Ile Met Ala Tyr Gly Gly
705                 710                 715                 720

Pro Ser Ser Ser Gly Met Ile Val Cys Ile Tyr Phe Ile Ile Leu Phe
            725                 730                 735

Ile Cys Gly Asn Tyr Ile Leu Leu Asn Val Phe Leu Ala Ile Ala Val
            740                 745                 750

Asp Asn Leu Ala Asp Ala Glu Ser Leu Asn Thr Ala Gln Lys Glu Glu
            755                 760                 765

Ala Glu Glu Lys Glu Arg Lys Lys Ile Ala Arg Lys Glu Ser Leu Glu
770                 775                 780

Asn Lys Lys Asn Asn Lys Pro Glu Val Asn Gln Ile Ala Asn Ser Asp
785                 790                 795                 800

Asn Lys Val Thr Ile Asp Asp Tyr Arg Glu Glu Asp Glu Asp Lys Asp
                805                 810                 815

Pro Tyr Pro Pro Cys Asp Val Pro Val Gly Glu Glu Glu Glu Glu Glu
                820                 825                 830

Glu Glu Asp Glu Pro Glu Val Pro Ala Gly Pro Arg Pro Arg Arg Ile
            835                 840                 845

Ser Glu Leu Asn Met Lys Glu Lys Ile Ala Pro Ile Pro Glu Gly Ser
            850                 855                 860

Ala Phe Phe Ile Leu Ser Lys Thr Asn Pro Ile Arg Val Gly Cys His
865                 870                 875                 880

Lys Leu Ile Asn His His Ile Phe Thr Asn Leu Ile Leu Val Phe Ile
                885                 890                 895

Met Leu Ser Ser Ala Ala Leu Ala Ala Glu Asp Pro Ile Arg Ser His
            900                 905                 910

Ser Phe Arg Asn Thr Ile Leu Gly Tyr Phe Asp Tyr Ala Phe Thr Ala
            915                 920                 925

Ile Phe Thr Val Glu Ile Leu Leu Lys Met Thr Thr Phe Gly Ala Phe
            930                 935                 940

Leu His Lys Gly Ala Phe Cys Arg Asn Tyr Phe Asn Leu Leu Asp Met
945                 950                 955                 960

Leu Val Val Gly Val Ser Leu Val Ser Phe Gly Ile Gln Ser Ser Ala
                965                 970                 975

Ile Ser Val Val Lys Ile Leu Arg Val Leu Arg Val Leu Arg Pro Leu
            980                 985                 990

Arg Ala Ile Asn Arg Ala Lys Gly Leu Lys His Val Val Gln Cys Val
            995                 1000                1005

Phe Val Ala Ile Arg Thr Ile Gly Asn Ile Met Ile Val Thr Thr
    1010                1015                1020

Leu Leu Gln Phe Met Phe Ala Cys Ile Gly Val Gln Leu Phe Lys
    1025                1030                1035

Gly Lys Phe Tyr Arg Cys Thr Asp Glu Ala Lys Ser Asn Pro Glu
    1040                1045                1050

Glu Cys Arg Gly Leu Phe Ile Leu Tyr Lys Asp Gly Asp Val Asp
    1055                1060                1065

Ser Pro Val Val Arg Glu Arg Ile Trp Gln Asn Ser Asp Phe Asn
    1070                1075                1080

Phe Asp Asn Val Leu Ser Ala Met Met Ala Leu Phe Thr Val Ser
    1085                1090                1095

Thr Phe Glu Gly Trp Pro Ala Leu Leu Tyr Lys Ala Ile Asp Ser
    1100                1105                1110

Asn Gly Glu Asn Ile Gly Pro Ile Tyr Asn His Arg Val Glu Ile

-continued

```
            1115                    1120                    1125
Ser Ile Phe Phe Ile Ile Tyr Ile Ile Ile Val Ala Phe Phe Met
            1130                    1135                    1140
Met Asn Ile Phe Val Gly Phe Val Ile Val Thr Phe Gln Glu Gln
            1145                    1150                    1155
Gly Glu Lys Glu Tyr Lys Asn Cys Glu Leu Asp Lys Asn Gln Arg
            1160                    1165                    1170
Gln Cys Val Glu Tyr Ala Leu Lys Ala Arg Pro Leu Arg Arg Tyr
            1175                    1180                    1185
Ile Pro Lys Asn Pro Tyr Gln Tyr Lys Phe Trp Tyr Val Val Asn
            1190                    1195                    1200
Ser Ser Pro Phe Glu Tyr Met Met Phe Val Leu Ile Met Leu Asn
            1205                    1210                    1215
Thr Leu Cys Leu Ala Met Gln His Tyr Glu Gln Ser Lys Met Phe
            1220                    1225                    1230
Asn Asp Ala Met Asp Ile Leu Asn Met Val Phe Thr Gly Val Phe
            1235                    1240                    1245
Thr Val Glu Met Val Leu Lys Val Ile Ala Phe Lys Pro Lys Gly
            1250                    1255                    1260
Tyr Phe Ser Asp Ala Trp Asn Thr Phe Asp Ser Leu Ile Val Ile
            1265                    1270                    1275
Gly Ser Ile Ile Asp Val Ala Leu Ser Glu Ala Asp Pro Thr Glu
            1280                    1285                    1290
Ser Glu Asn Val Pro Val Pro Thr Ala Thr Pro Gly Asn Ser Glu
            1295                    1300                    1305
Glu Ser Asn Arg Ile Ser Ile Thr Phe Phe Arg Leu Phe Arg Val
            1310                    1315                    1320
Met Arg Leu Val Lys Leu Leu Ser Arg Gly Glu Gly Ile Arg Thr
            1325                    1330                    1335
Leu Leu Trp Thr Phe Ile Lys Phe Phe Gln Ala Leu Pro Tyr Val
            1340                    1345                    1350
Ala Leu Leu Ile Ala Met Leu Phe Phe Ile Tyr Ala Val Ile Gly
            1355                    1360                    1365
Met Gln Met Phe Gly Lys Val Ala Met Arg Asp Asn Asn Gln Ile
            1370                    1375                    1380
Asn Arg Asn Asn Asn Phe Gln Thr Phe Pro Gln Ala Val Leu Leu
            1385                    1390                    1395
Leu Phe Arg Cys Ala Thr Gly Glu Ala Trp Gln Glu Ile Met Leu
            1400                    1405                    1410
Ala Cys Leu Pro Gly Lys Leu Cys Asp Pro Glu Ser Asp Tyr Asn
            1415                    1420                    1425
Pro Gly Glu Glu His Thr Cys Gly Ser Asn Phe Ala Ile Val Tyr
            1430                    1435                    1440
Phe Ile Ser Phe Tyr Met Leu Cys Ala Phe Leu Ile Ile Asn Leu
            1445                    1450                    1455
Phe Val Ala Val Ile Met Asp Asn Phe Asp Tyr Leu Thr Arg Asp
            1460                    1465                    1470
Trp Ser Ile Leu Gly Pro His His Leu Asp Glu Phe Lys Arg Ile
            1475                    1480                    1485
Trp Ser Glu Tyr Asp Pro Glu Ala Lys Gly Arg Ile Lys His Leu
            1490                    1495                    1500
Asp Val Val Thr Leu Leu Arg Arg Ile Gln Pro Pro Leu Gly Phe
            1505                    1510                    1515
```

```
Gly Lys Leu Cys Pro His Arg Val Ala Cys Lys Arg Leu Val Ala
    1520                1525                1530

Met Asn Met Pro Leu Asn Ser Asp Gly Thr Val Met Phe Asn Ala
    1535                1540                1545

Thr Leu Phe Ala Leu Val Arg Thr Ala Leu Lys Ile Lys Thr Glu
    1550                1555                1560

Gly Asn Leu Glu Gln Ala Asn Glu Glu Leu Arg Ala Val Ile Lys
    1565                1570                1575

Lys Ile Trp Lys Lys Thr Ser Met Lys Leu Leu Asp Gln Val Val
    1580                1585                1590

Pro Pro Ala Gly Asp Asp Glu Val Thr Val Gly Lys Phe Tyr Ala
    1595                1600                1605

Thr Phe Leu Ile Gln Asp Tyr Phe Arg Lys Phe Lys Lys Arg Lys
    1610                1615                1620

Glu Gln Gly Leu Val Gly Lys Tyr Pro Ala Lys Asn Thr Thr Ile
    1625                1630                1635

Ala Leu Gln Ala Gly Leu Arg Thr Leu His Asp Ile Gly Pro Glu
    1640                1645                1650

Ile Arg Arg Ala Ile Ser Cys Asp Leu Gln Asp Asp Glu Pro Glu
    1655                1660                1665

Glu Thr Lys Arg Glu Glu Asp Asp Val Phe Lys Arg Asn Gly
    1670                1675                1680

Ala Leu Leu Gly Asn His Val Asn His Val Asn Ser Asp Arg Arg
    1685                1690                1695

Asp Ser Leu Gln Gln Thr Asn Thr Thr His Arg Pro Leu His Val
    1700                1705                1710

Gln Arg Pro Ser Ile Pro Pro Ala Ser Asp Thr Glu Lys Pro Leu
    1715                1720                1725

Phe Pro Pro Ala Gly Asn Ser Val Cys His Asn His His Asn His
    1730                1735                1740

Asn Ser Ile Gly Lys Gln Val Pro Thr Ser Thr Asn Ala Asn Leu
    1745                1750                1755

Asn Asn Ala Asn Met Ser Lys Ala Ala His Gly Lys Arg Pro Ser
    1760                1765                1770

Ile Gly Asn Leu Glu His Val Ser Glu Asn Gly His His Ser Ser
    1775                1780                1785

His Lys His Asp Arg Glu Pro Gln Arg Arg Ser Ser Val Lys Arg
    1790                1795                1800

Thr Arg Tyr Tyr Glu Thr Tyr Ile Arg Ser Asp Ser Gly Asp Glu
    1805                1810                1815

Gln Leu Pro Thr Ile Cys Arg Glu Asp Pro Glu Ile His Gly Tyr
    1820                1825                1830

Phe Arg Asp Pro His Cys Leu Gly Glu Gln Glu Tyr Phe Ser Ser
    1835                1840                1845

Glu Glu Cys Tyr Glu Asp Asp Ser Ser Pro Thr Trp Ser Arg Gln
    1850                1855                1860

Asn Tyr Gly Tyr Tyr Ser Arg Tyr Pro Gly Arg Asn Ile Asp Ser
    1865                1870                1875

Glu Arg Pro Arg Gly Tyr His His Pro Gln Gly Phe Leu Glu Asp
    1880                1885                1890

Asp Asp Ser Pro Val Cys Tyr Asp Ser Arg Arg Ser Pro Arg Arg
    1895                1900                1905
```

```
Arg Leu Leu Pro Pro Thr Pro Ala Ser His Arg Arg Ser Ser Phe
    1910            1915            1920

Asn Phe Glu Cys Leu Arg Arg Gln Ser Ser Gln Glu Glu Val Pro
    1925            1930            1935

Ser Ser Pro Ile Phe Pro His Arg Thr Ala Leu Pro Leu His Leu
    1940            1945            1950

Met Gln Gln Gln Ile Met Ala Val Ala Gly Leu Asp Ser Ser Lys
    1955            1960            1965

Ala Gln Lys Tyr Ser Pro Ser His Ser Thr Arg Ser Trp Ala Thr
    1970            1975            1980

Pro Pro Ala Thr Pro Pro Tyr Arg Asp Trp Thr Pro Cys Tyr Thr
    1985            1990            1995

Pro Leu Ile Gln Val Glu Gln Ser Glu Ala Leu Asp Gln Val Asn
    2000            2005            2010

Gly Ser Leu Pro Ser Leu His Arg Ser Ser Trp Tyr Thr Asp Glu
    2015            2020            2025

Pro Asp Ile Ser Tyr Arg Thr Phe Thr Pro Ala Ser Leu Thr Val
    2030            2035            2040

Pro Ser Ser Phe Arg Asn Lys Asn Ser Asp Lys Gln Arg Ser Ala
    2045            2050            2055

Asp Ser Leu Val Glu Ala Val Leu Ile Ser Glu Gly Leu Gly Arg
    2060            2065            2070

Tyr Ala Arg Asp Pro Lys Phe Val Ser Ala Thr Lys His Glu Ile
    2075            2080            2085

Ala Asp Ala Cys Asp Leu Thr Ile Asp Glu Met Glu Ser Ala Ala
    2090            2095            2100

Ser Thr Leu Leu Asn Gly Asn Val Arg Pro Arg Ala Asn Gly Asp
    2105            2110            2115

Val Gly Pro Leu Ser His Arg Gln Asp Tyr Glu Leu Gln Asp Phe
    2120            2125            2130

Gly Pro Gly Tyr Ser Asp Glu Glu Pro Asp Pro Gly Arg Asp Glu
    2135            2140            2145

Glu Asp Leu Ala Asp Glu Met Ile Cys Ile Thr Thr Leu
    2150            2155            2160

<210> SEQ ID NO 32
<211> LENGTH: 1966
<212> TYPE: PRT
<213> ORGANISM: homo sapiens

<400> SEQUENCE: 32

Met Ser Glu Ser Glu Gly Gly Lys Asp Thr Thr Pro Glu Pro Ser Pro
1               5                   10                  15

Ala Asn Gly Ala Gly Pro Gly Pro Glu Trp Gly Leu Cys Pro Gly Pro
                20                  25                  30

Pro Ala Val Glu Gly Glu Ser Ser Gly Ala Ser Gly Leu Gly Thr Pro
            35                  40                  45

Lys Arg Arg Asn Gln His Ser Lys His Lys Thr Val Ala Val Ala Ser
        50                  55                  60

Ala Gln Arg Ser Pro Arg Ala Leu Phe Cys Leu Thr Leu Ala Asn Pro
65                  70                  75                  80

Leu Arg Arg Ser Cys Ile Ser Ile Val Glu Trp Lys Pro Phe Asp Ile
                85                  90                  95

Leu Ile Leu Leu Thr Ile Phe Ala Asn Cys Val Ala Leu Gly Val Tyr
            100                 105                 110
```

```
Ile Pro Phe Pro Glu Asp Asp Ser Asn Thr Ala Asn His Asn Leu Glu
            115                 120                 125

Gln Val Glu Tyr Val Phe Leu Val Ile Phe Thr Val Glu Thr Val Leu
        130                 135                 140

Lys Ile Val Ala Tyr Gly Leu Val Leu His Pro Ser Ala Tyr Ile Arg
145                 150                 155                 160

Asn Gly Trp Asn Leu Leu Asp Phe Ile Ile Val Val Gly Leu Phe
                165                 170                 175

Ser Val Leu Leu Glu Gln Gly Pro Gly Arg Pro Gly Asp Ala Pro His
            180                 185                 190

Thr Gly Gly Lys Pro Gly Gly Phe Asp Val Lys Ala Leu Arg Ala Phe
        195                 200                 205

Arg Val Leu Arg Pro Leu Arg Leu Val Ser Gly Val Pro Ser Leu His
        210                 215                 220

Ile Val Leu Asn Ser Ile Met Lys Ala Leu Val Pro Leu Leu His Ile
225                 230                 235                 240

Ala Leu Leu Val Leu Phe Val Ile Ile Tyr Ala Ile Ile Gly Leu
                245                 250                 255

Glu Leu Phe Leu Gly Arg Met His Lys Thr Cys Tyr Phe Leu Gly Ser
            260                 265                 270

Asp Met Glu Ala Glu Gly Asp Pro Ser Pro Cys Ala Ser Ser Gly Ser
            275                 280                 285

Gly Arg Ala Cys Thr Leu Asn Gln Thr Glu Cys Arg Gly Arg Trp Pro
        290                 295                 300

Gly Pro Asn Gly Gly Ile Thr Asn Phe Asp Asn Phe Phe Phe Ala Met
305                 310                 315                 320

Leu Thr Val Phe Gln Cys Val Thr Met Glu Gly Trp Thr Asp Val Leu
                325                 330                 335

Tyr Trp Met Gln Asp Ala Met Gly Tyr Glu Leu Pro Trp Val Tyr Phe
            340                 345                 350

Val Ser Leu Val Ile Phe Gly Ser Phe Phe Val Leu Asn Leu Val Leu
        355                 360                 365

Gly Val Leu Ser Gly Glu Phe Ser Lys Glu Arg Glu Lys Ala Lys Ala
        370                 375                 380

Arg Gly Asp Phe Gln Lys Gln Arg Glu Lys Gln Met Glu Glu Asp
385                 390                 395                 400

Leu Arg Gly Tyr Leu Asp Trp Ile Thr Gln Ala Glu Glu Leu Asp Met
                405                 410                 415

Glu Asp Pro Ser Ala Asp Asp Asn Leu Gly Pro Gln Leu Ala Glu Leu
            420                 425                 430

Thr Asn Arg Arg Arg Gly Arg Leu Arg Trp Phe Ser His Ser Thr Arg
        435                 440                 445

Ser Thr His Ser Thr Ser Ser His Ala Ser Leu Pro Ala Ser Asp Thr
        450                 455                 460

Gly Ser Met Thr Glu Thr Gln Gly Asp Glu Asp Glu Glu Gly Ala
465                 470                 475                 480

Leu Ala Ser Cys Thr Arg Cys Leu Asn Lys Ile Met Lys Thr Arg Val
                485                 490                 495

Cys Arg Arg Leu Arg Arg Ala Asn Arg Val Leu Arg Ala Arg Cys Arg
            500                 505                 510

Arg Ala Val Lys Ser Asn Ala Cys Tyr Trp Ala Val Leu Leu Leu Val
        515                 520                 525
```

```
Phe Leu Asn Thr Leu Thr Ile Ala Ser Glu His His Gly Gln Pro Val
    530                 535                 540

Trp Leu Thr Gln Ile Gln Glu Tyr Ala Asn Lys Val Leu Leu Cys Leu
545                 550                 555                 560

Phe Thr Val Glu Met Leu Leu Lys Leu Tyr Gly Leu Gly Pro Ser Ala
                565                 570                 575

Tyr Val Ser Ser Phe Phe Asn Arg Phe Asp Cys Phe Val Val Cys Gly
            580                 585                 590

Gly Ile Leu Glu Thr Thr Leu Val Glu Val Gly Ala Met Gln Pro Leu
        595                 600                 605

Gly Ile Ser Val Leu Arg Cys Val Arg Leu Leu Arg Ile Phe Lys Val
        610                 615                 620

Thr Arg His Trp Ala Ser Leu Ser Asn Leu Val Ala Ser Leu Leu Asn
625                 630                 635                 640

Ser Met Lys Ser Ile Ala Ser Leu Leu Leu Leu Phe Leu Phe Ile
                645                 650                 655

Ile Ile Phe Ser Leu Leu Gly Met Gln Leu Phe Gly Gly Lys Phe Asn
            660                 665                 670

Phe Asp Gln Thr His Thr Lys Arg Ser Thr Phe Asp Thr Phe Pro Gln
        675                 680                 685

Ala Leu Leu Thr Val Phe Gln Ile Leu Thr Gly Glu Asp Trp Asn Val
        690                 695                 700

Val Met Tyr Asp Gly Ile Met Ala Tyr Gly Gly Pro Phe Phe Pro Gly
705                 710                 715                 720

Met Leu Val Cys Ile Tyr Phe Ile Ile Leu Phe Ile Cys Gly Asn Tyr
                725                 730                 735

Ile Leu Leu Asn Val Phe Leu Ala Ile Ala Val Asp Asn Leu Ala Ser
            740                 745                 750

Gly Asp Ala Gly Thr Ala Lys Asp Lys Gly Gly Glu Lys Ser Asn Glu
        755                 760                 765

Lys Asp Leu Pro Gln Glu Asn Glu Gly Leu Val Pro Gly Val Glu Lys
    770                 775                 780

Glu Glu Glu Glu Gly Ala Arg Arg Glu Gly Ala Asp Met Glu Glu Glu
785                 790                 795                 800

Glu Glu Glu Glu Glu Glu Glu Glu Glu Glu Glu Glu Gly Ala
                805                 810                 815

Gly Gly Val Glu Leu Leu Gln Glu Val Val Pro Lys Glu Lys Val Val
        820                 825                 830

Pro Ile Pro Glu Gly Ser Ala Phe Phe Cys Leu Ser Gln Thr Asn Pro
    835                 840                 845

Leu Arg Lys Gly Cys His Thr Leu Ile His His Val Phe Thr Asn
850                 855                 860

Leu Ile Leu Val Phe Ile Ile Leu Ser Ser Val Ser Leu Ala Ala Glu
865                 870                 875                 880

Asp Pro Ile Arg Ala His Ser Phe Arg Asn His Ile Leu Gly Tyr Phe
            885                 890                 895

Asp Tyr Ala Phe Thr Ser Ile Phe Thr Val Glu Ile Leu Leu Lys Met
                900                 905                 910

Thr Val Phe Gly Ala Phe Leu His Arg Gly Ser Phe Cys Arg Ser Trp
        915                 920                 925

Phe Asn Met Leu Asp Leu Leu Val Val Ser Val Ser Leu Ile Ser Phe
    930                 935                 940

Gly Ile His Ser Ser Ala Ile Ser Val Val Lys Ile Leu Arg Val Leu
```

-continued

```
            945                 950                 955                 960
Arg Val Leu Arg Pro Leu Arg Ala Ile Asn Arg Ala Lys Gly Leu Lys
            965                 970                 975
His Val Val Gln Cys Val Phe Val Ala Ile Arg Thr Ile Gly Asn Ile
            980                 985                 990
Met Ile Val Thr Thr Leu Leu Gln Phe Met Phe Ala Cys Ile Gly Val
            995                 1000                1005
Gln Leu Phe Lys Gly Lys Phe Tyr Thr Cys Thr Asp Glu Ala Lys
    1010                1015                1020
His Thr Pro Gln Glu Cys Lys Gly Ser Phe Leu Val Tyr Pro Asp
    1025                1030                1035
Gly Asp Val Ser Arg Pro Leu Val Arg Glu Arg Leu Trp Val Asn
    1040                1045                1050
Ser Asp Phe Asn Phe Asp Asn Val Leu Ser Ala Met Met Ala Leu
    1055                1060                1065
Phe Thr Val Ser Thr Phe Glu Gly Trp Pro Ala Leu Leu Tyr Lys
    1070                1075                1080
Ala Ile Asp Ala Tyr Ala Glu Asp His Gly Pro Ile Tyr Asn Tyr
    1085                1090                1095
Arg Val Glu Ile Ser Val Phe Phe Ile Val Tyr Ile Ile Ile Ile
    1100                1105                1110
Ala Phe Phe Met Met Asn Ile Phe Val Gly Phe Val Ile Ile Thr
    1115                1120                1125
Phe Arg Ala Gln Gly Glu Gln Glu Tyr Gln Asn Cys Glu Leu Asp
    1130                1135                1140
Lys Asn Gln Arg Gln Cys Val Glu Tyr Ala Leu Lys Ala Gln Pro
    1145                1150                1155
Leu Arg Arg Tyr Ile Pro Lys Asn Pro His Gln Tyr Arg Val Trp
    1160                1165                1170
Ala Thr Val Asn Ser Ala Ala Phe Glu Tyr Leu Met Phe Leu Leu
    1175                1180                1185
Ile Leu Leu Asn Thr Val Ala Leu Ala Met Gln His Tyr Glu Gln
    1190                1195                1200
Thr Ala Pro Phe Asn Tyr Ala Met Asp Ile Leu Asn Met Val Phe
    1205                1210                1215
Thr Gly Leu Phe Thr Ile Glu Met Val Leu Lys Ile Ile Ala Phe
    1220                1225                1230
Lys Pro Lys His Tyr Phe Thr Asp Ala Trp Asn Thr Phe Asp Ala
    1235                1240                1245
Leu Ile Val Val Gly Ser Ile Val Asp Ile Ala Val Thr Glu Val
    1250                1255                1260
Asn Asn Gly Gly His Leu Gly Glu Ser Ser Glu Asp Ser Ser Arg
    1265                1270                1275
Ile Ser Ile Thr Phe Phe Arg Leu Phe Arg Val Met Arg Leu Val
    1280                1285                1290
Lys Leu Leu Ser Lys Gly Glu Gly Ile Arg Thr Leu Leu Trp Thr
    1295                1300                1305
Phe Ile Lys Ser Phe Gln Ala Leu Pro Tyr Val Ala Leu Leu Ile
    1310                1315                1320
Ala Met Ile Phe Phe Ile Tyr Ala Val Ile Gly Met Gln Met Phe
    1325                1330                1335
Gly Lys Val Ala Leu Gln Asp Gly Thr Gln Ile Asn Arg Asn Asn
    1340                1345                1350
```

```
Asn Phe Gln Thr Phe Pro Gln Ala Val Leu Leu Phe Arg Cys
    1355            1360            1365

Ala Thr Gly Glu Ala Trp Gln Glu Ile Met Leu Ala Ser Leu Pro
    1370            1375            1380

Gly Asn Arg Cys Asp Pro Glu Ser Asp Phe Gly Pro Gly Glu Glu
    1385            1390            1395

Phe Thr Cys Gly Ser Asn Phe Ala Ile Ala Tyr Phe Ile Ser Phe
    1400            1405            1410

Phe Met Leu Cys Ala Phe Leu Ile Ile Asn Leu Phe Val Ala Val
    1415            1420            1425

Ile Met Asp Asn Phe Asp Tyr Leu Thr Arg Asp Trp Ser Ile Leu
    1430            1435            1440

Gly Pro His His Leu Asp Glu Phe Lys Arg Ile Trp Ser Glu Tyr
    1445            1450            1455

Asp Pro Gly Ala Lys Gly Arg Ile Lys His Leu Asp Val Val Ala
    1460            1465            1470

Leu Leu Arg Arg Ile Gln Pro Pro Leu Gly Phe Gly Lys Leu Cys
    1475            1480            1485

Pro His Arg Val Ala Cys Lys Arg Leu Val Ala Met Asn Met Pro
    1490            1495            1500

Leu Asn Ser Asp Gly Thr Val Thr Phe Asn Ala Thr Leu Phe Ala
    1505            1510            1515

Leu Val Arg Thr Ser Leu Lys Ile Lys Thr Glu Gly Asn Leu Glu
    1520            1525            1530

Gln Ala Asn Gln Glu Leu Arg Ile Val Ile Lys Lys Ile Trp Lys
    1535            1540            1545

Arg Met Lys Gln Lys Leu Leu Asp Glu Val Ile Pro Pro Pro Asp
    1550            1555            1560

Glu Glu Glu Val Thr Val Gly Lys Phe Tyr Ala Thr Phe Leu Ile
    1565            1570            1575

Gln Asp Tyr Phe Arg Lys Phe Arg Arg Arg Lys Glu Lys Gly Leu
    1580            1585            1590

Leu Gly Asn Asp Ala Ala Pro Ser Thr Ser Ser Ala Leu Gln Ala
    1595            1600            1605

Gly Leu Arg Ser Leu Gln Asp Leu Gly Pro Glu Met Arg Gln Ala
    1610            1615            1620

Leu Thr Cys Asp Thr Glu Glu Glu Glu Glu Gly Gln Glu Gly
    1625            1630            1635

Val Glu Glu Glu Asp Glu Lys Asp Leu Glu Thr Asn Lys Ala Thr
    1640            1645            1650

Met Val Ser Gln Pro Ser Ala Arg Arg Gly Ser Gly Ile Ser Val
    1655            1660            1665

Ser Leu Pro Val Gly Asp Arg Leu Pro Asp Ser Leu Ser Phe Gly
    1670            1675            1680

Pro Ser Asp Asp Asp Arg Gly Thr Pro Thr Ser Ser Gln Pro Ser
    1685            1690            1695

Val Pro Gln Ala Gly Ser Asn Thr His Arg Arg Gly Ser Gly Ala
    1700            1705            1710

Leu Ile Phe Thr Ile Pro Glu Glu Gly Asn Ser Gln Pro Lys Gly
    1715            1720            1725

Thr Lys Gly Gln Asn Lys Gln Asp Glu Asp Glu Glu Val Pro Asp
    1730            1735            1740
```

```
Arg Leu Ser Tyr Leu Asp Glu Gln Ala Gly Thr Pro Pro Cys Ser
    1745                1750                1755

Val Leu Leu Pro Pro His Arg Ala Gln Arg Tyr Met Asp Gly His
    1760                1765                1770

Leu Val Pro Arg Arg Arg Leu Leu Pro Pro Thr Pro Ala Gly Arg
    1775                1780                1785

Lys Pro Ser Phe Thr Ile Gln Cys Leu Gln Arg Gln Gly Ser Cys
    1790                1795                1800

Glu Asp Leu Pro Ile Pro Gly Thr Tyr His Arg Gly Arg Asn Ser
    1805                1810                1815

Gly Pro Asn Arg Ala Gln Gly Ser Trp Ala Thr Pro Pro Gln Arg
    1820                1825                1830

Gly Arg Leu Leu Tyr Ala Pro Leu Leu Leu Val Glu Glu Gly Ala
    1835                1840                1845

Ala Gly Glu Gly Tyr Leu Gly Arg Ser Ser Gly Pro Leu Arg Thr
    1850                1855                1860

Phe Thr Cys Leu His Val Pro Gly Thr His Ser Asp Pro Ser His
    1865                1870                1875

Gly Lys Arg Gly Ser Ala Asp Ser Leu Val Glu Ala Val Leu Ile
    1880                1885                1890

Ser Glu Gly Leu Gly Leu Phe Ala Arg Asp Pro Arg Phe Val Ala
    1895                1900                1905

Leu Ala Lys Gln Glu Ile Ala Asp Ala Cys Arg Leu Thr Leu Asp
    1910                1915                1920

Glu Met Asp Asn Ala Ala Ser Asp Leu Leu Ala Gln Gly Thr Ser
    1925                1930                1935

Ser Leu Tyr Ser Asp Glu Glu Ser Ile Leu Ser Arg Phe Asp Glu
    1940                1945                1950

Glu Asp Leu Gly Asp Glu Met Ala Cys Val His Ala Leu
    1955                1960                1965

<210> SEQ ID NO 33
<211> LENGTH: 2505
<212> TYPE: PRT
<213> ORGANISM: homo sapiens

<400> SEQUENCE: 33

Met Ala Arg Phe Gly Asp Glu Met Pro Ala Arg Tyr Gly Gly Gly
1               5                   10                  15

Ser Gly Ala Ala Ala Gly Val Val Gly Ser Gly Gly Arg Gly
                20                  25                  30

Ala Gly Gly Ser Arg Gln Gly Gly Gln Pro Gly Ala Gln Arg Met Tyr
            35                  40                  45

Lys Gln Ser Met Ala Gln Arg Ala Arg Thr Met Ala Leu Tyr Asn Pro
    50                  55                  60

Ile Pro Val Arg Gln Asn Cys Leu Thr Val Asn Arg Ser Leu Phe Leu
65                  70                  75                  80

Phe Ser Glu Asp Asn Val Val Arg Lys Tyr Ala Lys Lys Ile Thr Glu
                85                  90                  95

Trp Pro Pro Phe Glu Tyr Met Ile Leu Ala Thr Ile Ile Ala Asn Cys
                100                 105                 110

Ile Val Leu Ala Leu Glu Gln His Leu Pro Asp Asp Asp Lys Thr Pro
            115                 120                 125

Met Ser Glu Arg Leu Asp Asp Thr Glu Pro Tyr Phe Ile Gly Ile Phe
    130                 135                 140
```

```
Cys Phe Glu Ala Gly Ile Lys Ile Ile Ala Leu Gly Phe Ala Phe His
145                 150                 155                 160

Lys Gly Ser Tyr Leu Arg Asn Gly Trp Asn Val Met Asp Phe Val Val
            165                 170                 175

Val Leu Thr Gly Ile Leu Ala Thr Val Gly Thr Glu Phe Asp Leu Arg
            180                 185                 190

Thr Leu Arg Ala Val Arg Val Leu Arg Pro Leu Lys Leu Val Ser Gly
        195                 200                 205

Ile Pro Ser Leu Gln Val Val Leu Lys Ser Ile Met Lys Ala Met Ile
    210                 215                 220

Pro Leu Leu Gln Ile Gly Leu Leu Leu Phe Phe Ala Ile Leu Ile Phe
225                 230                 235                 240

Ala Ile Ile Gly Leu Glu Phe Tyr Met Gly Lys Phe His Thr Thr Cys
            245                 250                 255

Phe Glu Glu Gly Thr Asp Asp Ile Gln Gly Glu Ser Pro Ala Pro Cys
            260                 265                 270

Gly Thr Glu Glu Pro Ala Arg Thr Cys Pro Asn Gly Thr Lys Cys Gln
        275                 280                 285

Pro Tyr Trp Glu Gly Pro Asn Asn Gly Ile Thr Gln Phe Asp Asn Ile
    290                 295                 300

Leu Phe Ala Val Leu Thr Val Phe Gln Cys Ile Thr Met Glu Gly Trp
305                 310                 315                 320

Thr Asp Leu Leu Tyr Asn Ser Asn Asp Ala Ser Gly Asn Thr Trp Asn
            325                 330                 335

Trp Leu Tyr Phe Ile Pro Leu Ile Ile Gly Ser Phe Phe Met Leu
            340                 345                 350

Asn Leu Val Leu Gly Val Leu Ser Gly Glu Phe Ala Lys Glu Arg Glu
            355                 360                 365

Arg Val Glu Asn Arg Arg Ala Phe Leu Lys Leu Arg Arg Gln Gln Gln
        370                 375                 380

Ile Glu Arg Glu Leu Asn Gly Tyr Met Glu Trp Ile Ser Lys Ala Glu
385                 390                 395                 400

Glu Val Ile Leu Ala Glu Asp Glu Thr Asp Gly Glu Gln Arg His Pro
            405                 410                 415

Phe Asp Gly Ala Leu Arg Arg Thr Thr Ile Lys Lys Ser Lys Thr Asp
            420                 425                 430

Leu Leu Asn Pro Glu Glu Ala Glu Asp Gln Leu Ala Asp Ile Ala Ser
        435                 440                 445

Val Gly Ser Pro Phe Ala Arg Ala Ser Ile Lys Ser Ala Lys Leu Glu
    450                 455                 460

Asn Ser Thr Phe Phe His Lys Lys Glu Arg Arg Met Arg Phe Tyr Ile
465                 470                 475                 480

Arg Arg Met Val Lys Thr Gln Ala Phe Tyr Trp Thr Val Leu Ser Leu
            485                 490                 495

Val Ala Leu Asn Thr Leu Cys Val Ala Ile Val His Tyr Asn Gln Pro
            500                 505                 510

Glu Trp Leu Ser Asp Phe Leu Tyr Tyr Ala Glu Phe Ile Phe Leu Gly
        515                 520                 525

Leu Phe Met Ser Glu Met Phe Ile Lys Met Tyr Gly Leu Gly Thr Arg
    530                 535                 540

Pro Tyr Phe His Ser Ser Phe Asn Cys Phe Asp Cys Gly Val Ile Ile
545                 550                 555                 560
```

-continued

```
Gly Ser Ile Phe Glu Val Ile Trp Ala Val Ile Lys Pro Gly Thr Ser
                565                 570                 575
Phe Gly Ile Ser Val Leu Arg Ala Leu Arg Leu Leu Arg Ile Phe Lys
            580                 585                 590
Val Thr Lys Tyr Trp Ala Ser Leu Arg Asn Leu Val Val Ser Leu Leu
        595                 600                 605
Asn Ser Met Lys Ser Ile Ile Ser Leu Leu Phe Leu Leu Phe Leu Phe
    610                 615                 620
Ile Val Val Phe Ala Leu Leu Gly Met Gln Leu Phe Gly Gly Gln Phe
625                 630                 635                 640
Asn Phe Asp Glu Gly Thr Pro Pro Thr Asn Phe Asp Thr Phe Pro Ala
                645                 650                 655
Ala Ile Met Thr Val Phe Gln Ile Leu Thr Gly Glu Asp Trp Asn Glu
            660                 665                 670
Val Met Tyr Asp Gly Ile Lys Ser Gln Gly Gly Val Gln Gly Gly Met
        675                 680                 685
Val Phe Ser Ile Tyr Phe Ile Val Leu Thr Leu Phe Gly Asn Tyr Thr
    690                 695                 700
Leu Leu Asn Val Phe Leu Ala Ile Ala Val Asp Asn Leu Ala Asn Ala
705                 710                 715                 720
Gln Glu Leu Thr Lys Asp Glu Gln Glu Glu Glu Ala Ala Asn Gln
                725                 730                 735
Lys Leu Ala Leu Gln Lys Ala Lys Glu Val Ala Glu Val Ser Pro Leu
            740                 745                 750
Ser Ala Ala Asn Met Ser Ile Ala Val Lys Glu Gln Gln Lys Asn Gln
        755                 760                 765
Lys Pro Ala Lys Ser Val Trp Glu Gln Arg Thr Ser Glu Met Arg Lys
    770                 775                 780
Gln Asn Leu Leu Ala Ser Arg Glu Ala Leu Tyr Asn Glu Met Asp Pro
785                 790                 795                 800
Asp Glu Arg Trp Lys Ala Ala Tyr Thr Arg His Leu Arg Pro Asp Met
                805                 810                 815
Lys Thr His Leu Asp Arg Pro Leu Val Val Asp Pro Gln Glu Asn Arg
            820                 825                 830
Asn Asn Asn Thr Asn Lys Ser Arg Ala Ala Glu Pro Thr Val Asp Gln
        835                 840                 845
Arg Leu Gly Gln Gln Arg Ala Glu Asp Phe Leu Arg Lys Gln Ala Arg
    850                 855                 860
Tyr His Asp Arg Ala Arg Asp Pro Ser Gly Ser Ala Gly Leu Asp Ala
865                 870                 875                 880
Arg Arg Pro Trp Ala Gly Ser Gln Glu Ala Glu Leu Ser Arg Glu Gly
                885                 890                 895
Pro Tyr Gly Arg Glu Ser Asp His His Ala Arg Glu Gly Ser Leu Glu
            900                 905                 910
Gln Pro Gly Phe Trp Glu Gly Glu Ala Glu Arg Gly Lys Ala Gly Asp
        915                 920                 925
Pro His Arg Arg His Val His Arg Gln Gly Gly Ser Arg Glu Ser Arg
    930                 935                 940
Ser Gly Ser Pro Arg Thr Gly Ala Asp Gly Glu His Arg Arg His Arg
945                 950                 955                 960
Ala His Arg Arg Pro Gly Glu Glu Gly Pro Glu Asp Lys Ala Glu Arg
                965                 970                 975
Arg Ala Arg His Arg Glu Gly Ser Arg Pro Ala Arg Gly Gly Glu Gly
```

-continued

```
            980             985             990
Glu Gly Glu Gly Pro Asp Gly Gly Glu Arg Arg Arg His Arg His
        995             1000            1005
Gly Ala Pro Ala Thr Tyr Glu Gly Asp Ala Arg Arg Glu Asp Lys
        1010            1015            1020
Glu Arg Arg His Arg Arg Lys Glu Asn Gln Gly Ser Gly Val
        1025            1030            1035
Pro Val Ser Gly Pro Asn Leu Ser Thr Thr Arg Pro Ile Gln Gln
        1040            1045            1050
Asp Leu Gly Arg Gln Asp Pro Pro Leu Ala Glu Asp Ile Asp Asn
        1055            1060            1065
Met Lys Asn Asn Lys Leu Ala Thr Ala Glu Ser Ala Ala Pro His
        1070            1075            1080
Gly Ser Leu Gly His Ala Gly Leu Pro Gln Ser Pro Ala Lys Met
        1085            1090            1095
Gly Asn Ser Thr Asp Pro Gly Pro Met Leu Ala Ile Pro Ala Met
        1100            1105            1110
Ala Thr Asn Pro Gln Asn Ala Ala Ser Arg Arg Thr Pro Asn Asn
        1115            1120            1125
Pro Gly Asn Pro Ser Asn Pro Gly Pro Pro Lys Thr Pro Glu Asn
        1130            1135            1140
Ser Leu Ile Val Thr Asn Pro Ser Gly Thr Gln Thr Asn Ser Ala
        1145            1150            1155
Lys Thr Ala Arg Lys Pro Asp His Thr Thr Val Asp Ile Pro Pro
        1160            1165            1170
Ala Cys Pro Pro Pro Leu Asn His Thr Val Val Gln Val Asn Lys
        1175            1180            1185
Asn Ala Asn Pro Asp Pro Leu Pro Lys Lys Glu Glu Glu Lys Lys
        1190            1195            1200
Glu Glu Glu Glu Asp Asp Arg Gly Glu Asp Gly Pro Lys Pro Met
        1205            1210            1215
Pro Pro Tyr Ser Ser Met Phe Ile Leu Ser Thr Thr Asn Pro Leu
        1220            1225            1230
Arg Arg Leu Cys His Tyr Ile Leu Asn Leu Arg Tyr Phe Glu Met
        1235            1240            1245
Cys Ile Leu Met Val Ile Ala Met Ser Ser Ile Ala Leu Ala Ala
        1250            1255            1260
Glu Asp Pro Val Gln Pro Asn Ala Pro Arg Asn Asn Val Leu Arg
        1265            1270            1275
Tyr Phe Asp Tyr Val Phe Thr Gly Val Phe Thr Phe Glu Met Val
        1280            1285            1290
Ile Lys Met Ile Asp Leu Gly Leu Val Leu His Gln Gly Ala Tyr
        1295            1300            1305
Phe Arg Asp Leu Trp Asn Ile Leu Asp Phe Ile Val Val Ser Gly
        1310            1315            1320
Ala Leu Val Ala Phe Ala Phe Thr Gly Asn Ser Lys Gly Lys Asp
        1325            1330            1335
Ile Asn Thr Ile Lys Ser Leu Arg Val Leu Arg Val Leu Arg Pro
        1340            1345            1350
Leu Lys Thr Ile Lys Arg Leu Pro Lys Leu Lys Ala Val Phe Asp
        1355            1360            1365
Cys Val Val Asn Ser Leu Lys Asn Val Phe Asn Ile Leu Ile Val
        1370            1375            1380
```

-continued

```
Tyr Met Leu Phe Met Phe Ile Phe Ala Val Val Ala Val Gln Leu
    1385            1390            1395

Phe Lys Gly Lys Phe Phe His Cys Thr Asp Glu Ser Lys Glu Phe
    1400            1405            1410

Glu Lys Asp Cys Arg Gly Lys Tyr Leu Leu Tyr Glu Lys Asn Glu
    1415            1420            1425

Val Lys Ala Arg Asp Arg Glu Trp Lys Lys Tyr Glu Phe His Tyr
    1430            1435            1440

Asp Asn Val Leu Trp Ala Leu Leu Thr Leu Phe Thr Val Ser Thr
    1445            1450            1455

Gly Glu Gly Trp Pro Gln Val Leu Lys His Ser Val Asp Ala Thr
    1460            1465            1470

Phe Glu Asn Gln Gly Pro Ser Pro Gly Tyr Arg Met Glu Met Ser
    1475            1480            1485

Ile Phe Tyr Val Val Tyr Phe Val Val Phe Pro Phe Phe Phe Val
    1490            1495            1500

Asn Ile Phe Val Ala Leu Ile Ile Ile Thr Phe Gln Glu Gln Gly
    1505            1510            1515

Asp Lys Met Met Glu Glu Tyr Ser Leu Glu Lys Asn Glu Arg Ala
    1520            1525            1530

Cys Ile Asp Phe Ala Ile Ser Ala Lys Pro Leu Thr Arg His Met
    1535            1540            1545

Pro Gln Asn Lys Gln Ser Phe Gln Tyr Arg Met Trp Gln Phe Val
    1550            1555            1560

Val Ser Pro Pro Phe Glu Tyr Thr Ile Met Ala Met Ile Ala Leu
    1565            1570            1575

Asn Thr Ile Val Leu Met Met Lys Phe Tyr Gly Ala Ser Val Ala
    1580            1585            1590

Tyr Glu Asn Ala Leu Arg Val Phe Asn Ile Val Phe Thr Ser Leu
    1595            1600            1605

Phe Ser Leu Glu Cys Val Leu Lys Val Met Ala Phe Gly Ile Leu
    1610            1615            1620

Asn Tyr Phe Arg Asp Ala Trp Asn Ile Phe Asp Phe Val Thr Val
    1625            1630            1635

Leu Gly Ser Ile Thr Asp Ile Leu Val Thr Glu Phe Gly Asn Asn
    1640            1645            1650

Phe Ile Asn Leu Ser Phe Leu Arg Leu Phe Arg Ala Ala Arg Leu
    1655            1660            1665

Ile Lys Leu Leu Arg Gln Gly Tyr Thr Ile Arg Ile Leu Leu Trp
    1670            1675            1680

Thr Phe Val Gln Ser Phe Lys Ala Leu Pro Tyr Val Cys Leu Leu
    1685            1690            1695

Ile Ala Met Leu Phe Phe Ile Tyr Ala Ile Ile Gly Met Gln Val
    1700            1705            1710

Phe Gly Asn Ile Gly Ile Asp Val Glu Asp Glu Asp Ser Asp Glu
    1715            1720            1725

Asp Glu Phe Gln Ile Thr Glu His Asn Asn Phe Arg Thr Phe Phe
    1730            1735            1740

Gln Ala Leu Met Leu Leu Phe Arg Ser Ala Thr Gly Glu Ala Trp
    1745            1750            1755

His Asn Ile Met Leu Ser Cys Leu Ser Gly Lys Pro Cys Asp Lys
    1760            1765            1770
```

Asn Ser Gly Ile Leu Thr Arg Glu Cys Gly Asn Glu Phe Ala Tyr
1775                1780                1785

Phe Tyr Phe Val Ser Phe Ile Phe Leu Cys Ser Phe Leu Met Leu
1790                1795                1800

Asn Leu Phe Val Ala Val Ile Met Asp Asn Phe Glu Tyr Leu Thr
1805                1810                1815

Arg Asp Ser Ser Ile Leu Gly Pro His His Leu Asp Glu Tyr Val
1820                1825                1830

Arg Val Trp Ala Glu Tyr Asp Pro Ala Ala Trp Gly Arg Met Pro
1835                1840                1845

Tyr Leu Asp Met Tyr Gln Met Leu Arg His Met Ser Pro Pro Leu
1850                1855                1860

Gly Leu Gly Lys Lys Cys Pro Ala Arg Val Ala Tyr Lys Arg Leu
1865                1870                1875

Leu Arg Met Asp Leu Pro Val Ala Asp Asp Asn Thr Val His Phe
1880                1885                1890

Asn Ser Thr Leu Met Ala Leu Ile Arg Thr Ala Leu Asp Ile Lys
1895                1900                1905

Ile Ala Lys Gly Gly Ala Asp Lys Gln Gln Met Asp Ala Glu Leu
1910                1915                1920

Arg Lys Glu Met Met Ala Ile Trp Pro Asn Leu Ser Gln Lys Thr
1925                1930                1935

Leu Asp Leu Leu Val Thr Pro His Lys Ser Thr Asp Leu Thr Val
1940                1945                1950

Gly Lys Ile Tyr Ala Ala Met Met Ile Met Glu Tyr Tyr Arg Gln
1955                1960                1965

Ser Lys Ala Lys Lys Leu Gln Ala Met Arg Glu Glu Gln Asp Arg
1970                1975                1980

Thr Pro Leu Met Phe Gln Arg Met Glu Pro Pro Ser Pro Thr Gln
1985                1990                1995

Glu Gly Gly Pro Gly Gln Asn Ala Leu Pro Ser Thr Gln Leu Asp
2000                2005                2010

Pro Gly Gly Ala Leu Met Ala His Glu Ser Gly Leu Lys Glu Ser
2015                2020                2025

Pro Ser Trp Val Thr Gln Arg Ala Gln Glu Met Phe Gln Lys Thr
2030                2035                2040

Gly Thr Trp Ser Pro Glu Gln Gly Pro Pro Thr Asp Met Pro Asn
2045                2050                2055

Ser Gln Pro Asn Ser Gln Ser Val Glu Met Arg Glu Met Gly Arg
2060                2065                2070

Asp Gly Tyr Ser Asp Ser Glu His Tyr Leu Pro Met Glu Gly Gln
2075                2080                2085

Gly Arg Ala Ala Ser Met Pro Arg Leu Pro Ala Glu Asn Gln Arg
2090                2095                2100

Arg Arg Gly Arg Pro Arg Gly Asn Asn Leu Ser Thr Ile Ser Asp
2105                2110                2115

Thr Ser Pro Met Lys Arg Ser Ala Ser Val Leu Gly Pro Lys Ala
2120                2125                2130

Arg Arg Leu Asp Asp Tyr Ser Leu Glu Arg Val Pro Pro Glu Glu
2135                2140                2145

Asn Gln Arg His His Gln Arg Arg Asp Arg Ser His Arg Ala
2150                2155                2160

Ser Glu Arg Ser Leu Gly Arg Tyr Thr Asp Val Asp Thr Gly Leu

|  | | 2165 | | | 2170 | | | 2175 | | |

Gly Thr Asp Leu Ser Met Thr Thr Gln Ser Gly Asp Leu Pro Ser
    2180                2185                2190

Lys Glu Arg Asp Gln Glu Arg Gly Arg Pro Lys Asp Arg Lys His
2195                2200                2205

Arg Gln His His His His His His His His Pro Pro Pro
    2210                2215                2220

Pro Asp Lys Asp Arg Tyr Ala Gln Glu Arg Pro Asp His Gly Arg
2225                2230                2235

Ala Arg Ala Arg Asp Gln Arg Trp Ser Arg Ser Pro Ser Glu Gly
    2240                2245                2250

Arg Glu His Met Ala His Arg Gln Gly Ser Ser Val Ser Gly
    2255                2260                2265

Ser Pro Ala Pro Ser Thr Ser Gly Thr Ser Thr Pro Arg Arg Gly
    2270                2275                2280

Arg Arg Gln Leu Pro Gln Thr Pro Ser Thr Pro Arg Pro His Val
    2285                2290                2295

Ser Tyr Ser Pro Val Ile Arg Lys Ala Gly Gly Ser Gly Pro Pro
    2300                2305                2310

Gln Gln Gln Gln Gln Gln Gln Gln Gln Gln Ala Val Ala Arg
    2315                2320                2325

Pro Gly Arg Ala Ala Thr Ser Gly Pro Arg Arg Tyr Pro Gly Pro
    2330                2335                2340

Thr Ala Glu Pro Leu Ala Gly Asp Arg Pro Pro Thr Gly Gly His
    2345                2350                2355

Ser Ser Gly Arg Ser Pro Arg Met Glu Arg Arg Val Pro Gly Pro
    2360                2365                2370

Ala Arg Ser Glu Ser Pro Arg Ala Cys Arg His Gly Gly Ala Arg
    2375                2380                2385

Trp Pro Ala Ser Gly Pro His Val Ser Glu Gly Pro Pro Gly Pro
    2390                2395                2400

Arg His His Gly Tyr Tyr Arg Gly Ser Asp Tyr Asp Glu Ala Asp
    2405                2410                2415

Gly Pro Gly Ser Gly Gly Gly Glu Glu Ala Met Ala Gly Ala Tyr
    2420                2425                2430

Asp Ala Pro Pro Val Arg His Ala Ser Ser Gly Ala Thr Gly
    2435                2440                2445

Arg Ser Pro Arg Thr Pro Arg Ala Ser Gly Pro Ala Cys Ala Ser
    2450                2455                2460

Pro Ser Arg His Gly Arg Arg Leu Pro Asn Gly Tyr Tyr Pro Ala
    2465                2470                2475

His Gly Leu Ala Arg Pro Arg Gly Pro Gly Ser Arg Lys Gly Leu
    2480                2485                2490

His Glu Pro Tyr Ser Glu Ser Asp Asp Asp Trp Cys
    2495                2500                2505

<210> SEQ ID NO 34
<211> LENGTH: 2312
<212> TYPE: PRT
<213> ORGANISM: homo sapiens

<400> SEQUENCE: 34

Met Ala Arg Phe Gly Glu Ala Val Val Ala Arg Pro Gly Ser Gly Asp
1               5                   10                  15

-continued

```
Gly Asp Ser Asp Gln Ser Arg Asn Arg Gln Gly Thr Pro Val Pro Ala
         20                  25                  30

Ser Gly Gln Ala Ala Ala Tyr Lys Gln Thr Lys Ala Gln Arg Ala Arg
     35                  40                  45

Thr Met Ala Leu Tyr Asn Pro Ile Pro Val Arg Gln Asn Cys Phe Thr
 50                  55                  60

Val Asn Arg Ser Leu Phe Ile Phe Gly Glu Asp Asn Ile Val Arg Lys
 65                  70                  75                  80

Tyr Ala Lys Lys Leu Ile Asp Trp Pro Phe Glu Tyr Met Ile Leu
                 85                  90                  95

Ala Thr Ile Ile Ala Asn Cys Ile Val Leu Ala Leu Glu Gln His Leu
                100                 105                 110

Pro Glu Asp Asp Lys Thr Pro Met Ser Arg Arg Leu Glu Lys Thr Glu
             115                 120                 125

Pro Tyr Phe Ile Gly Ile Phe Cys Phe Glu Ala Gly Ile Lys Ile Val
         130                 135                 140

Ala Leu Gly Phe Ile Phe His Lys Gly Ser Tyr Leu Arg Asn Gly Trp
145                 150                 155                 160

Asn Val Met Asp Phe Ile Val Val Leu Ser Gly Ile Leu Ala Thr Ala
                 165                 170                 175

Gly Thr His Phe Asn Thr His Val Asp Leu Arg Thr Leu Arg Ala Val
             180                 185                 190

Arg Val Leu Arg Pro Leu Lys Leu Val Ser Gly Ile Pro Ser Leu Gln
         195                 200                 205

Ile Val Leu Lys Ser Ile Met Lys Ala Met Val Pro Leu Leu Gln Ile
     210                 215                 220

Gly Leu Leu Leu Phe Phe Ala Ile Leu Met Phe Ala Ile Ile Gly Leu
225                 230                 235                 240

Glu Phe Tyr Ser Gly Lys Leu His Arg Ala Cys Phe Met Asn Asn Ser
                 245                 250                 255

Gly Ile Leu Glu Gly Phe Asp Pro Pro His Pro Cys Gly Val Gln Gly
             260                 265                 270

Cys Pro Ala Gly Tyr Glu Cys Lys Asp Trp Ile Gly Pro Asn Asp Gly
         275                 280                 285

Ile Thr Gln Phe Asp Asn Ile Leu Phe Ala Val Leu Thr Val Phe Gln
     290                 295                 300

Cys Ile Thr Met Glu Gly Trp Thr Thr Val Leu Tyr Asn Thr Asn Asp
305                 310                 315                 320

Ala Leu Gly Ala Thr Trp Asn Trp Leu Tyr Phe Ile Pro Leu Ile Ile
                 325                 330                 335

Ile Gly Ser Phe Phe Val Leu Asn Leu Val Leu Gly Val Leu Ser Gly
             340                 345                 350

Glu Phe Ala Lys Glu Arg Glu Arg Val Glu Asn Arg Arg Ala Phe Met
         355                 360                 365

Lys Leu Arg Arg Gln Gln Gln Ile Glu Arg Glu Leu Asn Gly Tyr Arg
     370                 375                 380

Ala Trp Ile Asp Lys Ala Glu Glu Val Met Leu Ala Glu Glu Asn Lys
385                 390                 395                 400

Asn Ala Gly Thr Ser Ala Leu Glu Val Leu Arg Arg Ala Thr Ile Lys
                 405                 410                 415

Arg Ser Arg Thr Glu Ala Met Thr Arg Asp Ser Ser Asp Glu His Cys
             420                 425                 430

Val Asp Ile Ser Ser Val Gly Thr Pro Leu Ala Arg Ala Ser Ile Lys
```

-continued

```
            435                 440                 445
Ser Ala Lys Val Asp Gly Val Ser Tyr Phe Arg His Lys Glu Arg Leu
450                     455                 460

Leu Arg Ile Ser Ile Arg His Met Val Lys Ser Gln Val Phe Tyr Trp
465                 470                 475                 480

Ile Val Leu Ser Leu Val Ala Leu Asn Thr Ala Cys Val Ala Ile Val
                485                 490                 495

His His Asn Gln Pro Gln Trp Leu Thr His Leu Leu Tyr Tyr Ala Glu
                500                 505                 510

Phe Leu Phe Leu Gly Leu Phe Leu Leu Glu Met Ser Leu Lys Met Tyr
            515                 520                 525

Gly Met Gly Pro Arg Leu Tyr Phe His Ser Ser Phe Asn Cys Phe Asp
530                 535                 540

Phe Gly Val Thr Val Gly Ser Ile Phe Glu Val Val Trp Ala Ile Phe
545                 550                 555                 560

Arg Pro Gly Thr Ser Phe Gly Ile Ser Val Leu Arg Ala Leu Arg Leu
                565                 570                 575

Leu Arg Ile Phe Lys Ile Thr Lys Tyr Trp Ala Ser Leu Arg Asn Leu
            580                 585                 590

Val Val Ser Leu Met Ser Ser Met Lys Ser Ile Ile Ser Leu Leu Phe
        595                 600                 605

Leu Leu Phe Leu Phe Ile Val Val Phe Ala Leu Leu Gly Met Gln Leu
610                 615                 620

Phe Gly Gly Arg Phe Asn Phe Asn Asp Gly Thr Pro Ser Ala Asn Phe
625                 630                 635                 640

Asp Thr Phe Pro Ala Ala Ile Ile Thr Val Phe Gln Ile Leu Thr Gly
                645                 650                 655

Glu Asp Trp Asn Glu Val Met Tyr Asn Gly Ile Arg Ser Gln Gly Gly
                660                 665                 670

Val Ser Ser Gly Met Trp Ser Ala Ile Tyr Phe Ile Val Leu Thr Leu
        675                 680                 685

Phe Gly Asn Tyr Thr Leu Leu Asn Val Phe Leu Ala Ile Ala Val Asp
690                 695                 700

Asn Leu Ala Asn Ala Gln Glu Leu Thr Lys Asp Glu Gln Glu Glu Glu
705                 710                 715                 720

Glu Ala Phe Asn Gln Lys His Ala Leu Gln Lys Ala Lys Glu Val Ser
                725                 730                 735

Pro Met Ser Ala Pro Asn Met Pro Ser Ile Glu Arg Asp Arg Arg Arg
                740                 745                 750

Arg His His Met Ser Met Trp Glu Pro Arg Ser Ser His Leu Arg Glu
            755                 760                 765

Arg Arg Arg Arg His His Met Ser Val Trp Glu Gln Arg Thr Ser Gln
770                 775                 780

Leu Arg Lys His Met Gln Met Ser Ser Gln Glu Ala Leu Asn Arg Glu
785                 790                 795                 800

Glu Ala Pro Thr Met Asn Pro Leu Asn Pro Leu Asn Pro Leu Ser Ser
                805                 810                 815

Leu Asn Pro Leu Asn Ala His Pro Ser Leu Tyr Arg Arg Pro Arg Ala
                820                 825                 830

Ile Glu Gly Trp Pro Gly Leu Ala Leu Glu Lys Phe Glu Glu Glu Arg
            835                 840                 845

Ile Ser Arg Gly Gly Ser Leu Lys Gly Asp Gly Asp Arg Ser Ser
850                 855                 860
```

-continued

```
Ala Leu Asp Asn Gln Arg Thr Pro Leu Ser Leu Gly Gln Arg Glu Pro
865                 870                 875                 880

Pro Trp Leu Ala Arg Pro Cys His Gly Asn Cys Asp Pro Thr Gln Gln
            885                 890                 895

Glu Ala Gly Gly Gly Glu Ala Val Val Thr Phe Glu Asp Arg Ala Arg
                900                 905                 910

His Arg Gln Ser Gln Arg Arg Ser Arg His Arg Arg Val Arg Thr Glu
            915                 920                 925

Gly Lys Glu Ser Ser Ser Ala Ser Arg Ser Arg Ser Ala Ser Gln Glu
        930                 935                 940

Arg Ser Leu Asp Glu Ala Met Pro Thr Glu Gly Glu Lys Asp His Glu
945                 950                 955                 960

Leu Arg Gly Asn His Gly Ala Lys Glu Pro Thr Ile Gln Glu Glu Arg
                965                 970                 975

Ala Gln Asp Leu Arg Arg Thr Asn Ser Leu Met Val Ser Arg Gly Ser
            980                 985                 990

Gly Leu Ala Gly Gly Leu Asp Glu  Ala Asp Thr Pro Leu  Val Leu Pro
            995                 1000                1005

His Pro  Glu Leu Glu Val Gly  Lys His Val Val Leu  Thr Glu Gln
    1010                1015                1020

Glu Pro  Glu Gly Ser Ser Glu  Gln Ala Leu Leu Gly  Asn Val Gln
    1025                1030                1035

Leu Asp  Met Gly Arg Val Ile  Ser Gln Ser Glu Pro  Asp Leu Ser
    1040                1045                1050

Cys Ile  Thr Ala Asn Thr Asp  Lys Ala Thr Thr Glu  Ser Thr Ser
    1055                1060                1065

Val Thr  Val Ala Ile Pro Asp  Val Asp Pro Leu Val  Asp Ser Thr
    1070                1075                1080

Val Val  His Ile Ser Asn Lys  Thr Asp Gly Glu Ala  Ser Pro Leu
    1085                1090                1095

Lys Glu  Ala Glu Ile Arg Glu  Asp Glu Glu Glu Val  Glu Lys Lys
    1100                1105                1110

Lys Gln  Lys Lys Glu Lys Arg  Glu Thr Gly Lys Ala  Met Val Pro
    1115                1120                1125

His Ser  Ser Met Phe Ile Phe  Ser Thr Thr Asn Pro  Ile Arg Arg
    1130                1135                1140

Ala Cys  His Tyr Ile Val Asn  Leu Arg Tyr Phe Glu  Met Cys Ile
    1145                1150                1155

Leu Leu  Val Ile Ala Ala Ser  Ser Ile Ala Leu Ala  Ala Glu Asp
    1160                1165                1170

Pro Val  Leu Thr Asn Ser Glu  Arg Asn Lys Val Leu  Arg Tyr Phe
    1175                1180                1185

Asp Tyr  Val Phe Thr Gly Val  Phe Thr Phe Glu Met  Val Ile Lys
    1190                1195                1200

Met Ile  Asp Gln Gly Leu Ile  Leu Gln Asp Gly Ser  Tyr Phe Arg
    1205                1210                1215

Asp Leu  Trp Asn Ile Leu Asp  Phe Val Val Val Gly  Ala Leu
    1220                1225                1230

Val Ala  Phe Ala Leu Ala Asn  Ala Leu Gly Thr Asn  Lys Gly Arg
    1235                1240                1245

Asp Ile  Lys Thr Ile Lys Ser  Leu Arg Val Leu Arg  Val Leu Arg
    1250                1255                1260
```

-continued

```
Pro Leu Lys Thr Ile Lys Arg Leu Pro Lys Leu Lys Ala Val Phe
    1265                1270              1275

Asp Cys Val Val Thr Ser Leu Lys Asn Val Phe Asn Ile Leu Ile
    1280                1285              1290

Val Tyr Lys Leu Phe Met Phe Ile Phe Ala Val Ile Ala Val Gln
    1295                1300              1305

Leu Phe Lys Gly Lys Phe Phe Tyr Cys Thr Asp Ser Ser Lys Asp
    1310                1315              1320

Thr Glu Lys Glu Cys Ile Gly Asn Tyr Val Asp His Glu Lys Asn
    1325                1330              1335

Lys Met Glu Val Lys Gly Arg Glu Trp Lys Arg His Glu Phe His
    1340                1345              1350

Tyr Asp Asn Ile Ile Trp Ala Leu Leu Thr Leu Phe Thr Val Ser
    1355                1360              1365

Thr Gly Glu Gly Trp Pro Gln Val Leu Gln His Ser Val Asp Val
    1370                1375              1380

Thr Glu Glu Asp Arg Gly Pro Ser Arg Ser Asn Arg Met Glu Met
    1385                1390              1395

Ser Ile Phe Tyr Val Val Tyr Phe Val Val Phe Pro Phe Phe Phe
    1400                1405              1410

Val Asn Ile Phe Val Ala Leu Ile Ile Ile Thr Phe Gln Glu Gln
    1415                1420              1425

Gly Asp Lys Met Met Glu Glu Cys Ser Leu Glu Lys Asn Glu Arg
    1430                1435              1440

Ala Cys Ile Asp Phe Ala Ile Ser Ala Lys Pro Leu Thr Arg Tyr
    1445                1450              1455

Met Pro Gln Asn Arg His Thr Phe Gln Tyr Arg Val Trp His Phe
    1460                1465              1470

Val Val Ser Pro Ser Phe Glu Tyr Thr Ile Met Ala Met Ile Ala
    1475                1480              1485

Leu Asn Thr Val Val Leu Met Met Lys Tyr Tyr Ser Ala Pro Cys
    1490                1495              1500

Thr Tyr Glu Leu Ala Leu Lys Tyr Leu Asn Ile Ala Phe Thr Met
    1505                1510              1515

Val Phe Ser Leu Glu Cys Val Leu Lys Val Ile Ala Phe Gly Phe
    1520                1525              1530

Leu Asn Tyr Phe Arg Asp Thr Trp Asn Ile Phe Asp Phe Ile Thr
    1535                1540              1545

Val Ile Gly Ser Ile Thr Glu Ile Ile Leu Thr Asp Ser Lys Leu
    1550                1555              1560

Val Asn Thr Ser Gly Phe Asn Met Ser Phe Leu Lys Leu Phe Arg
    1565                1570              1575

Ala Ala Arg Leu Ile Lys Leu Leu Arg Gln Gly Tyr Thr Ile Arg
    1580                1585              1590

Ile Leu Leu Trp Thr Phe Val Gln Ser Phe Lys Ala Leu Pro Tyr
    1595                1600              1605

Val Cys Leu Leu Ile Ala Met Leu Phe Phe Ile Tyr Ala Ile Ile
    1610                1615              1620

Gly Met Gln Val Phe Gly Asn Ile Lys Leu Asp Glu Glu Ser His
    1625                1630              1635

Ile Asn Arg His Asn Asn Phe Arg Ser Phe Phe Gly Ser Leu Met
    1640                1645              1650

Leu Leu Phe Arg Ser Ala Thr Gly Glu Ala Trp Gln Glu Ile Met
```

-continued

```
            1655                1660                1665

Leu Ser Cys Leu Gly Glu Lys Gly Cys Glu Pro Asp Thr Thr Ala
        1670                1675                1680

Pro Ser Gly Gln Asn Glu Asn Glu Arg Cys Gly Thr Asp Leu Ala
        1685                1690                1695

Tyr Val Tyr Phe Val Ser Phe Ile Phe Phe Cys Ser Phe Leu Met
        1700                1705                1710

Leu Asn Leu Phe Val Ala Val Ile Met Asp Asn Phe Glu Tyr Leu
        1715                1720                1725

Thr Arg Asp Ser Ser Ile Leu Gly Pro His His Leu Asp Glu Phe
        1730                1735                1740

Val Arg Val Trp Ala Glu Tyr Asp Arg Ala Ala Cys Gly Arg Ile
        1745                1750                1755

His Tyr Thr Glu Met Tyr Glu Met Leu Thr Leu Met Ser Pro Pro
        1760                1765                1770

Leu Gly Leu Gly Lys Arg Cys Pro Ser Lys Val Ala Tyr Lys Arg
        1775                1780                1785

Leu Val Leu Met Asn Met Pro Val Ala Glu Asp Met Thr Val His
        1790                1795                1800

Phe Thr Ser Thr Leu Met Ala Leu Ile Arg Thr Ala Leu Asp Ile
        1805                1810                1815

Lys Ile Ala Lys Gly Gly Ala Asp Arg Gln Gln Leu Asp Ser Glu
        1820                1825                1830

Leu Gln Lys Glu Thr Leu Ala Ile Trp Pro His Leu Ser Gln Lys
        1835                1840                1845

Met Leu Asp Leu Leu Val Pro Met Pro Lys Ala Ser Asp Leu Thr
        1850                1855                1860

Val Gly Lys Ile Tyr Ala Ala Met Met Ile Met Asp Tyr Tyr Lys
        1865                1870                1875

Gln Ser Lys Val Lys Lys Gln Arg Gln Gln Leu Glu Glu Gln Lys
        1880                1885                1890

Asn Ala Pro Met Phe Gln Arg Met Glu Pro Ser Ser Leu Pro Gln
        1895                1900                1905

Glu Ile Ile Ala Asn Ala Lys Ala Leu Pro Tyr Leu Gln Gln Asp
        1910                1915                1920

Pro Val Ser Gly Leu Ser Gly Arg Ser Gly Tyr Pro Ser Met Ser
        1925                1930                1935

Pro Leu Ser Pro Gln Asp Ile Phe Gln Leu Ala Cys Met Asp Pro
        1940                1945                1950

Thr Asp Asp Gly Gln Phe Gln Glu Arg Gln Ser Leu Glu Pro Glu
        1955                1960                1965

Val Ser Glu Leu Lys Ser Val Gln Pro Ser Asn His Gly Ile Tyr
        1970                1975                1980

Leu Pro Ser Asp Thr Gln Glu His Ala Gly Ser Gly Arg Ala Ser
        1985                1990                1995

Ser Met Pro Arg Leu Thr Val Asp Pro Gln Val Val Thr Asp Pro
        2000                2005                2010

Ser Ser Met Arg Arg Ser Phe Ser Thr Ile Arg Asp Lys Arg Ser
        2015                2020                2025

Asn Ser Ser Trp Leu Glu Glu Phe Ser Met Glu Arg Ser Ser Glu
        2030                2035                2040

Asn Thr Tyr Lys Ser Arg Arg Arg Ser Tyr His Ser Ser Leu Arg
        2045                2050                2055
```

```
Leu Ser Ala His Arg Leu Asn Ser Asp Ser Gly His Lys Ser Asp
    2060                2065                2070

Thr His Arg Ser Gly Gly Arg Glu Arg Gly Arg Ser Lys Glu Arg
    2075                2080                2085

Lys His Leu Leu Ser Pro Asp Val Ser Arg Cys Asn Ser Glu Glu
    2090                2095                2100

Arg Gly Thr Gln Ala Asp Trp Glu Ser Pro Glu Arg Arg Gln Ser
    2105                2110                2115

Arg Ser Pro Ser Glu Gly Arg Ser Gln Thr Pro Asn Arg Gln Gly
    2120                2125                2130

Thr Gly Ser Leu Ser Glu Ser Ser Ile Pro Ser Val Ser Asp Thr
    2135                2140                2145

Ser Thr Pro Arg Arg Ser Arg Arg Gln Leu Pro Pro Val Pro Pro
    2150                2155                2160

Lys Pro Arg Pro Leu Leu Ser Tyr Ser Ser Leu Ile Arg His Ala
    2165                2170                2175

Gly Ser Ile Ser Pro Pro Ala Asp Gly Ser Glu Glu Gly Ser Pro
    2180                2185                2190

Leu Thr Ser Gln Ala Leu Glu Ser Asn Asn Ala Cys Leu Thr Glu
    2195                2200                2205

Ser Ser Asn Ser Pro His Pro Gln Gln Ser Gln His Ala Ser Pro
    2210                2215                2220

Gln Arg Tyr Ile Ser Glu Pro Tyr Leu Ala Leu His Glu Asp Ser
    2225                2230                2235

His Ala Ser Asp Cys Gly Glu Glu Glu Thr Leu Thr Phe Glu Ala
    2240                2245                2250

Ala Val Ala Thr Ser Leu Gly Arg Ser Asn Thr Ile Gly Ser Ala
    2255                2260                2265

Pro Pro Leu Arg His Ser Trp Gln Met Pro Asn Gly His Tyr Arg
    2270                2275                2280

Arg Arg Arg Arg Gly Gly Pro Gly Pro Gly Met Met Cys Gly Ala
    2285                2290                2295

Val Asn Asn Leu Leu Ser Asp Thr Glu Glu Asp Asp Lys Cys
    2300                2305                2310

<210> SEQ ID NO 35
<211> LENGTH: 430
<212> TYPE: PRT
<213> ORGANISM: Anopheles gambiae

<400> SEQUENCE: 35

Met Asn Ala Glu Leu Pro Ala Gly Val His Leu Cys Asn His Asn Glu
1               5                   10                  15

Ser Ala Cys Ile Glu Gln Trp Glu Gly Pro Asn Tyr Gly Ile Thr Asn
            20                  25                  30

Phe Asp Asn Ile Gly Phe Ala Met Leu Thr Val Phe Gln Cys Ile Thr
        35                  40                  45

Met Glu Gly Trp Thr Ser Thr Met Tyr Trp Val Glu Asn Arg Gln Glu
    50                  55                  60

Phe Leu Lys Leu Arg Arg Gln Gln Leu Glu Lys Glu Leu Asn Gly
65                  70                  75                  80

Phe Val Glu Trp Ile Cys Lys Ala Glu Glu Ile Ile Leu Ala Glu Asp
                85                  90                  95

Arg Thr Thr Glu Glu Glu Arg Met Tyr Ile Met Glu Ala Arg Lys Lys
```

-continued

```
                100                 105                 110
Ala Ala Ala Lys Arg Lys Lys Leu Lys Asn Leu Gly Lys Ser Lys Ser
            115                 120                 125

Ser Glu Thr Asp Asp Glu Glu Ala Thr Thr Glu Ser Gly Asp Glu Gly
            130                 135                 140

Ile Leu Lys Lys Glu Lys Lys Pro Ala Lys Ser Gly Phe Trp Arg Ala
145                 150                 155                 160

Glu Lys Arg Phe Arg Tyr Cys Ile Arg His Thr Val Lys Thr Gln Trp
                165                 170                 175

Phe Tyr Trp Phe Val Ile Val Leu Val Phe Leu Asn Thr Ile Cys Val
            180                 185                 190

Ala Val Glu His Tyr Gly Gln Pro Asn Trp Leu Ala Leu Phe Leu Tyr
            195                 200                 205

Tyr Ala Glu Phe Val Phe Leu Gly Leu Phe Met Cys Glu Met Leu Ile
            210                 215                 220

Lys Ile Tyr Ala Leu Gly Pro Arg Ile Tyr Phe Glu Ser Ala Phe Asn
225                 230                 235                 240

Arg Phe Asp Cys Ile Val Ile Ala Gly Ser Ile Phe Glu Val Val Trp
                245                 250                 255

Ser Ala Tyr Lys Glu Gly Ser Phe Gly Ile Ser Val Leu Arg Ala Leu
            260                 265                 270

Arg Leu Leu Arg Ile Phe Lys Val Thr Lys Tyr Trp Ser Ser Leu Arg
            275                 280                 285

Asn Leu Val Ile Ser Leu Leu Ser Ser Met Arg Ser Ile Ile Ser Leu
            290                 295                 300

Leu Phe Leu Leu Phe Leu Phe Ile Leu Ile Phe Ala Leu Leu Gly Met
305                 310                 315                 320

Gln Leu Phe Gly Gly Gln Phe Ile Leu Pro Glu Gly Thr Pro Pro Thr
                325                 330                 335

Asn Phe Asn Thr Phe Thr Ile Ala Leu Leu Thr Val Phe Gln Ile Leu
            340                 345                 350

Thr Gly Glu Asp Trp Asn Glu Val Met Tyr Leu Gly Ile Asn Ser Gln
            355                 360                 365

Gly Gly His Glu Ser Gly Met Ile Tyr Ser Leu Tyr Phe Ile Ile Leu
            370                 375                 380

Thr Leu Phe Gly Asn Tyr Thr Leu Leu Asn Val Phe Leu Ala Ile Ala
385                 390                 395                 400

Val Asp Asn Leu Ala Asn Ala Gln Glu Leu Thr Ala Ala Glu Glu Gln
                405                 410                 415

Gln Gln Glu Arg Asp Lys Glu Lys Gln Gln Met Glu Lys Arg
            420                 425                 430
```

<210> SEQ ID NO 36
<211> LENGTH: 430
<212> TYPE: PRT
<213> ORGANISM: Anopheles gambiae

<400> SEQUENCE: 36

```
Met Asn Ala Glu Leu Pro Ala Gly Val His Leu Cys Asn His Asn Glu
1               5                   10                  15

Ser Ala Cys Ile Glu Gln Trp Glu Gly Pro Asn Tyr Gly Ile Thr Asn
            20                  25                  30

Phe Asp Asn Ile Gly Phe Ala Met Leu Thr Val Phe Gln Cys Ile Thr
            35                  40                  45
```

```
Met Glu Gly Trp Thr Ser Thr Met Tyr Trp Val Asn Arg Gln Glu
 50                  55                  60

Phe Leu Lys Leu Arg Arg Gln Gln Gln Leu Glu Lys Glu Leu Asn Gly
 65                  70                  75                  80

Phe Val Glu Trp Ile Cys Lys Ala Glu Ile Ile Leu Ala Glu Asp
                 85                  90                  95

Arg Thr Thr Glu Glu Glu Arg Met Tyr Ile Met Glu Ala Arg Lys Lys
                100                 105                 110

Ala Ala Ala Lys Arg Lys Lys Leu Lys Asn Leu Gly Lys Ser Lys Ser
            115                 120                 125

Ser Glu Thr Asp Asp Glu Glu Ala Thr Thr Glu Ser Gly Asp Glu Gly
130                 135                 140

Ile Leu Lys Lys Glu Lys Lys Pro Ala Lys Ser Gly Phe Trp Arg Ala
145                 150                 155                 160

Glu Lys Arg Phe Arg Tyr Cys Ile Arg His Thr Val Lys Thr Gln Trp
                165                 170                 175

Phe Tyr Trp Phe Val Ile Val Leu Val Phe Leu Asn Thr Ile Cys Val
                180                 185                 190

Ala Val Glu His Tyr Gly Gln Pro Asn Trp Leu Ala Leu Phe Leu Tyr
            195                 200                 205

Tyr Ala Glu Phe Val Phe Leu Gly Leu Phe Met Cys Glu Met Leu Ile
210                 215                 220

Lys Ile Tyr Ala Leu Gly Pro Arg Ile Tyr Phe Glu Ser Ala Phe Asn
225                 230                 235                 240

Arg Phe Asp Cys Ile Val Ile Ala Gly Ser Ile Phe Glu Val Val Trp
                245                 250                 255

Ser Ala Tyr Lys Glu Gly Ser Phe Gly Ile Ser Val Leu Arg Ala Leu
                260                 265                 270

Arg Leu Leu Arg Ile Phe Lys Val Thr Lys Tyr Trp Ser Ser Leu Arg
            275                 280                 285

Asn Leu Val Ile Ser Leu Leu Ser Ser Met Arg Ser Ile Ile Ser Leu
290                 295                 300

Leu Phe Leu Leu Phe Leu Phe Ile Leu Ile Phe Ala Leu Leu Gly Met
305                 310                 315                 320

Gln Leu Phe Gly Gly Gln Phe Ile Leu Pro Glu Gly Thr Pro Pro Thr
                325                 330                 335

Asn Phe Asn Thr Phe Thr Ile Ala Leu Leu Thr Val Phe Gln Ile Leu
                340                 345                 350

Thr Gly Glu Asp Trp Asn Glu Val Met Tyr Leu Gly Ile Asn Ser Gln
            355                 360                 365

Gly Gly His Glu Ser Gly Met Ile Tyr Ser Leu Tyr Phe Ile Ile Leu
370                 375                 380

Thr Leu Phe Gly Asn Tyr Thr Leu Leu Asn Val Phe Leu Ala Ile Ala
385                 390                 395                 400

Val Asp Asn Leu Ala Asn Ala Gln Glu Leu Thr Ala Ala Glu Glu Gln
                405                 410                 415

Gln Gln Glu Arg Asp Lys Glu Lys Gln Gln Met Glu Lys Arg
                420                 425                 430

<210> SEQ ID NO 37
<211> LENGTH: 2326
<212> TYPE: PRT
<213> ORGANISM: Discopyge ommata

<400> SEQUENCE: 37
```

```
Met Ala Arg Leu Gly Asn Asp Val Pro Ala Cys Tyr Gly Gly Ser Pro
1               5                   10                  15

Ala Gly Gly Arg Gly Ala Asn Arg His Ala Gly Pro Gln Ala Gly
            20                  25                  30

Gln Arg Gly Met Tyr Gly Ser Lys Ser Leu Ala Gln Arg Ala Arg Thr
        35                  40                  45

Met Ala Leu Tyr Asn Pro Ile Pro Val Arg Gln Asn Cys Leu Thr Val
50                  55                  60

Asn Arg Ser Leu Phe Ile Phe Ser Glu Asp Asn Ile Ile Arg Lys Tyr
65              70                  75                  80

Ala Lys Arg Ile Thr Glu Trp Pro Pro Phe Glu Tyr Met Ile Leu Ala
                85                  90                  95

Thr Ile Ile Ala Asn Cys Ile Val Leu Ala Leu Glu Gln His Leu Pro
                100                 105                 110

Asp Gly Asp Lys Thr Pro Met Ser Glu Arg Leu Asp Asp Thr Glu Pro
            115                 120                 125

Tyr Phe Ile Gly Ile Phe Cys Phe Glu Ala Gly Ile Lys Ile Ile Ala
130                 135                 140

Leu Gly Phe Ala Phe His Lys Gly Ser Tyr Leu Arg Asn Gly Trp Asn
145                 150                 155                 160

Val Met Asp Phe Val Val Leu Thr Gly Ile Leu Thr Thr Ile Gly
                165                 170                 175

Thr Asp Phe Asp Leu Arg Thr Leu Arg Ala Val Arg Val Leu Arg Pro
            180                 185                 190

Leu Lys Leu Val Ser Gly Ile Pro Ser Leu Gln Val Val Leu Lys Ser
    195                 200                 205

Ile Met Lys Ala Met Val Pro Leu Leu Gln Ile Gly Leu Leu Leu Phe
    210                 215                 220

Phe Ala Ile Leu Met Phe Ala Ile Ile Gly Leu Glu Phe Tyr Met Gly
225                 230                 235                 240

Lys Phe His Lys Thr Cys Phe Ser Glu Glu Thr Asn Glu Pro Val Glu
                245                 250                 255

Glu Phe Pro Cys Gly Thr Lys Tyr Pro Ser Arg Leu Cys Pro Asn Gly
            260                 265                 270

Thr Val Cys Lys Gly Tyr Trp Asn Gly Pro Asn Phe Gly Ile Thr Asn
        275                 280                 285

Phe Asp Asn Ile Leu Phe Ala Val Leu Thr Val Phe Gln Cys Ile Thr
    290                 295                 300

Met Glu Gly Trp Thr Asp Met Leu Tyr Thr Ala Asn Asp Ala Leu Gly
305                 310                 315                 320

Asn Thr Trp Asn Trp Leu Tyr Phe Ile Pro Leu Ile Val Ile Gly Ser
                325                 330                 335

Phe Phe Met Leu Asn Leu Val Leu Gly Val Leu Ser Gly Glu Phe Ala
            340                 345                 350

Lys Glu Arg Glu Arg Val Glu Asn Arg Arg Ala Phe Leu Lys Leu Arg
        355                 360                 365

Arg Gln Gln Gln Val Glu Gln Glu Phe Asn Arg Tyr Leu Arg Trp Ile
    370                 375                 380

His Ile Ala Glu Glu Val Met Leu Ala Glu Gly Asp Lys Asn Ala Glu
385                 390                 395                 400

Asp Lys Cys Ala Leu Asp Val Leu Lys Arg Ala Thr Thr Lys Lys Ser
            405                 410                 415
```

-continued

```
Lys Asn Asp Leu Ile Asn Ala Glu Glu Gly Glu Asp His Phe Thr Asp
            420                 425                 430

Ile Ser Ser Val Gly Phe Asn Arg Pro Ser Leu Lys Ser Val Lys Asn
            435                 440                 445

Glu Arg Ser Ser Tyr Phe Arg Arg Lys Glu Lys Arg Phe Arg Phe Phe
        450                 455                 460

Ile Arg Arg Met Val Lys Ser Gln Ser Phe Tyr Trp Ile Val Leu Cys
465                 470                 475                 480

Leu Val Gly Leu Asn Thr Leu Cys Val Ala Ile Val His Tyr Asp Gln
                485                 490                 495

Pro Pro Leu Leu Thr Asp Ala Leu Tyr Phe Ala Glu Phe Val Phe Leu
            500                 505                 510

Gly Leu Phe Leu Thr Glu Met Ser Leu Lys Met Tyr Gly Leu Gly Pro
            515                 520                 525

Arg Asn Tyr Phe His Ser Ser Phe Asn Cys Phe Asp Phe Gly Val Ile
        530                 535                 540

Val Gly Ser Ile Phe Glu Val Val Trp Thr Ala Val Lys Pro Asp Thr
545                 550                 555                 560

Ser Phe Gly Ile Ser Val Leu Arg Ala Leu Arg Leu Leu Arg Ile Phe
                565                 570                 575

Lys Val Thr Lys Tyr Trp Asn Ser Leu Arg Asn Leu Val Val Ser Leu
            580                 585                 590

Leu Asn Ser Met Lys Ser Ile Ile Ser Leu Leu Phe Leu Leu Phe Leu
            595                 600                 605

Phe Ile Val Val Phe Ala Leu Leu Gly Met Gln Leu Phe Gly Gly Gln
        610                 615                 620

Phe Asn Phe Glu Asp Gly Thr Pro Pro Thr Asn Phe Asp Thr Phe Pro
625                 630                 635                 640

Ala Ala Ile Leu Thr Val Phe Gln Ile Leu Thr Gly Glu Asp Trp Asn
                645                 650                 655

Glu Val Met Tyr Tyr Gly Ile Glu Ala His Gly Gly Val Lys Lys Gly
            660                 665                 670

Met Phe Ser Ser Val Tyr Phe Ile Ile Leu Thr Leu Phe Gly Asn Tyr
            675                 680                 685

Thr Leu Leu Asn Val Phe Leu Ala Ile Ala Val Asp Asn Leu Ala Asn
        690                 695                 700

Ala Gln Glu Leu Thr Lys Asp Glu Glu Glu Met Glu Glu Ala Asn Ile
705                 710                 715                 720

Gln Lys Asn Thr Ile Gln Lys Ala Met Glu Val Ala Asp Val Ser Pro
                725                 730                 735

Ile Ser Ala Thr Asn Leu Ser Ile Ala Ala Lys Asp Gln Gln Lys Ser
            740                 745                 750

Phe Lys Ser Met Ser Ile Trp Glu Gln Arg Thr Ser Gln Leu Arg Arg
            755                 760                 765

Gln His Ile Leu Thr Ser Gln Glu Ala Leu Phe Asn Glu Leu Asp Asp
        770                 775                 780

Glu Gln Arg Arg Met Tyr Val Ser Ser His Gln Ile Arg Pro Asp Met
785                 790                 795                 800

Lys Thr His Leu Asp Arg Pro Leu Val Val Glu Pro Arg Asn Ser Thr
                805                 810                 815

Arg Lys Ser Ala Asp Lys Val Cys Pro Ser Asp Cys Gln Glu Gly Glu
            820                 825                 830

Gln Glu Arg Leu Val Gln Pro Glu Ser Cys Glu Ala Pro Arg Arg Ser
```

-continued

```
            835                 840                 845
His Arg His Arg Asp Lys Leu Gly Glu Gln Asp Lys Gly Asp Gly Ala
850                 855                 860

Leu Asp Thr Gly Glu Pro Arg Ala Asn Ser Lys Asp Lys Arg Cys
865                 870                 875                 880

Ser His Arg Ser His Ser Lys Glu Thr Glu Lys Glu Arg Asp Glu Lys
                885                 890                 895

Gly Arg Lys Gly Glu Arg Ser Arg Ser His Gly Gly Arg Arg His
                900                 905                 910

His His Ala Gln Ser Ser Leu Asp Asp Ala Pro Glu Arg Glu His Arg
                915                 920                 925

Arg His Arg Ser His Arg His Gly Thr Glu Gln Gln His Arg Glu Ala
930                 935                 940

Asn Gly Thr Lys Gly Glu Arg His Ser Arg Ala Lys Asp Gly Ser Arg
945                 950                 955                 960

Ser Gly Gly Arg Glu Gly Glu Ala Val Ser Arg Ser His Ala Glu
                965                 970                 975

Gly Ala Glu Arg Arg Arg Lys His Arg Gln Lys Val Ala Ser Thr Asn
                980                 985                 990

Glu Ser Glu Glu Lys Arg Glu Ile  Gly Glu Lys Glu Arg  Glu Thr Val
                995                 1000                1005

Leu Arg  Glu Arg Arg Val His  Arg Val Lys Glu Thr  Gln Pro Ser
    1010                1015                1020

Gln Asp  Ser Gly Thr Gln Gly  Asn Val Ser Leu Pro  Pro Ile Gly
    1025                1030                1035

Leu Gln  His Leu Pro Gln Gln  Pro Glu Asp Ala Asp  Asn Gln Lys
    1040                1045                1050

Asn Ile  Lys Leu Val Thr Leu  Pro Thr Gly Asp Ala  Gln Asn Pro
    1055                1060                1065

Ala Thr  Val Asn Ile Pro Val  Thr Val Thr Pro Ala  Ala Glu
    1070                1075                1080

Met Thr  Leu Leu Pro Ile Asn  Asn Val Ala Val Asp  Leu Glu Asn
    1085                1090                1095

Val Met  Lys Pro Glu Glu Lys  Lys Ala Glu Asn Gly  Asp Asp Leu
    1100                1105                1110

Asn Glu  Asp Gly Pro Arg Gln  Ile Pro Pro Phe Asn  Ser Met Phe
    1115                1120                1125

Leu Phe  Ser Thr Thr Asn Pro  Val Arg Arg Ala Cys  His Tyr Ile
    1130                1135                1140

Val Asn  Leu Arg Tyr Phe Glu  Met Cys Ile Leu Leu  Val Ile Thr
    1145                1150                1155

Met Ser  Ser Ile Ala Leu Ala  Ala Glu Asp Pro Val  Gln Gly Asp
    1160                1165                1170

Ala Pro  Arg Asn Asn Val Leu  Lys Tyr Leu Asp Tyr  Val Phe Thr
    1175                1180                1185

Gly Val  Phe Thr Phe Glu Met  Val Ile Lys Met Ile  Asn Leu Gly
    1190                1195                1200

Leu Ile  Leu His Pro Gly Ser  Tyr Phe Arg Asp Leu  Trp Asn Ile
    1205                1210                1215

Leu Asp  Phe Ile Val Val Ser  Gly Ala Leu Val Ala  Phe Ala Phe
    1220                1225                1230

Thr Gly  Ser Arg Gly Lys Asp  Leu Asn Thr Ile Lys  Ser Leu Arg
    1235                1240                1245
```

-continued

```
Val Leu Arg Val Leu Arg Pro Leu Lys Thr Ile Lys Arg Leu Pro
    1250                1255                1260

Lys Leu Lys Ala Val Phe Asp Cys Val Val Asn Ser Leu Lys Asn
    1265                1270                1275

Val Leu Asn Ile Leu Ile Val Tyr Met Leu Phe Met Phe Ile Phe
    1280                1285                1290

Ala Val Ile Ala Val Gln Leu Phe Lys Gly Lys Phe Phe Tyr Cys
    1295                1300                1305

Thr Asp Glu Ser Lys Asp Leu Glu Lys Asp Cys Arg Gly Gln Tyr
    1310                1315                1320

Leu Val Tyr Asp Asn Asp Glu Ile Glu Ala Glu Pro Arg Glu Trp
    1325                1330                1335

Lys Lys Cys Asp Phe His Tyr Asp Asn Val Leu Trp Ala Leu Leu
    1340                1345                1350

Thr Leu Phe Thr Val Ser Thr Gly Glu Gly Trp Pro Thr Val Leu
    1355                1360                1365

Lys Asn Ser Ile Asp Ala Thr Glu Glu Asp Gln Gly Pro Ser Pro
    1370                1375                1380

Ser Tyr Arg Met Glu Met Ser Ile Phe Tyr Val Val Tyr Phe Val
    1385                1390                1395

Val Phe Pro Phe Phe Phe Val Asn Ile Phe Val Ala Leu Ile Ile
    1400                1405                1410

Ile Thr Phe Gln Glu Gln Gly Asp Lys Val Met Ser Asp Cys Ser
    1415                1420                1425

Leu Glu Lys Asn Glu Arg Ala Cys Ile Asp Phe Ala Ile Ser Ala
    1430                1435                1440

Lys Pro Leu Thr Arg Tyr Met Pro Gln Asn Lys Gln Thr Phe Gln
    1445                1450                1455

Tyr Lys Met Trp Lys Phe Val Val Ser Pro Pro Phe Glu Tyr Leu
    1460                1465                1470

Ile Met Ala Leu Ile Ala Leu Asn Thr Ile Val Leu Met Met Lys
    1475                1480                1485

Phe Tyr Asn Ala Pro Asp Pro Tyr Asp Arg Met Leu Gln Tyr Leu
    1490                1495                1500

Asn Ile Leu Phe Thr Phe Leu Phe Ser Met Glu Cys Val Leu Lys
    1505                1510                1515

Leu Ile Gly Phe Gly Val Leu Asn Tyr Phe Arg Asp Ala Trp Asn
    1520                1525                1530

Val Phe Asp Phe Val Thr Val Leu Gly Ser Ile Thr Asp Ile Leu
    1535                1540                1545

Val Thr Glu Leu Ala Asp Ser Phe Ile Asn Leu Ser Phe Leu Arg
    1550                1555                1560

Leu Phe Arg Ala Ala Arg Leu Ile Lys Leu Leu Arg Gln Gly Tyr
    1565                1570                1575

Thr Ile Arg Ile Leu Leu Trp Thr Phe Val Gln Ser Phe Lys Ala
    1580                1585                1590

Leu Pro Tyr Val Cys Leu Leu Ile Ala Met Leu Phe Phe Ile Tyr
    1595                1600                1605

Ala Ile Ile Gly Met Gln Val Phe Gly Asn Ile Glu Leu Asp Asp
    1610                1615                1620

Asp Gly Ala Ile Asn Arg His Asn Asn Phe Arg Thr Phe Leu Gln
    1625                1630                1635
```

```
Ala Val Met Leu Leu Leu Arg Ser Ala Thr Gly Glu Gly Trp Gln
1640                1645                1650

Glu Ile Met Leu Ala Cys Leu Asn Gln Ser Pro Cys Asp Ala Arg
1655                1660                1665

Ser Gly Ile Asp Gly Asp Cys Gly Ser Asn Phe Ala Tyr Phe
1670                1675                1680

Tyr Phe Val Ser Phe Ile Phe Phe Ser Ser Phe Leu Met Leu Asn
1685                1690                1695

Leu Phe Val Ala Val Ile Met Asp Asn Phe Glu Tyr Leu Thr Arg
1700                1705                1710

Asp Ser Ser Ile Leu Gly Pro His His Leu Asp Glu Phe Ile Arg
1715                1720                1725

Val Trp Ala Glu Tyr Asp Pro Gly Ala Arg Gly Arg Ile Thr Tyr
1730                1735                1740

Asn Asp Met Tyr Glu Met Leu Arg His Met Cys Pro Pro Leu Gly
1745                1750                1755

Leu Gly Lys Lys Cys Pro Ala Arg Val Ala Tyr Lys Arg Leu Val
1760                1765                1770

Arg Met Asn Met Pro Ile Ala Glu Asp Gly Ser Val His Phe Thr
1775                1780                1785

Ser Thr Leu Met Ala Leu Ile Arg Thr Ala Leu Asp Val Lys Ile
1790                1795                1800

Ser Pro Gly Gly Ala Tyr Gln Gln Cys Asp Ala Glu Leu Arg
1805                1810                1815

Lys Glu Ile Thr Ala Val Trp Pro Asn Leu Ser Gln Lys Phe Leu
1820                1825                1830

Asp Ile Leu Val Pro Pro Gln Arg Ala Ser Glu Leu Thr Val Gly
1835                1840                1845

Lys Val Tyr Ala Ala Leu Met Ile Tyr Asp Tyr Tyr Lys Gln Asn
1850                1855                1860

Lys Ser Lys Lys Val Gln Gln Gln Gln Leu Ser Gly Leu Ser
1865                1870                1875

Gln Thr Arg Lys Ser Phe Phe Gln Arg Val Val Gly Val Leu Ala
1880                1885                1890

Ala Thr Gln Glu Glu Pro Ser Ser Tyr Ser Thr Ser His Lys Asn
1895                1900                1905

Ser Val Asn Pro Leu Tyr Gln Gly Gly Arg Gln Lys Glu Pro Phe
1910                1915                1920

Ser Trp Leu Arg Ser Arg Asp Thr Cys Ala Glu Gly Lys Lys Glu
1925                1930                1935

Val Pro Glu Ser His Pro Glu Glu Ala Gly Val Thr Lys Ser Ser
1940                1945                1950

Ser Gln Ala Val Glu Met Arg Glu Met Gly Ser Asp Leu Asn His
1955                1960                1965

Ala Asp Gln Ser Ser Leu Glu Asn Tyr Gly Arg Ala Ala Ser Met
1970                1975                1980

Pro Arg Leu Thr Ala Glu Thr Gln Lys Ile Ser Arg Pro Ser Gly
1985                1990                1995

Arg Val Arg Ala Pro Ile Ala Asp Thr Ser Pro Met Lys Arg Ser
2000                2005                2010

Val Ser Thr Leu Thr Pro Gln Arg Ser His Val Met Pro Asp Tyr
2015                2020                2025

Ser Leu Glu Arg Val Ile Pro Val Gln Met Pro His His His His
```

```
                2030                2035                2040
            His His His Arg Cys His His Arg Arg Glu Lys Lys Gln Arg Ser
                2045                2050                2055

Leu Glu Arg Ala Thr Asn Arg His Ala Asp Glu Glu Ala Gly Gln
                2060                2065                2070

Leu Asp Ala Gln Leu Arg Asp Gln Ser Ser Lys Glu Arg Glu Arg
                2075                2080                2085

Gly Arg Ser Gln Glu Arg Arg Pro Pro Ser Ser Ala Glu Lys Gln
                2090                2095                2100

Arg Tyr Tyr Ser Cys Asp Arg Tyr Gly Ser Arg Glu Pro Pro Gln
                2105                2110                2115

Pro Arg Ser Thr Asp His Ser Arg Ser Ala Ser Pro Ser Thr Gly
                2120                2125                2130

Thr Glu Gln Gly Phe His Arg Gln Gly Ser Gly Ser Val Asn Asp
                2135                2140                2145

Ser Pro Leu Gln Ser Ala Ser Gly Ser Ser Thr Pro Ser Arg Gly
                2150                2155                2160

Arg Arg Gln Leu Pro Arg Thr Pro Leu Thr Pro Arg Pro Ser Val
                2165                2170                2175

Thr Tyr Lys Thr Ala Asn Ser Ser Pro Ala His Phe Gly Asn Leu
                2180                2185                2190

His Asp Ala Leu Pro Pro Ser Ser Pro Gly Arg Leu Ser Arg Gly
                2195                2200                2205

Gln Ser Glu His Asn His Leu Leu Ser Gly Glu Ser Gln Asn Arg
                2210                2215                2220

Pro Tyr Ala Gly Gly Asp Ser Arg Gln Pro Met Gly Thr Arg Ile
                2225                2230                2235

Ser Ser Asp Pro Tyr Leu Gly Phe Arg Ser Ser Cys Gly Ser Glu
                2240                2245                2250

Asp Leu Glu Leu Leu Glu Glu Thr Leu Thr Phe Glu Val Ala Val
                2255                2260                2265

Ala Ala Thr Thr Ala Thr Gly Arg Ser Pro Arg Thr Ser Ser Phe
                2270                2275                2280

Thr Thr Gln Pro Pro Gln Ser Arg Arg Val Pro Asn Gly Tyr His
                2285                2290                2295

Cys Asn Leu Gly Arg Ser Thr Gly Pro Ser Thr Ala Ala Ser Lys
                2300                2305                2310

Arg Lys Tyr Tyr Arg Glu Thr Asp Glu Asp Trp Cys
                2315                2320                2325

<210> SEQ ID NO 38
<211> LENGTH: 1783
<212> TYPE: PRT
<213> ORGANISM: Caenorhabditis elegans

<400> SEQUENCE: 38

Met Ser Val Leu Ala Ser Met Met Ser Ser Gly Glu Asp Glu Glu Gln
1               5                   10                  15

Ala Ala Ala Asp Glu Gln Glu Arg Thr Asp Leu Trp Gln Gln Thr Leu
                20                  25                  30

Gln Ala Ala Val Ala Ala Ser Ser Gln Asp Ala Thr Lys Lys Arg
            35                  40                  45

Pro Ala Gln Arg Lys Pro Leu Arg Gln Thr Asn Val Val Glu Arg Ser
        50                  55                  60
```

-continued

```
Glu Arg Ser Leu Leu Cys Leu Ser Leu Asn Asn Pro Ile Arg Lys Leu
 65                  70                  75                  80

Cys Ile Ser Ile Val Glu Trp Lys Pro Phe Glu Phe Leu Ile Leu Phe
                 85                  90                  95

Met Ile Cys Ala Asn Cys Ile Ala Leu Ala Ile Tyr Gln Pro Tyr Pro
            100                 105                 110

Ala Gln Asp Ser Asp Tyr Lys Asn Thr Leu Leu Glu Thr Ile Glu Tyr
        115                 120                 125

Val Phe Ile Val Val Phe Thr Ile Glu Cys Val Leu Lys Ile Val Ala
    130                 135                 140

Met Gly Phe Met Phe His Pro Ser Ala Tyr Leu Arg Asn Ala Trp Asn
145                 150                 155                 160

Ile Leu Asp Phe Ile Ile Val Val Ile Gly Leu Val Ser Thr Ile Leu
                165                 170                 175

Ser Lys Met Ser Ile Gln Gly Phe Asp Val Lys Ala Leu Arg Ala Phe
            180                 185                 190

Arg Val Leu Arg Pro Leu Arg Leu Val Ser Gly Val Pro Ser Leu Gln
        195                 200                 205

Val Val Leu Asn Ala Ile Leu Arg Ala Met Ile Pro Leu Leu His Ile
    210                 215                 220

Ala Leu Leu Val Leu Phe Val Ile Leu Ile Tyr Ala Ile Ile Gly Leu
225                 230                 235                 240

Glu Leu Phe Cys Gly Lys Leu His Ser Thr Cys Ile Asp Pro Ala Thr
                245                 250                 255

Gly Gln Leu Ala Gln Lys Asp Pro Thr Pro Cys Gly Thr Asp Thr Glu
            260                 265                 270

Gly Ser Ala Phe Lys Cys Gln Pro Ser Asp Ser Leu Thr Asn Met Gly
        275                 280                 285

Val Arg Trp Glu Cys Ser Ser Asn Thr Thr Trp Pro Gly Pro Asn Asn
    290                 295                 300

Gly Ile Thr Asn Phe Asp Asn Phe Gly Leu Ala Met Leu Thr Val Phe
305                 310                 315                 320

Gln Cys Val Ser Leu Glu Gly Trp Thr Asp Val Met Tyr Trp Val Asn
                325                 330                 335

Asp Ala Val Gly Arg Glu Trp Pro Trp Ile Tyr Phe Val Thr Leu Val
            340                 345                 350

Ile Leu Gly Ser Phe Phe Val Leu Asn Leu Val Leu Gly Val Leu Ser
        355                 360                 365

Gly Glu Phe Ser Lys Glu Arg Glu Lys Ala Arg Ala Arg Gly Leu Phe
    370                 375                 380

Gln Lys Phe Arg Glu Lys Gln Gln Leu Glu Glu Asp Leu Lys Gly Tyr
385                 390                 395                 400

Leu Asp Trp Ile Thr Gln Ala Glu Asp Ile Glu Pro Val Asn Glu Asp
                405                 410                 415

Glu Gln Glu Asp Glu Pro Val Ala Gln Thr Val Val Gly Glu Glu Ala
            420                 425                 430

Asp Glu Glu Gly Glu Glu Arg Val Glu Asp Val Arg Pro Ser Lys Trp
        435                 440                 445

Ala Ala Arg Met Lys Arg Leu Glu Lys Leu Asn Arg Cys Arg Arg
    450                 455                 460

Ala Cys Arg Arg Leu Val Lys Ser Gln Thr Phe Tyr Trp Leu Val Ile
465                 470                 475                 480

Leu Leu Val Leu Leu Asn Thr Leu Val Leu Thr Ser Glu His Tyr Gly
```

```
                    485                 490                 495
Gln Ser Glu Trp Leu Asp His Phe Gln Thr Met Ala Asn Leu Phe Phe
            500                 505                 510

Val Ile Leu Phe Ser Met Glu Met Leu Leu Lys Met Tyr Ser Leu Gly
            515                 520                 525

Phe Thr Thr Tyr Thr Thr Ser Gln Phe Asn Arg Phe Asp Cys Phe Val
            530                 535                 540

Val Ile Ser Ser Ile Leu Glu Phe Val Leu Val Tyr Phe Asp Leu Met
545                 550                 555                 560

Lys Pro Leu Gly Val Ser Val Leu Arg Ser Ala Arg Leu Leu Arg Ile
            565                 570                 575

Phe Lys Val Thr Lys Tyr Trp Thr Ser Leu Arg Asn Leu Val Ser Ser
            580                 585                 590

Leu Leu Asn Ser Leu Arg Ser Ile Ile Ser Leu Leu Leu Leu Leu Phe
            595                 600                 605

Leu Phe Ile Val Ile Phe Ala Leu Leu Gly Met Gln Val Phe Gly Gly
            610                 615                 620

Lys Phe Asn Phe Asn Pro Gln Gln Pro Lys Pro Arg Ala Asn Phe Asp
625                 630                 635                 640

Thr Phe Val Gln Ala Leu Leu Thr Val Phe Gln Ile Leu Thr Gly Glu
            645                 650                 655

Asp Trp Asn Thr Val Met Tyr His Gly Ile Glu Ser Phe Gly Gly Val
            660                 665                 670

Gly Thr Leu Gly Val Ile Val Cys Ile Tyr Tyr Ile Val Leu Phe Ile
            675                 680                 685

Cys Gly Asn Tyr Ile Leu Leu Asn Val Phe Leu Ala Ile Ala Val Asp
            690                 695                 700

Asn Leu Ala Asp Ala Asp Ser Leu Thr Asn Ala Glu Lys Glu Glu Glu
705                 710                 715                 720

Gln Gln Glu Ile Glu Gly Glu Asp Glu Phe Glu Glu Gly Glu Asp
            725                 730                 735

Glu Gly Glu Glu His Gly Met Asp Glu Pro Glu Gly Asp Glu Glu Met
            740                 745                 750

Thr Ser Ala Arg Pro Arg Arg Met Ser Glu Val Pro Ala Ala Ser Thr
            755                 760                 765

Val Lys Pro Ile Pro Lys Ala Ser Ser Leu Phe Ile Leu Ser His Thr
            770                 775                 780

Asn Ser Phe Arg Val Phe Cys Asn Met Val Val Asn His Ser Tyr Phe
785                 790                 795                 800

Thr Asn Ala Val Leu Phe Cys Ile Leu Val Ser Ser Ala Met Leu Ala
            805                 810                 815

Ala Glu Asp Pro Leu Gln Ala Asn Ser Thr Arg Asn Met Ile Leu Asn
            820                 825                 830

Tyr Phe Asp Tyr Phe Phe Thr Ser Val Phe Thr Val Glu Ile Thr Leu
            835                 840                 845

Lys Val Ile Val Phe Gly Leu Val Phe His Lys Gly Ser Phe Cys Arg
            850                 855                 860

Asn Ala Phe Asn Leu Leu Asp Ile Leu Val Val Ala Val Ser Leu Thr
865                 870                 875                 880

Ser Phe Val Leu Arg Thr Asp Ala Met Ser Val Val Lys Ile Leu Arg
            885                 890                 895

Val Leu Arg Val Leu Arg Pro Leu Arg Ala Ile Asn Arg Ala Lys Gly
            900                 905                 910
```

-continued

```
Leu Lys His Val Val Gln Cys Val Ile Ala Val Lys Thr Ile Gly
        915                 920                 925

Asn Ile Met Leu Val Thr Phe Met Leu Gln Phe Met Phe Ala Ile Ile
        930                 935                 940

Gly Val Gln Leu Phe Lys Gly Thr Phe Phe Leu Cys Asn Asp Leu Ser
945                 950                 955                 960

Lys Met Thr Glu Ala Glu Cys Arg Gly Glu Tyr Ile His Tyr Glu Asp
                965                 970                 975

Gly Asp Pro Thr Lys Pro Val Ser Lys Lys Arg Val Trp Ser Asn Asn
                980                 985                 990

Asp Phe Asn Phe Asp Asn Val Gly Asp Ala Met Ile Ser Leu Phe Val
        995                 1000                1005

Val Ser Thr Phe Glu Gly Trp Pro Gln Leu Leu Tyr Val Ala Ile
        1010                1015                1020

Asp Ser Asn Glu Glu Asp Lys Gly Pro Ile His Asn Ser Arg Gln
        1025                1030                1035

Ala Val Ala Leu Phe Phe Ile Ala Phe Ile Val Ile Ala Phe
        1040                1045                1050

Phe Met Met Asn Ile Phe Val Gly Phe Val Ile Val Thr Phe Gln
        1055                1060                1065

Asn Glu Gly Glu Arg Glu Tyr Glu Asn Cys Glu Leu Asp Lys Asn
        1070                1075                1080

Gln Arg Lys Cys Ile Glu Phe Ala Leu Lys Ala Lys Pro His Arg
        1085                1090                1095

Arg Tyr Ile Pro Arg Asn Arg Leu Gln Tyr Arg Val Trp Trp Phe
        1100                1105                1110

Val Thr Ser Arg Ala Phe Glu Tyr Val Ile Phe Leu Ile Ile Val
        1115                1120                1125

Met Asn Thr Val Ser Leu Ala Cys Lys His Tyr Pro Ser Ser Arg
        1130                1135                1140

Gly Phe Glu Asp Phe Leu Asp Val Phe Asn Leu Ile Phe Thr Gly
        1145                1150                1155

Val Phe Ala Phe Glu Ala Val Leu Lys Ile Val Ala Leu Asn Pro
        1160                1165                1170

Lys Asn Tyr Ile Ser Asp Arg Trp Asn Val Phe Asp Leu Leu Val
        1175                1180                1185

Val Val Gly Ser Phe Ile Asp Ile Thr Tyr Gly Lys Leu Asn Pro
        1190                1195                1200

Gly Gly Thr Asn Leu Ile Ser Ile Asn Phe Phe Arg Leu Phe Arg
        1205                1210                1215

Val Met Arg Leu Val Lys Leu Leu Ser Arg Gly Glu Gly Ile Arg
        1220                1225                1230

Thr Leu Leu Trp Thr Phe Met Lys Ser Phe Gln Ala Leu Pro Tyr
        1235                1240                1245

Val Ala Leu Leu Ile Val Leu Leu Phe Phe Ile Tyr Ala Val Ile
        1250                1255                1260

Gly Met Gln Phe Phe Gly Lys Val Ala Leu Asp Asp Ser Thr Ser
        1265                1270                1275

Ile His Arg Asn Asn Asn Phe His Ser Phe Pro Ala Ala Ile Leu
        1280                1285                1290

Val Leu Phe Arg Ser Ala Thr Gly Glu Ala Trp Gln Asp Ile Met
        1295                1300                1305
```

-continued

```
Leu Ser Cys Ser Asp Arg Glu Asp Val Arg Cys Asp Pro Met Ser
1310                1315                1320

Asp Asp Tyr His Lys Gly Gly Leu Asn Glu Ser Arg Cys Gly Asn
1325                1330                1335

Asn Phe Ala Tyr Pro Tyr Phe Ile Ser Phe Phe Met Leu Cys Ser
1340                1345                1350

Phe Leu Val Ile Asn Leu Phe Val Ala Val Ile Met Asp Asn Phe
1355                1360                1365

Asp Tyr Leu Thr Arg Asp Trp Ser Ile Leu Gly Pro His His Leu
1370                1375                1380

Glu Glu Phe Val Arg Leu Trp Ser Glu Tyr Asp Pro Asp Ala Lys
1385                1390                1395

Gly Arg Ile Lys His Leu Asp Val Val Thr Leu Leu Arg Lys Ile
1400                1405                1410

Ser Pro Pro Leu Gly Phe Gly Lys Leu Cys Pro His Arg Leu Ala
1415                1420                1425

Cys Lys Arg Leu Val Ser Met Asn Met Pro Leu Asn Ser Asp Gly
1430                1435                1440

Thr Val Cys Phe Asn Ala Thr Leu Phe Ala Leu Val Arg Thr Asn
1445                1450                1455

Leu Lys Ile Tyr Thr Glu Gly Asn Ile Asp Glu Ala Asn Glu Gln
1460                1465                1470

Leu Arg Ser Ala Ile Lys Arg Ile Trp Lys Arg Thr His Lys Asp
1475                1480                1485

Leu Leu Asp Glu Val Val Pro Pro Ala Gly Lys Glu Asp Asp Val
1490                1495                1500

Thr Val Gly Lys Phe Tyr Ala Thr Phe Leu Ile Gln Asp Tyr Phe
1505                1510                1515

Arg Arg Phe Lys Lys Arg Lys Glu Met Glu Ala Lys Gly Val Leu
1520                1525                1530

Pro Ala Gln Thr Pro Gln Ala Met Ala Leu Gln Ala Gly Leu Arg
1535                1540                1545

Thr Leu His Glu Ile Gly Pro Glu Leu Lys Arg Ala Ile Ser Gly
1550                1555                1560

Asn Leu Glu Thr Asp Phe Asn Phe Asp Glu Pro Glu Pro Gln His
1565                1570                1575

Arg Arg Pro His Ser Leu Phe Asn Asn Leu Val His Arg Leu Ser
1580                1585                1590

Gly Ala Gly Ser Lys Ser Pro Thr Glu His Glu Arg Ile Glu Lys
1595                1600                1605

Gly Ser Thr Leu Leu Pro Phe Gln Pro Arg Ser Phe Ser Pro Thr
1610                1615                1620

His Ser Leu Ala Gly Ala Glu Gly Ser Pro Val Pro Ser Gln Met
1625                1630                1635

His Arg Gly Ala Pro Ile Asn Gln Ser Ile Asn Leu Pro Pro Val
1640                1645                1650

Asn Gly Ser Ala Arg Arg Leu Pro Ala Leu Pro Pro Tyr Ala Asn
1655                1660                1665

His Ile His Asp Glu Thr Asp Asp Gly Pro Arg Tyr Arg Asp Thr
1670                1675                1680

Gly Asp Arg Ala Gly Tyr Asp Gln Ser Ser Arg Met Val Val Ala
1685                1690                1695

Asn Arg Lys Tyr Ala Asp Ala Arg Ile Val Gly Ala Ala Arg Arg
```

-continued

```
        1700              1705              1710
Glu Ile Glu Glu Ala Tyr Ser Leu Gly Glu Gln Glu Ile Asp Leu
        1715              1720              1725

Ala Ala Asp Ser Leu Ala Pro Leu Met Gln His Val Gly Met His
        1730              1735              1740

Asp Ile Arg Asp Ile Asn Glu Asn Ser Arg Ser Ala Leu Leu Arg
        1745              1750              1755

Pro Ala Glu Asn Ser Ser Arg Gln His Asp Ser Arg Gly Gly Ser
        1760              1765              1770

Gln Glu Asp Leu Leu Leu Val Thr Thr Leu
        1775              1780
```